United States Patent
Bakker et al.

(10) Patent No.: US 10,358,492 B2
(45) Date of Patent: *Jul. 23, 2019

(54) BISPECIFIC IGG ANTIBODIES AS T CELL ENGAGERS

(71) Applicant: Merus N.V., Utrecht (NL)

(72) Inventors: Alexander Berthold Hendrik Bakker, Utrecht (NL); Pieter Fokko Van Loo, Utrecht (NL); Ton Logtenberg, Utrecht (NL)

(73) Assignee: Merus N.V., Utrecht (NL)

( * ) Notice: Subject to any disclaimer, the term of this patent is extended or adjusted under 35 U.S.C. 154(b) by 649 days.

This patent is subject to a terminal disclaimer.

(21) Appl. No.: 14/040,023

(22) Filed: Sep. 27, 2013

(65) Prior Publication Data

US 2014/0120096 A1 May 1, 2014

Related U.S. Application Data

(60) Provisional application No. 61/706,543, filed on Sep. 27, 2012, provisional application No. 61/834,915, filed on Jun. 14, 2013.

(51) Int. Cl.
| | |
|---|---|
| *C12P 21/08* | (2006.01) |
| *C07K 16/00* | (2006.01) |
| *C07K 16/28* | (2006.01) |
| *C07K 16/30* | (2006.01) |
| *A61K 39/00* | (2006.01) |

(52) U.S. Cl.
CPC .......... *C07K 16/28* (2013.01); *C07K 16/2809* (2013.01); *C07K 16/2851* (2013.01); *C07K 16/3061* (2013.01); *A61K 2039/505* (2013.01); *C07K 2317/21* (2013.01); *C07K 2317/31* (2013.01); *C07K 2317/526* (2013.01); *C07K 2317/53* (2013.01); *C07K 2317/55* (2013.01); *C07K 2317/569* (2013.01); *C07K 2317/70* (2013.01); *C07K 2317/71* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,801,687 A | 1/1989 | Ngo | |
| 4,816,567 A | 3/1989 | Cabilly et al. | |
| 5,151,504 A | 9/1992 | Croze | |
| 5,457,035 A | 10/1995 | Baum et al. | |
| 5,731,168 A | 3/1998 | Carter et al. | |
| 7,642,228 B2 | 1/2010 | Carter et al. | |
| 8,592,562 B2 | 11/2013 | Kannan et al. | |
| 9,145,588 B2 | 9/2015 | Throsby et al. | |
| 9,248,181 B2 | 2/2016 | De Kruif et al. | |
| 9,248,182 B2 | 2/2016 | De Kruif et al. | |
| 9,358,286 B2 | 6/2016 | De Kruif et al. | |
| 9,758,805 B2 | 9/2017 | De Kruif et al. | |
| 2003/0078385 A1 | 4/2003 | Arathoon et al. | |
| 2006/0171929 A1 | 8/2006 | Clark et al. | |
| 2006/0177451 A1 | 8/2006 | van den Oudenrijn et al. | |
| 2006/0177896 A1* | 8/2006 | Mach | C07K 16/2809 435/69.1 |
| 2009/0092582 A1† | 4/2009 | Bogin | |
| 2009/0182127 A1 | 7/2009 | Kjaergaard et al. | |
| 2010/0015133 A1 | 1/2010 | Igawa et al. | |
| 2010/0069614 A1 | 3/2010 | Houtzager et al. | |
| 2010/0146647 A1* | 6/2010 | Logtenberg | A01K 67/0278 800/4 |
| 2010/0286374 A1 | 11/2010 | Kannan et al. | |
| 2010/0331527 A1* | 12/2010 | Davis | C07K 16/2809 530/387.3 |
| 2011/0054151 A1* | 3/2011 | Lazar | A61K 47/48507 530/389.2 |
| 2011/0195454 A1 | 8/2011 | McWhirter et al. | |
| 2013/0096020 A1 | 4/2013 | Throsby et al. | |
| 2013/0115208 A1 | 5/2013 | Ho et al. | |
| 2013/0336981 A1 | 12/2013 | de Kruif et al. | |
| 2014/0072579 A1 | 3/2014 | De Kruif et al. | |
| 2014/0120096 A1 | 5/2014 | Bakker et al. | |
| 2014/0140999 A1 | 5/2014 | De Kruif et al. | |
| 2015/0139996 A1 | 5/2015 | De Kruif et al. | |
| 2015/0196637 A1 | 7/2015 | De Kruif et al. | |
| 2016/0130367 A1 | 5/2016 | Throsby et al. | |
| 2016/0177364 A1 | 6/2016 | De Kruif et al. | |
| 2016/0368988 A1 | 12/2016 | Bakker et al. | |

FOREIGN PATENT DOCUMENTS

| | | |
|---|---|---|
| CN | 1984931 A | 6/2007 |
| EP | 0120694 A2 | 10/1984 |
| EP | 0314161 A1 | 5/1989 |
| EP | 0481790 A2 | 4/1992 |
| EP | 0523949 A1 | 1/1993 |
| EP | 1870459 A1 | 12/2007 |

(Continued)

OTHER PUBLICATIONS

Noordhuis et al., 2010, Blood, vol. 116: 2890.*
IMGT scientific chart, 2016, pp. 1-5.*
Canfield et al., 1991, J. Exp. Med. vol. 173: 1483-1491.*
Transy et al., 1989, Eur. J. Immunol. vol. 19: 947-950.*
Atwell et al., JMB 270:26-35 (1997).
Baeuerle, Patrick A. et al., Cancer Res., vol. 69(12):4941-4944 (2009).
Bogan J. Mol. Biol., 280(1): 1-9 (1998).
Carter et al., J. Hematother 4:463-470 (1995).
Carter et al., J. Immunol. Methods 248:7-15 (2001).
Davies et al., Biotech. 13:475-479 (1995).
Davis JH. et al., Protein Engineering, Design & Selection (23)195-202 (2010).

(Continued)

*Primary Examiner* — Amy E Juedes
(74) *Attorney, Agent, or Firm* — Sterne, Kessler, Goldstein & Fox P.L.L.C.

(57) ABSTRACT

Bispecific IgG antibodies which bind to CLEC12A and an antigen on an immune effector cell are provided.

30 Claims, 20 Drawing Sheets

Specification includes a Sequence Listing.

(56) References Cited

FOREIGN PATENT DOCUMENTS

| | | |
|---|---|---|
| JP | H 11-500915 A | 1/1999 |
| JP | 2011/508604 A | 3/2011 |
| WO | 1996027011 A1 | 9/1996 |
| WO | 1998050431 A2 | 11/1998 |
| WO | 00/63403 A2 | 10/2000 |
| WO | 03/004704 A2 | 1/2003 |
| WO | 2003/107218 A1 | 12/2003 |
| WO | 20041009618 A2 | 1/2004 |
| WO | 2004/061104 A2 | 7/2004 |
| WO | 2005/000894 A2 | 1/2005 |
| WO | 2005/118635 A2 | 12/2005 |
| WO | 2006/028936 A2 | 3/2006 |
| WO | 2006/06905 A1 | 10/2006 |
| WO | 2006/105338 A2 | 10/2006 |
| WO | 2007/10205 A2 | 10/2007 |
| WO | 2007/47901 A1 | 12/2007 |
| WO | 2008/027236 A2 | 3/2008 |
| WO | 2008/119353 A1 | 10/2008 |
| WO | 2009/051974 A1 | 4/2009 |
| WO | 2009051974 A1 † | 4/2009 |
| WO | 2009/080251 A1 | 7/2009 |
| WO | 2009/080252 A1 | 7/2009 |
| WO | 2009/080253 A1 | 7/2009 |
| WO | 2009/089004 A1 | 7/2009 |
| WO | 2009/098596 A2 | 8/2009 |
| WO | 2009/157771 A2 | 12/2009 |
| WO | 2010/084197 A1 | 7/2010 |
| WO | 2010/108127 A1 | 9/2010 |
| WO | 2010/129304 A2 | 11/2010 |
| WO | 2010/151792 A1 | 12/2010 |
| WO | 2011/028952 A1 | 3/2011 |
| WO | 2011/028953 A1 | 3/2011 |
| WO | 2011143545 A1 | 11/2011 |
| WO | 2012/020096 A1 | 2/2012 |
| WO | 2012023053 A2 | 2/2012 |
| WO | 2012/058768 A1 | 5/2012 |
| WO | 2012/131555 A2 | 10/2012 |
| WO | 2013/157954 A1 | 10/2013 |
| WO | 2014/051433 A1 | 4/2014 |

OTHER PUBLICATIONS

Deisenhofer, J. Biochemistry, vol. 20 (9), 2361-2370, 1981.
Ellerson JR. et al., J. Immunol 1976 (116) 510-517.
Gunasekaran et al., J.Biol.Chem. 2010(285)19637-19646.
Hendsch et al., J. Am. Chem. Soc. 2001(123)1264-1265.
Kumar et al., JBC 2001(276)24971-24977.
Marvin et al., Biochem. 42:7077-7083 (2003).
McPhee et al., PNAS 1996(93)11477-11481.
Merchant et al., Nature biotechnology 1998(16)677.
Merus, www.merus.nl, press release, 3 pages, dated Jun. 17, 2013.
Merus, www.merus.nl, press release, 2 pages, dated Jan. 7, 2013.
Miller S., J. Mol. Biol. 1990(216)965-973.
Nieba et al. Prot. Eng. 10:435-444 (1997).
Nohaile et al., PNAS 2001(98)3109-3114.
Padlan, Advances in Protein Chemistry 1996 (49) 57-133.
Papadea and Check. Crit Rev Clin Lab Sci. 1989;27(1):27-58.
Raffen et al. Prot. Eng. 11:303-309 (1998).
Ridgway Protein Engineering 1996(9)617-621.
Sal-Man et al., Biochem J 2005(385)29-36.
Schiffer et al. JMB 203:799-802 (1988).
Selzer et al. Nat. Struc. Biol. 7:537-541 (2000).
Sheinerman et al. Curr. Op. Struc. Biol. 10:153-159 (2000).
Sinha et al., Biophys. J. 83:2946-2968 (2002).
Sinha et al., Curr Prot Pept Sci 2002(3)601-614.
Strelkauskas et al., Hybridoma 6:479-488 (1987).
Van Rhenen, Anna et al., Blood, vol. 110:2659-2666 (2007).
Zhao, Xiaoxian et al., Haematologica, vol. 95(1):71-78 (2010).
Zhu et al. Protein Sci. 6:781-788, 1997.
Strop, R et al., "Generating Bispecific Human IgGI and IgG2 Antibodies from Any Antibody Pair," The Journal of Molecular Biology, vol. 420:240-219 (2012).
Bargou, R. et al., "Tumor regression in cancer patients by very low doses of a T cell-engaging antibody," Science, vol. 321 (5891):974-977 (2008).
Armour, K.L. et al., "Differential binding to human FcgammaRIIa and FcgammaRIIb receptors by human IgG wildtype and mutant antibodies," Mol.Immunol., vol. 40(9): 585-593 (2003).
Bakker, AB et al., "C-type lectin-like molecule-1: a novel myeloid cell surface marker associated with acute myeloid leukemia," Cancer Research, vol. 64(22): 8443-8450 (2004).
Schaefer, G. et al, "A two-in-one antibody against HER3 and EGFR has superior inhibitory activity compared with monospecific antibodies," Cancer Cell, vol. 20(4): 472-486 (2011).
Bendig, MM., "The production of foreign proteins in mammalian cells," Genet Eng., (7):91-127 (1988).
Bluemel, C. et al., "Epitope distance to the target cell membrane and antigen size determine the potency of T cell-mediated lysis by BiTE antibodies specific for a large melanoma surface antigen," Cancer Immunol., vol. 59(8):1197-1209 (2010).
Bostrom, J., "Variants of the antibody herceptin that interact with HER2 and VEGF at the antigen binding site," Science, vol. 323(5921):1610-1614 (2009).
Capelle, MA et al., "Spectroscopic characterization of; antibodies adsorbed to aluminium adjuvants: correlation with antibody vaccine immunogenicity," Vaccine, vol. 23(14):1686-1694 (2005).
Chatenoud, L. et al., "In vivo cell activation following OKT3 administration. Systemic cytokine release and modulation by corticosteroids," Transplantation, vol. 49(4): 697-702 (1990).
Chen, C.H., et al., "Dendritic-cell-associated C-type lectin 2 (DCAL-2) alters dendritic-cell maturation and cytokine production," Blood, vol. 107(4):1459-1467 (2006).
Chen, C.H.et al., "Effect of Duration of Osmotherapy on blood-brain barrier disruption and regional cerebral edema after experimental stroke," Blood, Journal of Cerebral Blood Flow & Metabolism, vol. 26: 951-958 (2006).
Chen, C.H., H. et al., "Dendritic-cell-associated C-type lectin 2 (DCAL-2) alters dendritic-cell maturation and cytokine production," Blood, vol. 107(4) GenBank Access. No. AY426759 (2008).
Coligan JE, "Commonly used detergents," Curr Protoc Protein Sci., Appendix 1:Appendix 1B (2001).
Cui, H. et al., "Chemically Programmed Bispecific Antibodies That Recruit and Activate T Cells," The Journal of Biological Chemistry, vol. 287(34): 28206-28214 (2012).
De Kruif, J. et al., "Generation of stable cell clones expressing mixtures of human antibodies," Biotechnol Bioeng, vol. 106(5): 741-750 (2010).
de Vries, SJ. et al, "The HADDOCK web server for data driven biomolecular docking," vol. 5(5):883-897 (2010).
Dekruif, J. et al., "Selection and application of human single chain Fv antibody fragments from a semi-synthetic phage antibody display library with designed CDR3 regions," J. Mol Biol., vol. 248(1): 97-105 (1995).
Demeule, B., "Characterization of protein aggregation: the case of a therapeutic immunoglobulin," Biochem Biophys. Acta, vol. 1774(1): 146-153 (2007).
Demeule, "Detection and characterization of protein aggregates by fluorescence microscopy," Int J; Pharm, 329(1-2):37-45 (2007).
Dewildt, RM et al., "Analysis of Heavy and Light Chain Pairings Indicates the Receptor Editing Shapes the Human Antibody Repertoire," J. Mol. Biol., vol. 285: 895-901 (1999).
Dreier, T. et al., "Extremely potent, rapid and costimulation-independent cytotoxic T-cell response against lymphoma cells catalyzed by a single-chain bispecific antibody," Int. J.Canc., vol. 100(6): 690-697 (2002).
Farnan, D. et al., "Multiproduct high-resolution monoclonal antibody charge variant separations by pH gradient ion-exchange chromatography," Anal Chem., vol. 81(21): 8846-8857 (2009).
Fraser, P. et al., "Cord Blood Transplantation Study (COBLT): cord blood bank standard operating procedures," J Hematother, vol. 7(6):521-561 (1995).
Geginat, J., A. et al, "Proliferation and differentiation potential of human CD8+ memory T-cell subsets in response to antigen or homeostatic cytokines," Blood, vol. 101(11): 4260-4266 (2003).

(56) References Cited

OTHER PUBLICATIONS

Gussow, D,. et al., "Humanization of monoclonal antibodies," Methods Enzymol., vol. 203: 99-121(1991).
Haagen, IA, et al., "The efficacy of CD3×CD19 bispecific monoclonal antibody (BsAb) in a clonogenic assay: the effect of repeated addition of BsAb and interleukin-2," Blood, vol. 85(11): 3208-3212 (1995).
Han, Y. et al., "KLRL1, a novel killer cell lectin like receptor, inhibits natural killer cell cytotoxicity," Blood, vol. 104(9): 2856-2866 (2004).
Idusogie, EE, "Mapping of the C1q binding site on rituxan, a chimeric antibody with a human IgG1 Fc," J Immunol., vol. 164(8):4178-4184 (2000).
Ionescu, RM. et al, Contribution of variable domains to the; stability of humanized IgG1 monoclonal antibodies, 2008, J. Pharm Sci., vol. 97(4):1414-1426 ( 2008).
Kabat, EA., et al., "Identical V region amino acid sequences and segments of sequences in antibodies of different specificities. Relative contributions of VH and VL genes, minigenes, and complementarity-determining regions to binding of antibody-combining sites," J Immunol.,vol. 47(5):1709-1719 (1991).
Kipriyanov, SM. et al., "Bispecific CD3×CD19 diabody for T cell-mediated lysis of malignant human B cells," Int. J. Cancer, vol. 77(5): 763-772 (1998).
Kontermann, R.E., "Dual targeting strategies with bispecific antibodies," MAbs, vol. 4(2): 182-197 (2012).
Lakowicz, JR "Principles of fluorescence spectroscopy, 2nd edition," Kluwer Academic/Plenum Publisher (2006).
Lanzavecchia, A. et al., "Lysis of nonnucleated red blood cells by cytotoxic T lymphocytes," Eur.J.Imm., vol. 17(7): 1073-1074 (1987).
Lanzavecchia, A. et al., "The Use of Hybrid Hybridomas to target human cytotoxic T lymohocytes," Eur.J.Imm., vol. 17(1)105-111 (1987).
Lee, B. et al. "The interpretation of protein structures: estimation of static accessibility," J Mol Biol., vol. 55(3): 379-400 (1971).
Liesveld JL., "Expression of IgG Fc receptors in myeloid leukemic cell lines. Effect of colony-stimulating factors and cytokines," J. Immunol., vol. 140(5):1527-1533 (1988).
Liu, H. et al., "Heterogeneity of monoclonal antibodies," J Pharm Sci., vol. 97(7): 2426-2447 (2008).
Liu, MA., "Heteroantibody duplexes target cells for lysis by cytotoxic T lymphocytes," PNAS, vol. 82(24): 8648-8652 (1985).
Loeffler A. et al., "A recombinant bispecific single-chain antibody, CD193CD3, induces rapid and high lymphoma-directed cytotoxicity by unstimulated T lymphocytes," Blood, vol. 95(6):2098-2103 (2000).
Mariuzza, RA. et al., "The structural basis of antigen-antibody recognition," Annu Rev Biophys Biophys Chem., vol. 16: 139-159 (1987).
Marshall, A.S. et al. "Identification and Characterization of a Novel Human Myeloid Inhibitory C-type Lectin-like Receptor (MICL) That Is Predominantly Expressed on Granulocytes and Monocytes," J Biol Chem., vol. 279(15): 14792-14802 (2004).
Moore, PA. et al., "Application of dual affinity retargeting molecules to achieve optimal redirected T cell killing of B-cell lymphoma," Blood, vol. 117(17):4542-4551 (2011).
Moshaver, B. et al.,"Identitication of a small subpopulation of candidate leukemia-initiating cells in the side population of patients with acute myeloid leukemia," Stem Cells, vol. 26(12): 3059-3067 (2008).
Nissim, A. et al., "Antibody fragments from a 'single pot' phage display library as immunochemical reagents," EMBO J., vol. 13(3): 692-698 (1994).
Norde, WJ. et al., "Myeloid leukemic progenitor cells can be specifically targeted by minor histocompatibility antigen LRH-1-reactive cytotoxic T cells," Blood, vol. 113(10):2312-2323 (2009).
Offner, S. et al., "Induction of regular cytolytic T cell synapses by bispecific single-chain antibody constructs on MHC class I-negative tumor cells," Molecular Immunology, vol. 43(6):763-771 (2006).
Oganesyan, V. et al., "Structural characterization of a human Fc fragment engineered for lack of effector functions," Acta Crystallogr D Biol Crystallogr., vol. 64(Pt. 6):700-704 (2008).
Sali, A. et al, "Comparative protein modelling by satisfaction of spatial restraints," J. Mol. Biol., vol. 234(3):779-815 (1993).
Sheridan, C., "Amgen swallows Micromet to BiTE into ALL market," Nat Biotechnol., vol. 30(4):300-301 (2012).
Shields, RL. et al., "High resolution mapping of the binding site on human IgG1 for Fc gamma RI, Fc gamma RII, Fc gamma RIII, and FcRn and design of IgG1 variants with improved binding to the Fc gamma R," JBC, vol. 276(9): 6591-6604 (2001).
Sluijter, B.J., et al., "4-1BB-mediated expansion affords superior detection of in vivo primed effector memory CD8+ T cells from melanoma sentinel lymph nodes," Clin Immunol, vol. 137(2): 221-233 (2010).
Spiess, C., et al., "Alternative molecular formats and therapeutic applications for bispecific antibodies," Mol. Immunol., vol. 67(2 Pt A):95-106 (2015).
Staerz, UD. et al., "Hybrid hybridoma producing a bispecific monoclonal antibody that can focus effector T-cell activity," PNAS, vol. 83(5):1453-1457 (1986).
Tahallah, N., "The effect of the source pressure on the abundance of ions of noncovalent protein assemblies in an electrospray ionization orthogonal time-of-flight instrument," Rapid Commun Mass Spectrom, vol. 15(8):596-601 (2001).
Zeidler, R. et al., "Simultaneous activation of T cells and accessory cells by a new class of intact bispecific antibody results in efficient tumor cell killing," J. Immunol., vol. 163(3): 1246-1252 (1999).
Zhang, W. et al., "*Homo sapiens* C-type lectin protein CLL-1 mRNA, complete cds," GenBank: AF247788.1, 1 page (2002).
Chames, P., et al., "Bispecific antibodies for cancer therapy: the light at the end of the tunnel?", MAbs. vol. 1(6):539-547 (2009).
U.S. Appl. No. 14/974,581, filed Dec. 18, 2015 Cornelis A. de Kruif.
U.S. Appl. No. 15/205,629, filed Jul. 8, 2016, Alexander Berthold Hendrik Bakker.
U.S. Appl. No. 15/121,619, filed Aug. 25, 2016, Ton Logtenberg.
U.S. Appl. No. 15/121,623, filed Aug. 25, 2016, Cecilia Anna Wilhelmina Geuijen.
U.S. Appl. No. 13/866,747, Oct. 4, 2015.
Araya, CL et al.,"Deep mutational scanning: assessing protein function on a massive scale," Trends Biotechnol., vol. 29(9):435-442 (2011).
Pantazes, RJ, et al., "OptCDR: a general computational method for the design of antibody complementarity determining regions for targeted epitope binding," Protein Eng., vol. 23(11):849-858 (2010).
Peled, JU et al., "The biochemistry of somatic hypermutation," Ann. Rev. Immunol., vol. 26:481-511 (2008).
Ponsel, D. et al.," High Affinity, Developability and Functional Size: The Holy Grail of Combinatorial Antibody Library Generation," Molecules, vol. 16:3675-3700 (2011).
Sircar, A. et al., "RosettaAntibody: antibody variable region homology modeling server," Nuc. Acids Res. 37:1093, W474-W479 (2009).
Thom, G. et al.,"Probing a protein-protein interaction by in vitro evolution," PNAS, vol. 103(20):7619-7624 (2006).
Vajdos, FF. et al., Comprehensive functional maps of the antigen-binding site of an anti-ErbB2 antibody obtained with shotgun scanning mutagenesis, J Mol Biol., vol. 320(2): 415-428 (2002).
U.S. Appl. No. 15/155,743, filed May 16, 2016, Cornelis A. De Kruif.
U.S. Appl. No. 15/496,807, filed Apr. 25, 2017, Cornelis A. De Kruif.
U.S. Appl. No. 14/081,848, Feb. 12, 2016.
U.S. Appl. No. 14/081,848, Apr. 10, 2015.
U.S. Appl. No. 13/866,747, Sep. 29, 2015.
U.S. Appl. No. 13/866,747, Apr. 10, 2015.
U.S. Appl. No. 13/866,756, Sep. 18, 2015.
U.S. Appl. No. 13/866,756, Apr. 13, 2015.
U.S. Appl. No. 14/395,330, Apr. 10, 2015.
U.S. Appl. No. 15/205,629, May 10, 2017.
U.S. Appl. No. 15/205,629, Nov. 1, 2016.
U.S. Appl. No. 14/974,581, Jan. 25, 2017.
U.S. Appl. No. 14/974,581, Sep. 28, 2016.

(56) References Cited

OTHER PUBLICATIONS

U.S. Appl. No. 14/974,581, May 10, 2016.
Abbott, WM et al., "Current approaches to fine mapping of antigen-antibody interactions," Immunology, vol. 142(4):526-535 (2014).
Armour, K.L. et al., "The contrasting IgG-binding interactions of human and herpes simplex virus Fc receptors," Mediation and Modulation of Antibody Function, Biochemical Society Transactions, vol. vol. 30(part 4): 495-500 (2002).
De Kruif, J. et al., "Human immunoglobulin repertoires against Tetanus toxoid contain a large and diverse fraction of high-affinity VH genes" J. Mol. Biol., 387: 548-558 (2009).
Klein, C. et al., "Progress in overcoming the chain association issue in bispecific heterodimeric IgG antibodies," mAbs, vol. 4(6):653-663 (2012).
Legall, F. et al., "Effect of linker sequences between the antibody variable domains on the formation, stability and biological activity of a bispecific tandem diabody," Protein Eng Des Sel., vol. 17(4):357-366 (2004).
Marvin, JS. "Recombinant approaches to IgG-like bispecific antibodies," Acta Pharmacol Sin.,vol. 26(6):649-658 (2005).
Reusch, U. et al., "Beyond mAbs with TandAbs," Innovations in Pharmaceutical Technology, 4 pages, (2011).
Sugiyama, Y., et al., "In vitro Anti-tumor Activity of Anti-c-erbB-2×Anti-CD3 epsilon Bifunctional Monoclonal Antibody," Japanese Journal of Cancer Research, vol. 83 (6):563-567 (1992).
Suntharalingam, G. et al., "Cytokine storm in a phase 1 trial of the anti-CD28 monoclonal antibody TGN1412," N Engl J Med, vol. 355 (10): 1018-10128 (2006).
UniProt Entry Q5QGZ9, UniProt, retrieved Jan. 21, 2015, from <http://www.uniprot.org/uniprotlQ5QGZ9.
de Kruif et al., "Human immunoglobulin repertoires against Tetanus toxoid contain a large and diverse fraction of high-affinity VH genes" J. Mol. Biol. 387: 548-558, 2009.†
UniProt Entry Q5QGZ9, UniProt, retrieved Jan. 21, 2015, from <http://www.uniprot.org/uniprot/Q5QGZ9>.†
Uwe Reusch et al., Beyond mAbs with TandAbs, Innovations in Pharmaceutical Technology, 7 pages, Jun. 2011.†
Le Gall et al., Effect of linker sequences between the antibody variable domains on the formation, stability and biological activity of a bispecific tandem diabody, Protein Eng. Des. Sel, 17:357-366 (2004).†
Paul Carter, Bispecific human IgG by design, J. Immunol. Methods, 248:7-15 (2001).†
Baeuerle et al., Biospecific T-Cell Engaging Antibodies for Cancer Thera;y, Cancer Res., 69:4941-4944 (2009).†

\* cited by examiner
† cited by third party

CLL-1: predicted aa sequence Bakker et al.2004
KLRL1: translated aa sequence Han et al.2004 (= Zhang/Cao group; deposited under no. AF247788)
MICL: predicted aa sequence Marshall et al.2004 (deposited under no. AY498550)
DCAL-2: predicted aa sequence Chen et al.2006 (= E.A. Clark group deposited under no. AY426759)
CLEC12B: Predicted aa sequence H.F. Clark et al. 2003 (deposited under no. AY358810)

```
KLRL1     ----------MSEEVTYADLQFQNSSEMEKIPEIGKFGEKAPPAPSHVWRPAALFLTLLCLLLLIGLGVLASMFHVTLK----IEMKKMNKLQNI
MICL      ----------MSEEVTYADLQFQNSSEMEKIPEIGKFGEKAPPAPSHVWRPAALFLTLLCLLLLIGLGVLASMFHVTLK----IEMKKMNKLQNI
DCAL-2    ----------MSEEVTYADLQFQNSSEMEKIPEIGKFGEKAPPAPSHVWRPAALFLTLLCLLLLIGLGVLASMFHVTLK----IEMKKMNKLQNI
CLL-1     MWIDFFTYSSMSEEVTYADLQFQNSSEMEKIPEIGKFGEKAPPAPSHVWRPAALFLTLLCLLLLIGLGVLASMFHVTLK----IEMKKMNKLQNI
CLEC12B   ----------MSEEVTYATLTFQDSAGARNNRDGNNLRKRGHPAPSPIWRHAALGLVTLCLMLLIGLVTLGMMFLQISNDINSDSEKLSQLQKT

KLRL1     SEELQRNISLQLMSNMNI-------SNKIRNLSTTLQTIATKLCRELYSKEQEHKCKPCPRRWIWHKDSCYFLS-DDVQTWQESKMACAAQNAS
MICL      SEELQRNISLQLMSNMNI-------SNKIRNLSTTLQTIATKLCRELYSKEQEHKCKPCPRRWIWHKDSCYFLS-DDVQTWQESKMACAAQNAS
DCAL-2    SEELQRNISLQLMSNMNI-------SNKIRNLSTTLQTIATKLCRELYSKEQEHKCKPCPRRWIWHKDSCYFLS-DDVQTWQESKMACAAQNAS
CLL-1     SEELQRNISLQLMSNMNI-------SNKIRNLSTTLQTIATKLCRELYSKEQEHKCKPCPRRWIWHKDSCYFLS-DDVQTWQESKMACAAQNAS
CLEC12B   IQQQDNLSQQLGNSNNLSMEEEFLKSQISSVLKRQEQMAIKLCQELIIHTSDHRCNPCPKMWQWYQNSCYFTTNEEKTWANSRKDCIDKNST

KLRL1     LLKINNKNALEFIKSQSRS--YDYWLGLSPEEDSTRGMRVDNIINSSAW-VIRNAPDL-NNMYCGYINRLYVQYYHCTYKQRMICEKMANPVQL
MICL      LLKINNKNALEFIKSQSRS--YDYWLGLSPEEDSTRGMRVDNIINSSAW-VIRNAPDL-NNMYCGYINRLYVQYYHCTYKQRMICEKMANPVQL
DCAL-2    LLKINNKNALEFIKSQSRS--YDYWLGLSPEEDSTRGMRVDNIINSSAW-VIRNAPDL-NNMYCGYINRLYVQYYHCTYKQRMICEKMANPVQL
CLL-1     LLKINNKNALEFIKSQSRS--YDYWLGLSPEEDSTRGMRVDNIINSSAW-VIRNAPDL-NNMYCGYINRLYVQYYHCTYKKRMICEKMANPVQL
CLEC12B   LVKIDSLEEKDFLMSQPLLMFSFFWLGLSWDSSGRSWFWEDGSVPSPSLFSTKELDQINGSKGCAYFQKGNIYISRCSAEIFWICEKTAAPVKT

KLRL1     GSTYFREA
MICL      GSTYFREA
DCAL-2    GSTYFREA
CLL-1     GSTYFREA
CLEC12B   EDLD----
```

3056
VH (VDJ):

caggtgcagctggtgcagtctggcggcggagtggtgcagcccggcagaagcctgagactgagctgcgtgg
ccagcggcttcaccttcagcagctacggcatgcactgggtccgccaggcccctggcaagggactggaatg
ggtggccgccatctggtacaacggccggaagcaggactacgccgacagcgtgaagggccggttcaccatc
agccgggacaacagcaagaacaccctgtacctgcagatgaacagcctccgggccgaggacaccgccgtgt
actactgtacccggggcaccggctacaattggttcgaccctggggccagggcaccctggtcaccgtctc
cagt (SEQ ID NO: 26)

QVQLVQSGGGVVQPGRSLRLSCVASGFTFSSYGMHWVRQAPGKGLEWVAAIWYNGRKQDYADSVKGRFTI
SRDNSKNTLYLQMNSLRAEDTAVYYCTRGTGYNWFDPWGQGTLVTVSS (SEQ ID NO: 27)

VL/O12 (VJ):

Gacatccagatgacccagtctccatcctccctgtctgcatctgtaggagacagagtcaccatcacttgccgggca
agtcagagcattagcagctacttaaattggtatcagcagaaaccagggaaagcccctaagctcctgatctatgct
gcatccagtttgcaaagtggggtcccatcaaggttcagtggcagtggatctgggacagatttcactctcaccatc
agcagtctgcaacctgaagattttgcaacttactactgtcaacagagttacagtaccccctccaacgttcggccaa
gggaccaaggtggagatcaaac (SEQ ID NO: 28)

DIQMTQSPSSLSASVGDRVTITCRASQSISSYLNWYQQKPGKAPKLLIYAASSLQSGVPSRFSGSGSGTD
FTLTISSLQPEDFATYYCQQSYSTPPTFGQGTKVEIK (SEQ ID NO: 29)

3896
VH:

caggtgcagctggtggagtctggcggcggagtggtgcagcccggcagaagcctgagactgagctgcgccg
ccagcggcttcaccttcagaagctacggcatgcactgggtccgccaggcccctggcaagggactggaatg
ggtggccatcatctggtacagcggcagcaagaagaactacgccgacagcgtgaagggccggttcaccatc
agccgggacaacagcaagaacaccctgtacctgcagatgaacagcctccgggccgaggacaccgccgtgt
actactgtgcccggggcaccggctacaattggttcgaccctggggccagggcaccctggtcaccgtctc
cagt (SEQ ID NO: 30)

QVQLVESGGGVVQPGRSLRLSCAASGFTFRSYGMHWVRQAPGKGLEWVAIIWYSGSKKNYADSVKGRFTI
SRDNSKNTLYLQMNSLRAEDTAVYYCARGTGYNWFDPWGQGTLVTVSS (SEQ ID NO: 16)

CLEC12A BENCHMARK (3116)

VH:

caggtgcagctgcaggaatctggacccggactggtcaagcccagcgagacactgagcctgacctgtgtgg
tgtccggcggcagcatcagcagcagcaattggtggtcttgggtccgacagcccctggcaagggcctgga
atggatcggcgagatctaccacagcggcagccccgactacaaccccagcctgaagtccagagtgaccatc
agcgtggacaagagccggaaccagttcagcctgaagctgagcagcgtgacagccgccgataccgccgtgt
actactgcgccaaagtgtccaccggcggcttttttcgactactggggccagggcacactggtcaccgtctc
cagt (SEQ ID NO: 32)

QVQLQESGPGLVKPSETLSLTCVVSGGSISSSNWWSWVRQPPGKGLEWIGEIYHSGSPDYNPSLKSRVTI
SVDKSRNQFSLKLSSVTAADTAVYYCAKVSTGGFFDYWGQGTLVTSS (SEQ ID NO: 33)

VL:
O12

3918

VH:

caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaacccaacagtggtggcacaaactatgcacagaagtttcagggcagggtcacgatg
accagggacacgtccatcagcacagcctacatggagctgagcaggctgagatctgacgacacggccgtgt
attactgtgcaagagatggttacttcgctgacgcctttgattattggggccaaggtaccctggtcaccgt
ctccagt (SEQ ID NO: 34)

QVQLVQSGAEVKKPGASVKVSCKASGYTFTGYYMHWVRQAPGQGLEWMGWINPNSGGTNYAQKFQGRVTM
TRDTSISTAYMELSRLRSDDTAVYYCARDGYFADAFDYWGQGTLVTVSS (SEQ ID NO: 12)

VL:
O12

4327

VH:

caggtgcagctggtgcagtctggggctgaggtgaagaagcctggggcctcagtgaaggtttcctgcaagg
catctggatacaccttcaccagctactatatgcactgggtgcgacaggcccctggacaagggcttgagtg
gatgggaataatcaaccctagtggtggtagcacaagctacgcacagaagttccagggcagagtcaccatg
accagggacacgtccacgagcacagtctacatggagctgagcagcctgagatctgaggacacggccgtgt
attactgtgcaaagggcactactggtgattggtttgactactggggccaaggtaccctggtcaccgtctc
cagt (SEQ ID NO: 36)

QVQLVQSGAEVKKPGASVKVSCKASGYTFTSYYMHWVRQAPGQGLEWMGIINPSGGSTSYAQKFQGRVTM
TRDTSTSTVYMELSSLRSEDTAVYYCAKGTTGDWFDYWGQGTLVTVSS (SEQ ID NO: 4)

gaggtccagctggtgcagtctggggctgaggtgaagaagcctggggcctcagtgaaggtttcctgcaagg
catctggatacaccttcaccagctactatatgcactgggtgcgacaggcccctggacaagggcttgagtg
gatgggaataatcaaccctagtggtggtagcacaagctacgcacagaagttccagggcagagtcaccatg
accagggacacgtccacgagcacagtctacatggagctgagcagcctgagatctgaggacacggccgtgt
attactgtgcaaggggcaattatggtgatgagtttgactactggggccaaggtaccctggtcaccgtctc
cagt (SEQ ID NO: 38)

EVQLVQSGAEVKKPGASVKVSCKASGYTFTSYYMHWVRQAPGQGLEWMGIINPSGGSTSYAQKFQGRVTM
TRDTSTSTVYMELSSLRSEDTAVYYCARGNYGDEFDYWGQGTLVTVSS (SEQ ID NO: 8)

VL:
O12

BISPECIFIC IGG ANTIBODIES AS T CELL ENGAGERS

TECHNICAL FIELD

The invention relates to the field of antibody engineering. In particular it relates to the field of therapeutic (human) antibodies for the treatment of diseases involving aberrant cells. More in particular it relates to bispecific antibodies for the treatment of tumors.

SEQUENCE LISTING

The instant application contains a Sequence Listing which has been submitted electronically in ASCII format via EFS-Web and is hereby incorporated by reference in its entirety. Said ASCII copy, created on May 23, 2017 is named MRX5-010_Replacement_Sequence_Listing.txt and is 42,543 bytes in size.

BACKGROUND OF THE INVENTION

In laboratories, bispecific antibodies have been widely used for the retargeting of immune effector cells to tumor cells. In this case, one binding site is directed against a tumor-associated antigen (TAA) and the second antigen against a trigger molecule on the effector cells, such as for example CD3 on T cells (Kontermann, MABS 2012 (4) 182-197; Chames and Baty, MABS 2009 (1) 539-547; Moore et al. Blood 2011 (117) 4542-4551). The first bispecific antibodies targeting CD3 and a tumor cell associated antigen were of rodent nature and were produced using hybrid hybridomas (Liu et al. 1985 PNAS 82: 8648, Staerz et al. 1986 PNAS 83:1453, Lanzavecchia et al. 1987, Eur. J. Imm. 17:105). In these hybrid hybridomas the reassortment of Ig heavy and light chains resulted in the production of bispecific functional antibody molecules within a much larger pool of monospecific and non-functional bispecific antibodies resulting from heavy and light chain mispairing. Because of their double specificity, these functional bispecific antibodies were able to bridge murine and human cytotoxic T lymphocytes (CTL) to target cells and trigger cytotoxic function resulting in the lysis of tumor cells displaying the relevant antigen. However, the CD3×TAA bispecific IgG mediated induction of tumor cell lysis by polyclonal resting human T cells could not be achieved unless co-stimulation was provided by added exogenous IL-2 or anti-CD28 mAb. This is exemplified by the hybrid rat IgG2b/mouse IgG1 CD3×CD19 bispecific molecule that was able to induce lysis of the CD19 positive REH B-ALL tumor cell line by resting human T lymphocytes only upon co-administration of IL-2 (Haagen et al. 1995 Blood 85:3208). Zeidler et al. demonstrated using a similar rat IgG2b/mouse IgG2a CD3×Epcam molecule that bispecific IgG-induced lysis of Epcam-positive tumor cells could be achieved in mixed cell cultures comprising both peripheral blood mononuclear cells (PBMC) and tumor cells without addition of exogenous IL2 (Zeidler et al. 1999 J. Immunol. 163:1246). The authors claimed that the 'third' arm of the antibody, the Fc region, is causing this effect through interaction with Fcγ receptor-positive accessory cells present within the PBMC fraction. In particular, the strong activation potential was correlated to the hybrid subclass combination mouse IgG2a/rat IgG2b that, in contrast to other reported combinations (e.g., mouse IgG2a/mouse IgG1 or rat IgG2b/mouse IgG1), not only binds but also activates Fcγ receptor-positive accessory cells. This so-called triomAb CD3×Epcam bispecific antibody, also known as catumaxomab, has been developed clinically and has been registered in Europe for palliative treatment of abdominal tumors of epithelial origin. While this bispecific antibody has clearly demonstrated clinical efficacy, its rodent nature induces anti-product immune responses upon repetitive dosing and therefore prevents a widespread application of this format.

Alternative CD3×TAA formats have been explored to solve both the manufacturing issues and the immunogenicity problems associated with the hybrid rodent triomAb format. Such formats are often immunoglobulin-like molecules that deviate from full length human IgG molecules, and include molecules such as Dual-Affinity Re-Targeting (DART™) molecules that are developed by Macrogenics worldwide web at macrogenics.com/Platforms-DART.html, Bispecific T cell Engager (BiTE®) molecules that were developed by Micromet, now Amgen (Sheridan C, Nat Biotechnol. 2012 (30):300-1), Dual Variable Domain—immunoglobulin (DVD-Ig™) molecules that are developed by Abbott, and TandAb® RECRUIT molecules that are developed by Affimed world wide web at affimed.com/tandab-recruit. It was demonstrated for one of these formats that successful retargeting of peripheral blood lymphocytes to lyse CD19-positive tumor cells using a CD3×CD19 diabody required pre-activation the of the peripheral blood T lymphocytes, now using anti-CD3 antibody plus human IL-2 (Kipriyanov et al. 1998 Int. J. Can. 77:763). Other formats, such as the bivalent single chain Fv CD3×TAA BiTE® format (Loffler et al. 2000 Blood 95:2098) do not require pre-activation of resting T cells and is able to induce antigen positive tumor cell lysis in vitro in an extremely efficient manner (Dreier et al. 2002 Int. J. Canc. 100:690). Additional studies using BiTE®s targeting different TAAs revealed that the potent efficacy of the BiTE® format was correlated to the antigen size and particularly to the distance of the epitope on the TAA to the tumor cell membrane (Bluemel et al. 2010 Cancer Immunol. Immunother. 59:1197). The effective formation of cytolytic T cell synapses was demonstrated for BiTE® molecules which is explained to form the structural basis for their potency (Offner et al. Molecular Immunology 2006 (43) 763-771) which is also believed to be linked to the small size of the BiTE® format. If size matters, this would suggest that larger molecules such as intact IgG would be too large to form effective cytolytic synapses. The CD3× CD19 BiTE®, blinatumomab, has demonstrated remarkable clinical efficacy in refractory non-Hodgkin lymphoma and acute lymphatic leukemia patients (Bargou et al. 2008 Science 321:974). Although the CD3×CD19 BiTE® displays very efficient tumor cell lysis at low levels in vitro, administration of this bispecific format to patients is associated with significant challenges. Due to their small size, BiTE®s are rapidly cleared from the circulation and dosing of patients thus requires continuous infusion. As the dosing regimen has an overall duration of more than 2 months, this treatment has a significant impact on the quality of life of the patients.

There thus remains a need for effective full length bispecific T cell engaging IgG molecules in eradicating aberrant cells that combine a long circulatory half-life upon intravenous administration without the need for continuous infusion without being immunogenic and with only limited side effects.

BRIEF DESCRIPTION OF THE FIGURES

FIG. 1: CLEC12A and related sequences (SEQ ID NOs: 21-25).

FIG. 20: VH sequences of CD3-specific and CLEC12A-specific Fab arms. VL sequence of O12 common light chain. CDR sequences are bold and underlined.

SUMMARY OF THE INVENTION

Figure 2:
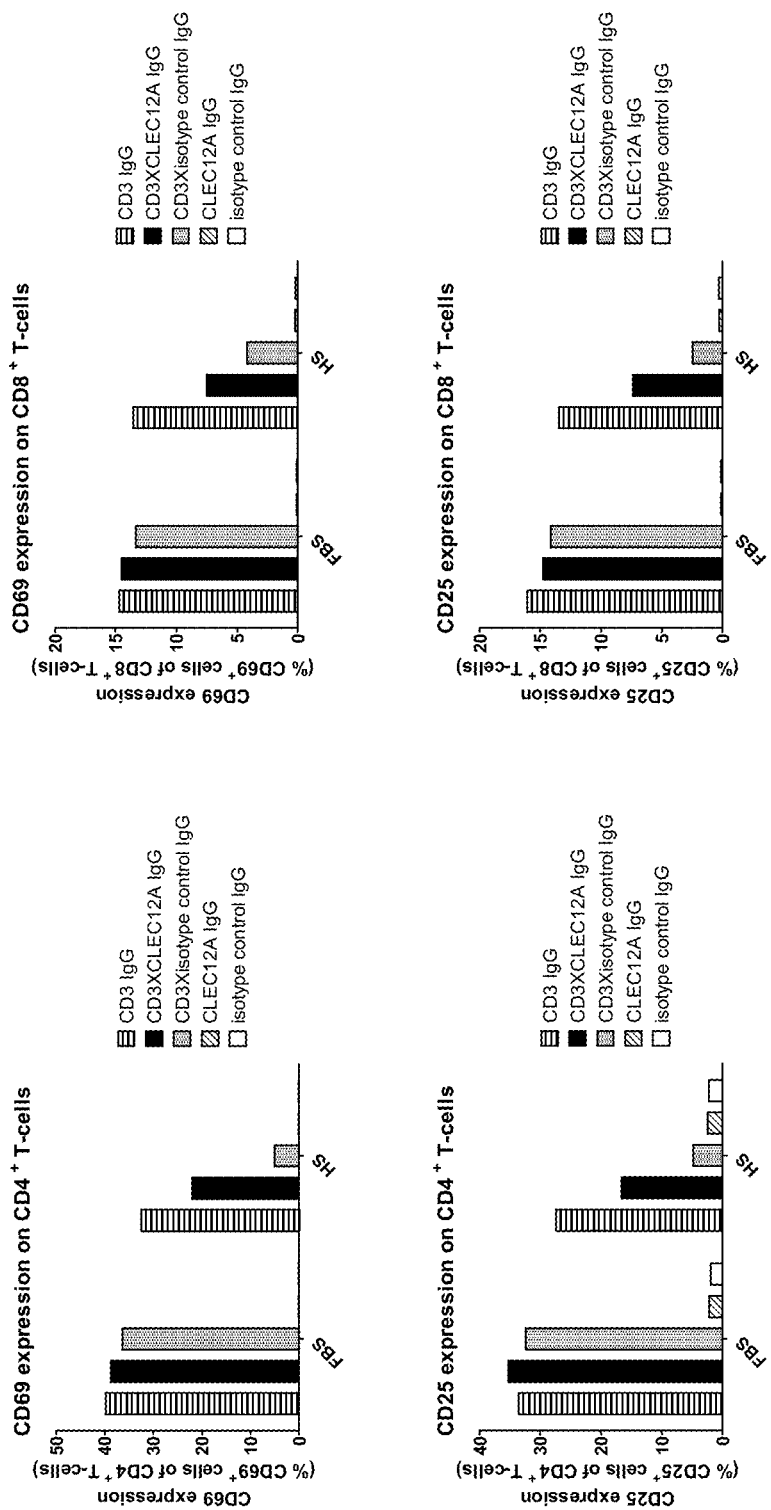
FIG. 2: T-cell activation by various antibodies: monoclonal bivalent CD3 IgG, bispecific CD3×CLEC12 IgG, bispecific CD3× isotype control IgG, monoclonal bivalent CLEC12A IgG, monoclonal bivalent isotype control IgG.

The present invention describes a fully human IgG bispecific full length antibody for the treatment of AML. One arm of the antibody binds an epitope on immune effector cells, preferably CD3, whilst the other arm targets CLEC12A, a myeloid cell specific surface target that is expressed in 90-95% of de novo and relapsed AML patients. CLEC12A is expressed on AML leukemic stem cells, but not on normal haematopoietic cells. Unlike CD33, CLEC12A is not expressed on erythroid precursors or megakaryocytes, so the CD3×CLEC12A bispecific IgG1 antibody of the present invention should not induce platelet or red blood cell depletion. Experiments with bone marrow cell colonies have shown that depletion of CLEC12A+ cells in normal bone marrow does not affect the myeloid lineages that give rise to platelets and red blood cells. A CD3×CLEC12A bispecific IgG antibody according to the present invention in a preferred embodiment contains a modified Fc region so as to reduce non-specific immune activation resulting from engagement of T cells and FcγR expressing cells within PBMC. Based on data described for the triomAb bispecific antibody in the prior art it was highly doubted that a CD3×TAA bispecific IgG of a fully human IgG1 format would be able to induce lytic anti-tumor activity in resting peripheral blood lymphocytes without the need for pre-activation of T cells. In addition, the available data for the BiTE® format suggested that a full length IgG molecule would be too large to create effective cytolytic synapses between tumor cells and effector cells. Surprisingly, we demonstrated that a fully human CD3×CLEC12A bispecific full length IgG1 was able to induce very efficient T cell mediated lysis of CLEC12A-positive HL60 AML tumor cells in vitro. In fact, effective lysis was mediated by resting T lymphocytes purified from PBMC without the need of prior activation of the T cells. Furthermore, we demonstrated that this lytic activity is not necessarily dependent on interactions with FcγR present on HL60 cells as this lytic activity was not affected by the presence of excess human IgG when the assay was performed in human serum containing media. This is the first time that a full length human IgG1 bispecific T cell engager antibody exerts efficient tumor cell lysis without the need of pre-activation of T cells or the need of active FcγR interactions. Effective lysis is achieved despite the relatively large size of the IgG1 when compared to BiTE® molecules. Remarkably, when CH2/lower hinge mutations were introduced in the CD3× CLEC12A bispecific IgG1 molecule to further decrease Fc receptor interactions, this still resulted in efficient tumor cell lysis by immune effector cells. A bispecific human IgG1 T cell engager antibody has advantages over current IgG that make use of the hybrid subclass combination mouse IgG2a/rat IgG2b, since a human IgG1 will be less immunogenic and can thus be applied for repeated therapy. In addition, a full length bispecific human IgG1 T cell engager antibody has advantages over immunoglobulin/like molecules such as DART™, TandAb® or BITE® as the full length human IgG1 is not rapidly cleared from the circulation and dosing of patients will thus not require continuous infusion, which is more beneficial to patients.

EMBODIMENTS

The invention provides a bispecific IgG antibody, wherein said bispecific IgG antibody comprises one arm that specifically recognizes CLEC12A or a functional equivalent thereof, and a second arm that specifically recognizes an antigen on immune effector cells capable of recruiting such cells to an aberrant cell expressing CLEC12A or said functional equivalent.

As used herein, the term "specifically recognizes CLEC12A or a functional equivalent thereof" means that said arm has the capability of specifically recognizing CLEC12A or said functional equivalent, in the situation that CLEC12A or said functional equivalent is present in the vicinity of said antibody. Likewise, the term "specifically recognizes an antigen on immune effector cells" means that said arm has the capability of specifically recognizing said antigen when said antigen is present in the vicinity of said antibody. Such antigen recognition by an antibody is typically mediated through the complementarity regions of the antibody and the specific three-dimensional structure of both the antigen and the antibody arm allowing these two structures to bind together with precision (an interaction similar to a lock and key), as opposed to random, non-specific sticking of antibodies. As an antibody typically recognizes an epitope of an antigen, and as such epitope may be present in other compounds as well, antibodies according to the present invention that "specifically recognize CLEC12A or a functional equivalent thereof", and "specifically recognize an antigen on immune effector cells" may recognize other compounds as well, if such other compounds contain the same kind of epitope. Hence, the terms "specifically recognizes CLEC12A or a functional equivalent thereof", "specifically recognizes an antigen on immune effector cells" and "specifically recognizes CD3" do not exclude binding of the antibodies to other compounds that contain the same (kind of) epitope. Instead, cross-reactivity is allowed. An antibody according to the present invention is typically capable of binding CLEC12A (or a functional equivalent thereof) and an antigen on immune effector cells, preferably CD3, with a binding affinity of at least $1\times10^{-5}$ M, as outlined in more detail below.

The term "antibody" as used herein means a proteinaceous molecule belonging to the immunoglobulin class of proteins, containing one or more domains that bind an epitope on an antigen, where such domains are derived from or share sequence homology with the variable region of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, or "specifically recognizing" is defined as binding with affinities (KD) of at least $1\times10^{-5}$ M, more preferably $1\times10^{-7}$ M, more preferably higher than $1\times10^{-9}$ M. Typically, antibodies for therapeutic applications have affinities of up to $1\times10^{-10}$ M or even higher. Antibodies of the present invention are typically bispecific full length antibodies of the human IgG subclass. Preferably, the antibodies of the present invention are of the human IgG1 subclass.

The term 'full length IgG' according to the invention is defined as comprising an essentially complete IgG, which however does not necessarily have all functions of an intact IgG. For the avoidance of doubt, a full length IgG contains two heavy and two light chains. Each chain contains constant (C) and variable (V) regions, which can be broken down into domains designated CH1, CH2, CH3, VH, and CL, VL. An IgG antibody binds to antigen via the variable region domains contained in the Fab portion, and after binding can interact with molecules and cells of the immune system through the constant domains, mostly through the Fc portion. The terms 'variable region domain', 'variable region', 'variable domain', 'VH/VL pair', 'VH/VL', 'Fab portion', 'Fab arm', 'Fab' or 'arm' are used herein interchangeably. Full length antibodies according to the invention encompass IgG molecules wherein mutations may be present that provide desired characteristics. Such mutations should not be deletions of substantial portions of any of the regions. However, IgG molecules wherein one or several amino acid residues are deleted, without essentially altering the binding characteristics of the resulting IgG molecule, are embraced within the term "full length IgG". For instance, such IgG molecules can have one or more deletions of between 1 and 10 amino acid residues, preferably in non-CDR regions, wherein the deleted amino acids are not essential for the binding specificity of the IgG.

Full length IgG antibodies are preferred because of their favourable half life and the need to stay as close to fully autologous (human) molecules for reasons of immunogenicity. According to the invention, bispecific IgG antibodies are used. In a preferred embodiment, bispecific full length IgG1 antibodies are used. IgG1 is favoured based on its long circulatory half life in man. In order to prevent any immunogenicity in humans it is preferred that the bispecific IgG antibody according to the invention is a human IgG1. The term 'bispecific' (bs) means that one arm of the antibody binds to a first antigen whereas the second arm binds to a second antigen, wherein said first and second antigens are not identical. According to the present invention, said first and second antigens are in fact two different molecules that are located on two different cell types. The term 'one arm [of the antibody]' preferably means one Fab portion of the full length IgG antibody. Bispecific antibodies that mediate cytotoxicity by recruiting and activating endogenous immune cells are an emerging class of next-generation antibody therapeutics. This can be achieved by combining antigen binding specificities for target cells (i.e., tumor cells) and effector cells (i.e., T cells, NK cells, and macrophages) in one molecule (Cui et al. JBC 2012 (287) 28206-28214; Kontermann, MABS 2012 (4) 182-197; Chames and Baty, MABS 2009 (1) 539-547; Moore et al. Blood 2011 (117) 4542-4551; Loffler et al. 2000 Blood 95:2098; Zeidler et al. 1999 J. Immunol. 163:1246). According to the invention, bispecific antibodies are provided wherein one arm binds the CLEC12A antigen on aberrant (tumor) cells whereas the second arm binds an antigen on immune effector cells.

Also contemplated are antibodies wherein a VH is capable of specifically recognizing a first antigen and the VL, paired with the VH in a immunoglobulin variable region, is capable of specifically recognizing a second antigen. The resulting VH/VL pair will bind either antigen 1 or antigen 2. Such so called "two-in-one antibodies", described in for instance WO 2008/027236, WO 2010/108127 and Schaefer et al (Cancer Cell 20, 472-486, October 2011), are also encompassed by the term "bispecific antibody" because they also have the capability of binding two different antigens. In one embodiment, a VH is used that specifically recognizes CLEC12A, or a functional equivalent thereof, and a VL is used that specifically recognizes an antigen on immune effector cells. Alternatively, an antibody according to the present invention comprises a VH that specifically recognizes an antigen on immune effector cells, and a VL that specifically recognizes CLEC12A, or a functional equivalent thereof. Either way, the resulting antibody typically contains two VH/VL pairs, wherein each VH/VL pair will bind either CLEC12A (or a functional equivalent thereof), or an antigen on immune effector cells. Two-in-one antibodies will typically either bind two similar antigens (AA or BB; monospecific bivalent) or bind two different antigens (AB; bispecific). Hence, if two-in-one antibodies are used for therapeutic applications according to the present invention, a portion of these antibodies will not exert the desired effect due to their binding to either two CLEC12A molecules (or functional equivalents thereof) or two antigens on immune effector cells, such as CD3. Since the therapeutic goal can still be achieved with a portion of the administered antibodies, two-in-one antibodies are nevertheless suitable.

The term 'CLEC12A' as used herein refers to C-type lectin domain family 12 member A, also known as C-type lectin-like molecule-1 (CLL-1; SEQ AID NO: 24), an antigen that is expressed on leukemic blast cells and on leukemic stem cells in acute myeloid leukemia (AML), including the CD34 negative or CD34 low expressing leukemic stem cells (side population) (A. B. Bakker et al. Cancer Res 2004, 64, p8443-50; Van Rhenen et al. 2007 Blood 110:2659; Moshaver et al. 2008 Stem Cells 26:3059). Expression of CLEC12A is otherwise restricted to the hematopoietic lineage, particularly to myeloid cells in peripheral blood and bone marrow, i.e., granulocytes, monocytes and dendritic cell precursors. More importantly, CLEC12A is absent on hematopoietic stem cells. This expression profile makes CLEC12A a particularly favorable target in AML. Alternative names for CLEC12A include dendritic cell-associated C-type lectin-2 (DCAL-2; SEQ ID NO: 23), myeloid inhibitory C-type lectin-like receptor (MICL) and killer cell lectin-like receptor subfamily L, member 1 (KLRL1; SEQ ID NO: 21) (Zhang W. et al. GenBank™ access. no: AF247788; A. S. Marshall, et al. J Biol Chem 2004, 279, p14792-802; GenBank™ access. no: AY498550; Y. Han et al. Blood 2004, 104, p2858-66; H. Floyd, et al. GenBank™ access. no: AY426759; C. H. Chen, et al. Blood 2006, 107, p1459-67). An alignment of these sequences is represented in FIG. 1 (SEQ ID NOs: 21-25). The full length form of CLEC12A comprises 275 amino acid residues, including an additional intracellular stretch of 10 amino acids which is absent in most other isoforms, and shows the strictly myeloid expression profile (surface expression and mRNA level). The term 'CLEC12A or functional equivalent thereof' means all variants that are referenced above and isoforms thereof that retain the strict myeloid expression profile (both at surface expression level and mRNA level) as described in Bakker et al. Cancer Res 2004, 64, p8443-50. Hence, the invention includes bispecific IgG antibodies wherein one arm specifically recognizes functional equivalents of CLEC12A, including those functional equivalents that lack the above mentioned additional intracellular stretch of 10 amino acids. Bispecific IgG antibodies according to the invention wherein one arm specifically recognizes the full length form of CLEC12A are, however, preferred.

The term 'aberrant cells' as used herein includes tumor cells, more specifically tumor cells of hematological origin including also pre-leukemic cells such as cells that cause myelodysplastic syndromes (MDS) and leukemic cells such as acute myeloid leukemia (AML) tumor cells or chronic myelogenous leukemia (CML) cells.

The term 'immune effector cell' or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte. According to the invention, recruitment of effector cells to aberrant cells means that immune effector cells are brought in close vicinity to the aberrant target cells cells such that the effector cells can directly kill, or indirectly initiate the killing of the aberrant cells that they are recruited to. In order to avoid non specific interactions it is preferred that the bispecific antibodies of the invention specifically recognize antigens on immune effector cells that are at least over-expressed by these immune effector cells compared to other cells in the body. Target antigens present on immune effector cells may include CD3, CD16, CD25, CD28, CD64, CD89, NKG2D and NKp46, Preferably, the antigen on immune effector cells is CD3 expressed on T cells, or a functional equivalent thereof (a functional equivalent would be a CD3-like molecule with a similar distribution on T-cells and a similar function (in kind, not necessarily in amount)). As used herein, the term "CD3" also encompasses functional equivalents of CD3. The most preferred antigen on an immune effector cell is the CD3ε chain. This antigen has been shown to be very effective in recruiting T cells to aberrant cells. Hence, a bispecific IgG antibody according to the present invention preferably contains one arm that specifically recognizes CD3ε.

Thus, the invention provides a bispecific full length IgG antibody, wherein said bispecific antibody comprises one arm that specifically recognizes CLEC12A or a functional equivalent thereof, and a second arm that specifically recognizes an antigen on immune effector cells capable of recruiting such cells to an aberrant cell expressing CLEC12A or said functional equivalent, wherein said immune effector cells comprise T cells. In another preferred embodiment, the invention provides a bispecific IgG antibody according to the invention wherein said antigen on said immune effector cells is CD3 or functional equivalent thereof, preferably human CD3ε. In another embodiment, the invention provides F(ab)'2 fragments of such bispecific IgG CLEC12A×CD3 antibody.

It is an aspect of the invention to provide a bispecific IgG antibody according to the invention wherein both arms comprise a common light chain. The term 'common light chain' according to the invention refers to light chains which may be identical or have some amino acid sequence differences while retaining the binding specificity of the antibody. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998, Nissim et al. 1994). Preferably, the common light chain has a germline sequence. A preferred germline sequence is a light chain variable region that is frequently used in the human repertoire and has superior ability to pair with many different VH regions, and has good thermodynamic stability, yield and solubility. A most preferred germline light chain is O12, preferably the rearranged germline human kappa light chain IgVκ1-39*01/IGJκ1*01 (nomenclature according to the IMGT database worldwide web at imgt.org or fragment or a functional derivative thereof. The terms rearranged germline human kappa light chain IgVκ1-39*01/IGJκ1*01, IGKV1-39/IGKJ1, huVκ1-39 light chain or in short huVκ1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions.

In a particularly preferred embodiment a bispecific IgG antibody according to the invention is provided wherein the arm that specifically recognizes CLEC12A or a functional equivalent thereof comprises a heavy chain CDR1 sequence consisting of a sequence that is at least 90% identical to SGYTFTSY (SEQ ID NO: 1) and a heavy chain CDR2 sequence consisting of a sequence that is at least 90% identical to IINPSGGS (SEQ ID NO: 2) and a heavy chain CDR3 sequence consisting of a sequence that is at least 90% identical to GTTGDWFD (SEQ ID NO: 3). Preferably, said heavy chain CDR 1, 2 and 3 sequences consist of a sequence that is at least 95%, more preferably at least 97%, more preferably at least 98%, more preferably at least 99% identical to the recited CDR sequences. Typically, variations of 1, 2 or 3 amino acid residues from the recited CDR sequences are allowed while retaining the same kind of binding activity (in kind, not necessarily in amount). Hence, said heavy chain CDR 1, 2 and 3 sequences preferably contain sequences that deviate in no more than three, preferably no more than two, more preferably no more than one amino acid from the recited CDR sequences. In a particularly preferred embodiment, said heavy chain CDR 1, 2 and 3 sequences are identical to the recited CDR sequences. The recited CDR sequences are the CDR sequences of Fab arm 4327 which, as shown in the Examples, has good CLEC12A binding properties. The heavy chain sequence of Fab arm 4327, hence the VH of CLEC12A-specific antibody 4327, is shown in FIG. 20. In one preferred embodiment, a bispecific IgG antibody according to the invention comprises a variable heavy chain (VH) sequence that is at least 90% identical to this VH of antibody 4327. Further provided is therefore a bispecific IgG antibody according to the invention, wherein the arm that specifically recognizes CLEC12A or a functional equivalent thereof comprises a VH sequence consisting of a sequence that is at least 90%, preferably at least 95%, more preferably at least 97%, more preferably at least 98%, more preferably at least 99% or even 100%, identical to the sequence QVQLVQSGAEVKKPGASVKVSCKAS-GYTFTSYYMHWVRQAPGQGLEWMGIINPSGGS TSYAQKFQGRVTMTRDTSTSTVYMELSSLRSED-TAVYYCAKGTTGDWFDYWGQGTLV TVS (SEQ ID NO: 4). As shown in the Examples, bispecific antibodies according to the invention containing the above mentioned VH sequence, together with a VH sequence of a Fab arm recognizing CD3 (and together with a common light chain), have an excellent capacity of inducing T cell mediated lysis of CLEC12A-positive AML tumor cells.

In a further preferred embodiment a bispecific IgG antibody according to the invention is provided wherein the arm that specifically recognizes CLEC12A or a functional equivalent thereof comprises a heavy chain CDR1 sequence consisting of a sequence that is at least 90% identical to SGYTFTSY (SEQ ID NO: 5) and a heavy chain CDR2 sequence consisting of a sequence that is at least 90% identical to IINPSGGS (SEQ ID NO: 6) and a heavy chain CDR3 sequence consisting of a sequence that is at least 90% identical to GNYGDEFDY (SEQ ID NO: 7). Preferably, said heavy chain CDR 1, 2 and 3 sequences consist of a sequence that is at least 95%, more preferably at least 97%, more preferably at least 98%, more preferably at least 99% identical to the recited CDR sequences. As stated above, typically variations of 1, 2 or 3 amino acid residues from the recited CDR sequences are allowed while retaining the same kind of binding activity (in kind, not necessarily in amount). Hence, said heavy chain CDR 1, 2 and 3 sequences preferably contain sequences that deviate in no more than three, preferably no more than two, more preferably no more than one amino acid from the recited CDR sequences. In a particularly preferred embodiment, said heavy chain CDR 1, 2 and 3 sequences are identical to the recited CDR sequences. The recited CDR sequences are the CDR sequences of the VH region of antibody 4331 which, as shown in the Examples, has good CLEC12A binding properties. The VH sequence of Fab arm 4331 is also shown in FIG. 20. In one preferred embodiment, a bispecific IgG antibody according to the invention comprises a VH sequence that is at least 90% identical to this VH of Fab arm 4331. Further provided is therefore a bispecific IgG antibody according to the invention, wherein the arm that specifically recognizes CLEC12A or a functional equivalent thereof comprises a VH sequence consisting of a sequence that is at least 90%, preferably at least 95%, more preferably at least 97%, more preferably at least 98%, more preferably at least 99% or even 100%, identical to the sequence EVQLVQS-GAEVKKPGASVKVSCKASGYTFTSYYMH-WVRQAPGQGLEWMGIINPSGGS TSYAQKFQGRVT-MTRDTSTSTVYMELSSLRSEDTAVYYCARGNYGDE FDYWGQGTLV TVSS (SEQ ID NO: 8). As shown in the Examples, bispecific antibodies according to the invention containing the VH sequence of Fab arm 4331, together with a VH sequence of a Fab arm recognizing CD3, (together with a common light chain) have an excellent capacity of inducing T cell mediated lysis of CLEC12A-positive AML tumor cells.

Yet another preferred embodiment provides a bispecific IgG antibody according to the invention wherein the arm that specifically recognizes CLEC12A or a functional equivalent thereof comprises a heavy chain CDR1 sequence consisting of a sequence that is at least 90% identical to SGYTFTGY (SEQ ID NO: 9) and a heavy chain CDR2 sequence consisting of a sequence that is at least 90% identical to WINPNSGG (SEQ ID NO: 10) and a heavy chain CDR3 sequence consisting of a sequence that is at least 90% identical to DGYFADAFDY (SEQ ID NO: 11). Preferably, said heavy chain CDR 1, 2 and 3 sequences consist of a sequence that is at least 95%, more preferably at least 97%, more preferably at least 98%, more preferably at least 99% identical to the recited CDR sequences. Again, typically variations of 1, 2 or 3 amino acid residues from the recited CDR sequences are allowed while retaining the same kind of binding activity (in kind, not necessarily in amount). Hence, said heavy chain CDR 1, 2 and 3 sequences preferably contain sequences that deviate in no more than three, preferably no more than two, more preferably no more than one amino acid from the recited CDR sequences. In a particularly preferred embodiment, said heavy chain CDR 1, 2 and 3 sequences are identical to the recited CDR sequences. The recited CDR sequences are the CDR sequences of the VH of antibody 3918 which, as shown in the Examples, also has good CLEC12A binding properties. The VH sequence of the antibody 3918 is also shown in FIG. 20. In one preferred embodiment, a bispecific IgG antibody according to the invention comprises a VH sequence that is at least 90% identical to this VH of antibody 3918. Further provided is therefore a bispecific IgG antibody according to the invention, wherein the arm that specifically recognizes CLEC12A or a functional equivalent thereof comprises a VH sequence consisting of a sequence that is at least 90%, preferably at least 95%, more preferably at least 97%, more preferably at least 98%, more preferably at least 99% or even 100%, identical to the sequence QVQLVQSGAEVK-KPGASVKVSCKASGYTFTGYYMHWVRQAPGQ-GLEWMGWINPSNG GTNYAQKFQGRVTMTRDTSIS-TAYMELSRLRSDDTAVYYCARDGYFADAFDYWGQ GT LVTVSS (SEQ ID NO: 12). As shown in the Examples, bispecific antibodies according to the invention containing the VH sequence of Fab arm 3918, together with the VH sequence of a Fab arm recognizing CD3, (and together with a common light chain) also have a good capacity of inducing T cell mediated lysis of CLEC12A-positive AML tumor cells.

In a further preferred embodiment a bispecific IgG antibody according to the invention is provided wherein the second arm specifically recognizes CD3 and comprises a heavy chain CDR1 sequence consisting of the sequence SYGMH (SEQ ID NO: 13) and a heavy chain CDR2 sequence consisting of the sequence IIWYSGSKKNYADS-VKG (SEQ ID NO: 14) and a heavy chain CDR3 sequence consisting of the sequence GTGYNWFDP (SEQ ID NO:

15). Preferably, said CD3-specific arm comprises a VH sequence consisting of the sequence QVQLVESGGGV-VQPGRSLRLSCAASGFTFRSYGMHWVRQAPGK-GLEWVAIIWYSGSK KNYADSVKGRFTISRDNSKNT-LYLQMNSLRAEDTAVYYCARGTGYNWFDPWGQGT LV TVSS (SEQ ID NO: 16). The recited CDR sequences and VH sequence are the sequences of antibody 3896. These sequences are also depicted in FIG. 20. A heavy chain comprising these CD3-specific CDR sequences and/or the recited VH sequence of Fab arm 3896 is preferred for a bispecific IgG antibody according to the invention, because these sequences provide the bispecific antibody with an optimal affinity for CD3-expressing immune cells, while simultaneously allowing sufficient binding to CLEC12A-positive AML tumor cells. Without wishing to be bound to theory, it is thought that the overall effect of a bispecific antibody is determined by the combined effect of the affinity of one arm for antigen 1 and the affinity of the other arm for antigen 2. For an antibody of the present invention, having a specificity for CLEC12A (or a functional equivalent thereof) and an antigen on immune effector cells (preferably CD3), an optimized timing of binding to CD3-positive immune cells and CLEC12A-expressing tumor cells is preferred in order to efficiently induce T cell mediated lysis of CLEC12A-positive tumor cells. It is hypothesized that the balance between affinities of a CLEC12A/CD3 bispecific antibody is of utmost importance. It is thought that a significantly higher affinity for CD3 versus a much lower affinity for CLEC12A (i.e., a too high affinity for CD3) will result in a situation wherein the antibodies would primarily bind CD3 expressing T cells. Such 'bispecific antibody-loaded' T-cells may either internalize their CD3 or may invade the tissues thereby leaving the circulation before they have even encountered a CLEC12A-positive tumor cell. This would diminish the therapeutic effect of the bispecific antibody.

In a more favorable mode of action, CLEC12A-positive tumor cells are first bound by one or more bispecific antibodies according to the invention, where after T cells are attracted by the free CD3 arm of the bispecific antibody and subsequent T cell activation takes place. Alternatively, CD3 positive T cells and CLEC12A-positive tumor cells are bound essentially simultaneously by the bispecific antibody. Hence, the affinities for both CLEC12A (or a functional equivalent thereof) and for an antigen on immune effector cells (preferably CD3) are preferably chosen or modulated such that the right balance is achieved, i.e. that the resulting bispecific antibodies will either bind CLEC12A and CD3 essentially simultaneously or that the bispecific antibodies have a tendency to bind CLEC12A-positive tumor cells to a sufficient extent, where after T cell activation takes place and the tumor cells are lysed. According to the present invention, such excellent balance between the binding affinities for CD3 and CLEC12A is preferably achieved by combining a VH having the CDR sequences (or whole VH sequence) of Fab arm 3896 (SEQ ID NO: 16) (which is specific for CD3) with a VH having the CDR sequences (or whole VH sequence) of either Fab arms 4327 (SEQ ID NO: 4) or 4331 (SEQ ID NO: 8) or 3918 (SEQ ID NO: 12) or 3116 (SEQ ID NO: 33) (which are specific for CLEC12A). Such resulting bispecific antibodies display a favorable balance between the binding affinities for CD3 and CLEC12A, so that T cells and CLEC12A-positive AML tumor cells are efficiently brought together, and T cell mediated lysis of CLEC12A-positive AML tumor cells is optimally induced.

As described herein before, a bispecific IgG antibody according to the present invention is preferably provided wherein both arms comprise a common light chain variable domain. A particularly preferred common light chain is the human rearranged kappa light chain IgVκ1-39*01/IgJκ1*01, also named O12. The nucleotide and amino acid sequence (SEQ ID NO: 28 and SEQ ID NO: 29) of the O12 VL are also depicted in FIG. 20. The CDR sequences are bold and underlined. A bispecific antibody according to the invention containing a common light chain that at least comprises the CDR sequences of O12 is therefore preferred. One aspect of the invention therefore provides a bispecific IgG antibody according to the invention, wherein the first and the second arms further comprise a light chain CDR1 sequence consisting of a sequence that is at least 90% identical to RASQSISSYLN (SEQ ID NO: 17) and a light chain CDR2 sequence consisting of a sequence that is at least 90% identical to AASSLQS (SEQ ID NO: 18) and a light chain CDR3 sequence consisting of a sequence that is at least 90% identical to QQSYSTPPT (SEQ ID NO: 19). Preferably, said light chain CDR 1, 2 and 3 sequences consist of a sequence that is at least 95%, more preferably at least 97%, more preferably at least 98%, more preferably at least 99% identical to the recited CDR sequences. Again, typically variations of 1, 2 or 3 amino acid residues from the recited CDR sequences are allowed. Hence, said light chain CDR 1, 2 and 3 sequences preferably contain sequences that deviate in no more than three, preferably no more than two, more preferably no more than one amino acid from the recited CDR sequences. In a particularly preferred embodiment, said light chain CDR 1, 2 and 3 sequences are identical to the recited CDR sequences. In one preferred embodiment, a bispecific IgG antibody according to the invention comprises a VL sequence that is at least 90% identical to the O12 VL chain. Further provided is therefore a bispecific IgG antibody according to the invention, wherein first and the second arms comprise a VL sequence consisting of a sequence that is at least 90%, preferably at least 95%, more preferably at least 97%, more preferably at least 98%, more preferably at least 99% or even 100%, identical to the sequence DIQMTQSPSSLSASVGDRVTIT-CRASQSISSYLNWYQQKPGKAPKLLIYAASSLQS-GVPSR FSGSGSGTDFTLTISSLQPEDFATYYCQQSYS-TPPTFGQGTKVEIK (SEQ ID NO: 20).

The term "% identical to" is defined herein as the percentage of residues in a candidate amino acid sequence that is identical with the residues in a reference sequence after aligning the two sequences and introducing gaps, if necessary, to achieve the maximum percent identity. Methods and computer programs for the alignment are well known in the art. One computer program which may be used or adapted for purposes of determining whether a candidate sequence falls within this definition is "Align 2", authored by Genentech, Inc., which was filed with user documentation in the United States Copyright Office, Washington, D.C. 20559, on Dec. 10, 1991.

A bispecific full length IgG antibody according to the invention by definition has two different antigen binding sites but the Fc region of the IgG also comprises a third binding site for an Fc receptor. If a cell carries both an Fc receptor and one of the targets of the bispecific antibody, cross-linking of the Fc receptor and said target on the surface of said cell may occur, which may lead to undesired effects. In a preferred embodiment the invention provides a bispecific full length IgG antibody according to the invention, wherein said bispecific IgG antibody has mutated lower hinge and/or CH2 domains such that interaction of said bispecific IgG antibody with Fc gamma (Fcγ) receptors is significantly reduced. As used herein, the term "such that interaction of said bispecific IgG antibody with Fc gamma receptors is significantly reduced" means that the capability of said bispecific IgG antibody of interacting with Fc gamma receptors, if such Fc gamma receptors are present in the vicinity of said antibody, is reduced. Thus, according to the invention a region of the antibody, preferably the lower hinge and/or the CH2 domain of the antibody is mutated (typically by expressing a mutated nucleic acid sequence encoding it) whereby the ability to interact with an Fc receptor is diminished. It is preferred that the interaction with the Fc receptor is essentially abolished. Amino acid residues in human IgG1 that are involved in binding to Fcγ receptors have been mapped previously. In addition to residues which, when altered, improved binding only to specific receptors or simultaneously improved binding to one type of receptor and reduced binding to another type, several residues were found that abrogated binding to one or more of the receptors (Shields R L et al. JBC 2001 (276) 6591-6604; Armour et al. Mol. Immunol. 2003 (40) 585-593). In a further preferred embodiment, said mutated lower hinge and/or CH2 domains comprise at least one substitution at amino acids positions 235 and/or 236 (numbering according to Kabat). Preferably, both amino acids positions 235 and 236 are substituted. It is shown in the examples that substitutions at these sites are capable of essentially preventing the interaction between the bispecific antibody and the Fc receptor present on the tumor cells. In particular it is shown that substitutions L235G and/or G236R are very suitable for that purpose. A bispecific IgG antibody according to the invention, wherein said mutated CH2 and/or lower hinge domains comprise substitution L235G and/or G236R, is therefore also provided herein. Preferably, both L235G and G236R are substituted. Alternatively, a person skilled in the art may introduce lower hinge and/or the CH2 domain mutations that comprise the substitutions 234F, 235E and/or 331S (Oganesyan et al. Biol. Crystall. 2008 (D64)700). Preferably, all three substitutions are introduced in this alternative.

In our U.S. provisional application 61/635,935, which has been followed up by US regular application Ser. No. 13/866,747 and PCT application No. PCT/NL2013/050294, (incorporated herein by reference), we disclose methods and means for producing bispecific antibodies from a single cell, whereby means are provided that favor the formation of bispecific antibodies over the formation of monospecific antibodies. These methods can also be favorably employed in the present invention. Thus the invention provides a method for producing a bispecific full length IgG antibody according to the invention from a single cell, wherein said bispecific full length IgG antibody comprises two CH3 domains that are capable of forming an interface, said method comprising providing in said cell a) a first nucleic acid molecule encoding a 1st CH3 domain-comprising polypeptide chain, b) a second nucleic acid molecule encoding a 2nd CH3 domain-comprising polypeptide chain, wherein said nucleic acid molecules are provided with means for preferential pairing of said 1st and 2nd CH3 domain-comprising polypeptides, said method further comprising the step of culturing said host cell and allowing for expression of said two nucleic acid molecules and harvesting said bispecific full length IgG antibody from the culture. Said first and second nucleic acid molecules may be part of the same vector or gene delivery vehicle and may be integrated at the same site of the host cell's genome. Alternatively, said first and second nucleic acid molecules are separately provided to said cell.

A preferred embodiment provides a method for producing a full length bispecific IgG antibody according to the invention from a single cell, wherein said bispecific IgG antibody comprises two CH3 domains that are capable of forming an interface, said method comprising providing:

a cell having a) a first nucleic acid sequence encoding a IgG heavy chain that specifically recognizes CLEC12A and that contains a 1st CH3 domain, and b) a second nucleic acid sequence encoding a IgG heavy chain that specifically recognizes an antigen on immune effector cells, preferably CD3, and that contains a 2nd CH3 domain, wherein said nucleic acid sequences are provided with means for preferential pairing of said 1st and 2nd CH3 domains, said method further comprising the step of culturing said cell and allowing for expression of said two nucleic acid sequences and harvesting said bispecific IgG antibody from the culture. In a particularly preferred embodiment, said cell also has a third nucleic acid sequence encoding a common light chain. A preferred common light chain is O12, preferably the rearranged germline human kappa light chain IgVκ1-39*01/IGJκ1*01, as described above. The preferred mutations to produce essentially only bispecific full length IgG molecules are the amino acid substitutions L351K and T366K (numbering according to Kabat) in the first CH3 domain and the amino acid substitutions L351D and L368E in the second CH3 domain, or vice versa. Further provided is therefore a method according to the invention for producing a bispecific IgG1 antibody, wherein said first CH3 domain comprises the amino acid substitutions L351K and T366K (numbering according to Kabat) and wherein said second CH3 domain comprises the amino acid substitutions L351D and L368E, said method further comprising the step of culturing said cell and allowing for expression of said nucleic acid sequences and harvesting said bispecific antibody from the culture. Also provided is a method according to the invention for producing a bispecific IgG1 antibody, wherein said first CH3 domain comprises the amino acid substitutions L351D and L368E (numbering according to Kabat) and wherein said second CH3 domain comprises the amino acid substitutions L351K and T366K, said method further comprising the step of culturing said cell and allowing for expression of said nucleic acid sequences and harvesting said bispecific antibody from the culture. Antibodies that can be produced by these methods are also part of the present invention.

The invention further provides a pharmaceutical composition comprising a bispecific IgG antibody according to the invention and a pharmaceutically acceptable carrier. As used herein, such 'pharmaceutically acceptable carrier' includes any and all solvents, salts, dispersion media, coatings, antibacterial and antifungal agents, isotonic and absorption delaying agents, and the like that are physiologically compatible. Depending on the route of administration (e.g., intravenously, subcutaneously, intra-articularly and the like) the active compound may be coated in a material to protect the compound from the action of acids and other natural conditions that may inactivate the compound.

The antibodies and pharmaceutical compositions according to the invention find their use in the treatment of various leukemias and pre-leukemic diseases of myeloid origin but also B cell lymphomas. Diseases that can be treated according to the invention include myeloid leukemias or pre-leukemic diseases such as AML, MDS and CML and Hodgkin's lymphomas and most non-Hodgkin's lymphomas. Thus the invention provides a bispecific full length IgG antibody according to the invention for use as a pharmaceutical in the treatment of myelodysplastic syndrome (MDS), chronic myelogenous leukemia (CML) or preferably acute myeloid leukemia (AML). Also provided is a use of a bispecific IgG antibody according to the invention in the preparation of a medicament for the treatment or prevention of myelodysplastic syndrome (MDS), chronic myelogenous leukemia (CML) or preferably acute myeloid leukemia (AML).

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred.

Approximately 30,000 patients are diagnosed each year with acute myeloid leukemia (AML) in Europe and US. The majority of these patients are 60 years of age or older. Older age is a major negative determinant of outcome in AML and long-term survival (at 5 years) of intensively treated older AML patients is approximately 10%. In almost all patients that have achieved remission upon induction chemotherapy, disease progression is observed within 3 years. Current post-remission treatment has shown limited, if any, value in older patients with AML. Therefore, a significant load of residual resistant leukemia remains, and the surviving subpopulation of drug-resistant leukemic cells rapidly generates recurrence. Novel types of drugs with entirely different modes of action are needed to target these chemotherapy non-responsive AML tumour cells in efforts to induce and sustain complete remissions. Although complete remission (CR) can be achieved with a number of intensive chemotherapy combinations in more than 50% of elderly AML patients and around 80% in younger patients, advancements of response or survival have remained a major investigational challenge. In a recently published network meta-analysis of 65 randomized clinical trials (15.110 patients) in older patients with AML most of the amended investigational induction regimens have similar or even worse efficacy profiles as compared to the conventional 3+7 induction regimen with daunorubicin and cytarabine. This standard treatment of AML is associated with high morbidity and even mortality. The majority of the patients in CR relapse due to remaining leukemic stem cells after chemotherapy. Further dose intensification is limited due to unacceptable toxicity. An urgent need for new treatment modalities preferably with less toxicity is thus emerging especially in elderly patients with AML.

Treatment of chemotherapy unresponsive AML could be achieved by engaging T cells from the patient's own immune system and AML tumour cells using a bispecific antibody. In this manner, the patients' immune system is strengthened and retargeted to attack and eradicate the AML tumour cells. The present invention provides CD3×CLEC12A bispecific IgG antibodies that efficiently induce AML tumour cell lysis. CD3×CLEC12A bispecific antibodies thus are a targeted therapy with fewer side effects that specifically eradicates leukemic stem cells in order to improve the prognosis of AML patients. Because CLEC12A is expressed on leukemic stem cells (LSC) and not on normal haematopoietic stem cells, therapy directed against this antigen (as has been shown in vitro) will eradicate the LSC while sparing the normal stem cell. It most probably will have the greatest impact in situations of Minimal Residual Disease (MRD). The expectancy is that relapse percentage will drop due to the eradication of the MRD. So the impact for the AML patient of this new treatment modality would be a less toxic treatment with a lesser percentage of relapse resulting in an improvement of outcome associated with a better quality of life. These full length IgG bispecific antibodies are clinically evaluated in relapsed AML patients. The clinical efficacy is analyzed using AML blast reduction in the bone marrow as an objective response criterion. An efficacious bispecific IgG for AML provides a novel therapeutic option for a large patient segment for which there is currently no treatment available. In addition to providing a means to achieve durable remissions, this treatment option also has a curative potential for AML when applied during remission.

EXAMPLES

Example 1: Generation and Functional Characterization of a Candidate CD3×CLEC12 Bispecific IgG1

To validate the concept of targeting an immune effector cell to an aberrant cell with a bispecific full length IgG, a candidate CD3×CLEC12A bispecific IgG1 was generated for which the CD3 and CLEC12A Fab arms were derived from antibodies previously described. In the CD3 Fab arm, the VH region from anti-CD3 antibody 15C3, one of the CD3-specific antibodies as disclosed in WO2005/118635, was used and this VH is referred to as '3056'. In the CLEC12A Fab arm, the VH region from scFv SC02-357, one of the CLEC12A-specific antibodies as disclosed in WO2005/000894, was used (hereafter named 'CLEC12A benchmark [Fab arm or antibody]'; alternatively this VH is referred to as '3116'). The nucleotide and amino acid sequences of the VH of the CD3 arm (3056) (SEQ ID NOS: 26 and 27), as well as the nucleotide and amino acid sequences of the VH of the CLEC12A arm (3116) (SEQ ID NOS: 32 and 33) of this candidate molecule, which is referred to as candidate 3056×3116, are provided in FIG. 20. The nucleotide and amino acid sequences of the common VL (huVκ1-39; 012) are also provided in FIG. 20 (SEQ ID NOS: 28 and 29).

The respective VH regions were cloned into expression vectors using methods known in the art for production of bispecific IgG1 (Gunasekaran et al. JBC 2010 (285) 19637-19646; WO2009/089004), in conjunction with the rearranged human IGKV1-39/IGKJ1 (huVκ1-39) light chain. The huVκ1-39 was previously shown to be able to pair with more than one heavy chain thereby giving rise to antibodies with diverse specificities, which facilitates the generation of bispecific molecules (De Wildt R M et al. J. Mol. Biol. 1999 (285) 895-901; De Kruif et al. J. Mol. Biol. 2009 (387) 548-58; WO2009/157771).

First, the binding of the candidate 3056×3116 CD3× CLEC12A bispecific IgG1 to CD3ε on HPB-ALL cells was demonstrated by flow cytometry, which was performed according to standard procedures known in the art (Table 1). Binding to cell-expressed CD3ε is confirmed using CHO cell transfected with CD3δ/ε or CD3γ/ε. The binding of the candidate 3056×3116 bispecific IgG1 to CLEC12A was determined using CHO cells transfected with a CLEC12A expression construct; CD3 monospecific antibody (3056×

3056) and CLEC12A monospecific antibody (3116×3116), as well as an irrelevant IgG1 isotype control mAb were taken as control.

TABLE 1

Binding to cell-expressed CD3 and CLEC12A by flow cytometry.

| IgG | HPB-ALL cells* | CLEC12A-transfected CHO cells* |
|---|---|---|
| candidate 3056x3116 CD3xCLEC12A | 6216 | 5299 |
| CD3 | 6899 | 282 |
| CLEC12A | 199 | 4147 |
| Isotype control | 34 | 289 |

*Results are given as the mean fluorescent intensity.

Affinity measurements of the candidate 3056×3116 bispecific IgG1 for CD3δ/ε and the extracellular domain of CLEC12A are determined by surface plasmon resonance (BIAcore). Briefly, purified recombinant antigens are covalently coupled to the surface of a CM5 sensor chip using free amine chemistry: antigens are diluted in a kAc buffer to 10 µg/ml and coupled to a surface that is activated with NHS/EDC (according to the manufacturer's recommendations). To determine the affinities of the Fab arms present in bispecific antibodies, these are serially diluted to 100, 50, 20, 10, 1 and 0.1 nM in Hepes buffered saline (HBS) and flowed over the antigen-coupled surface of the CM5 sensor chip at a high (30 µl/min) flow rate (to prevent re-binding). Flow cell 1 (FC1) is used as a control (blanc) surface and the responses (sensor grams) resulting from this surface are subtracted from the responses measured on other flow cells (FC). FC2 and FC3 are used for the two different antigens recognized by the bispecific antibody, to be able to measure the affinities of both Fab arms in a single kinetic run over all three surfaces. As the concentration of antibody does not significantly change when it is flowed over an antigen-coupled surface, the on-rates (that are concentration-dependent) of bispecific antibodies are simultaneously measured on the two different antigens they recognize. Sensorgrams of the association and dissociation phases of the different bispecific proteins are thus obtained. Using the BIA evaluation software and curve-fitting employing a 1:1 interaction model (for monovalent interaction), the affinities of the Fab arms are determined. In case the binding of the bispecific protein to the antigen-coated surface of the sensor chip is compromised (i.e., when very little protein binds, resulting in low responses and/or very fast off-rates), the setup of the experiment is reversed: the bispecific antibody is covalently coupled to the surface of the sensor chip using free amine chemistry and recombinant purified antigen is flowed over the surface at a high (30 µl/min) flow rate to measure the affinity of the Fab arm directed to that antigen.

Next, the functionality of the candidate 3056×3116 CD3× CLEC12A bispecific Ig was tested. First, the T-cell stimulatory capacity was investigated with healthy donor resting T-cells. Briefly, peripheral blood was obtained from healthy donors after informed consent. T-cells were isolated by standard density gradient isolation to enrich for peripheral blood mononuclear cells (PBMC), followed by negative selection using magnetic beads (pan T-cell kit, Miltenyi Biotec, cat. no. 130-091-155). Using this purification strategy, T-cells were so-called 'untouched' (i.e., not stained by antibodies, so-called 'resting T cells') to limit the possibility of pre-activation. Purified resting T-cells were subsequently incubated with cells from the leukemia-derived HL60 cell line in 10% fetal bovine serum (FBS) or 10% normal human serum (HS) at an effector: target cell ratio of 10:1 for two days. Results were expressed as the percentage of CD69-positive or CD25-positive cells within the CD4-positive or CD8-positive T-cell population.

Both the bivalent CD3 IgG and the CD3xCLEC12A bispecific IgG efficiently induced upregulation of the T-cell activation markers CD69 and CD25 on CD4-positive and CD8-positive T-cells (FIG. 2). In the presence of FBS which did not block Fc receptors present on HL60 cells (Liesveld et al. 1988, J. Immunol. 140(5), pages 1527-1533), also the control bispecific molecule CD3× isotype control IgG was shown to induce T-cell activation. This effect was diminished in the presence of HS, suggesting that the observed T-cell activation by monovalent CD3 binding of the CD3× isotype control IgG was dependent on Fc cross-linking. However, T-cell activation induced by the candidate 3056× 3116 CD3xCLEC12A bispecific IgG was only partially dependent on Fc-interactions, as the potency to upregulate CD69 and CD25 was largely maintained in the presence of HS (FIG. 2). This indicated that the intrinsic potency of monovalent CD3 binding was sufficient to activate T-cells when the binding molecule bridged to the CLEC12A antigen on the HL60 target cells following binding with the other Fab arm.

To investigate whether the extent of T-cell activation by the candidate 3056×3116 CD3xCLEC12A bispecific IgG is sufficient to induce target cell lysis, the HL60 cells in this assay were labeled with carboxyfluorescein diacetate succimidyl ester (CFSE) and cocultured with T-cells at various effector: target cell ratios. After one, two or three days, surviving CFSE-positive HL60 cells were quantified by flow cytometry. Results were expressed as the percentage of specific lysis related to PBS.

Figure 3:
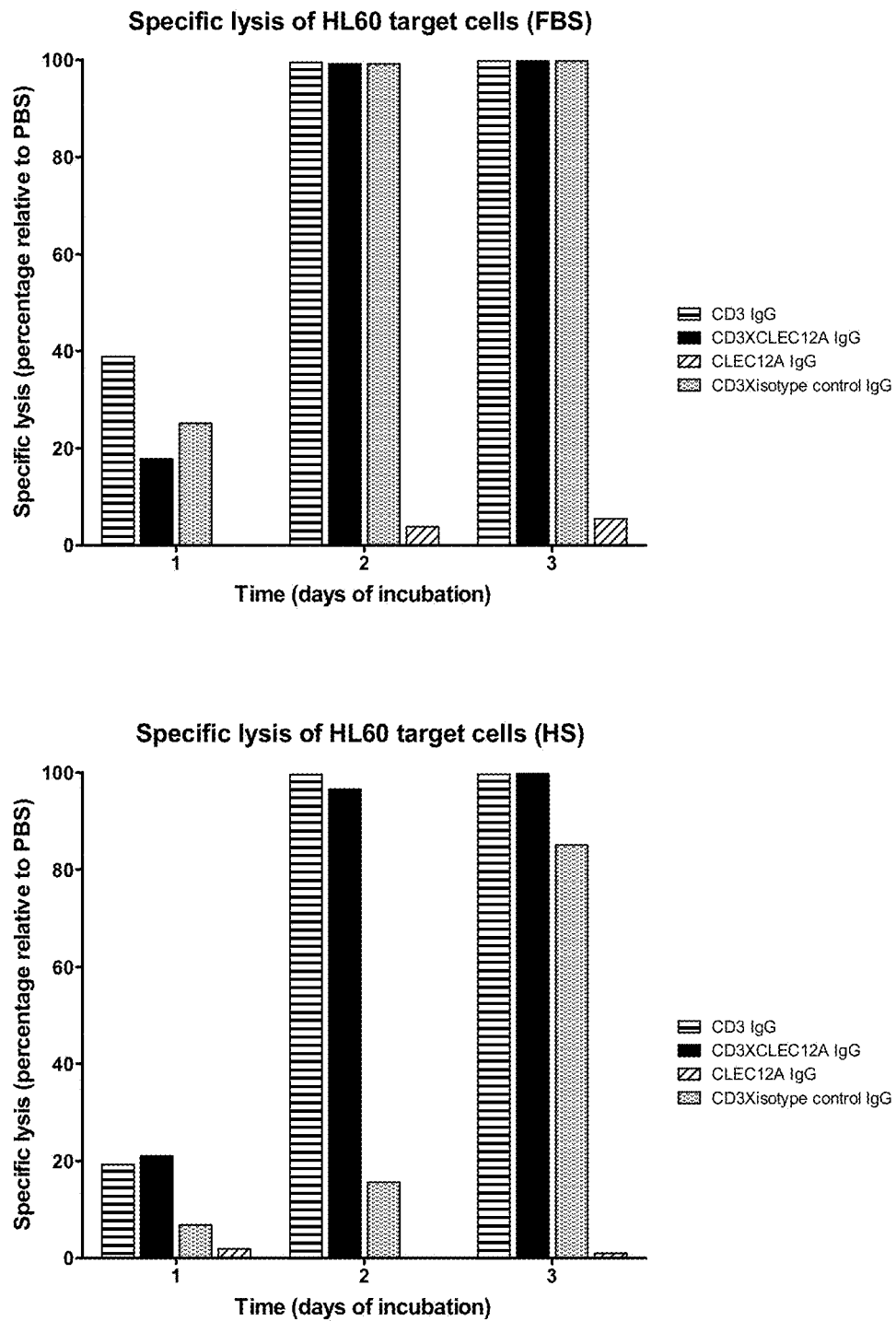
FIG. 3: Specific lysis of HL60 cells by CD3×CLEC12A bispecific IgG and control antibodies.
Figure 4:
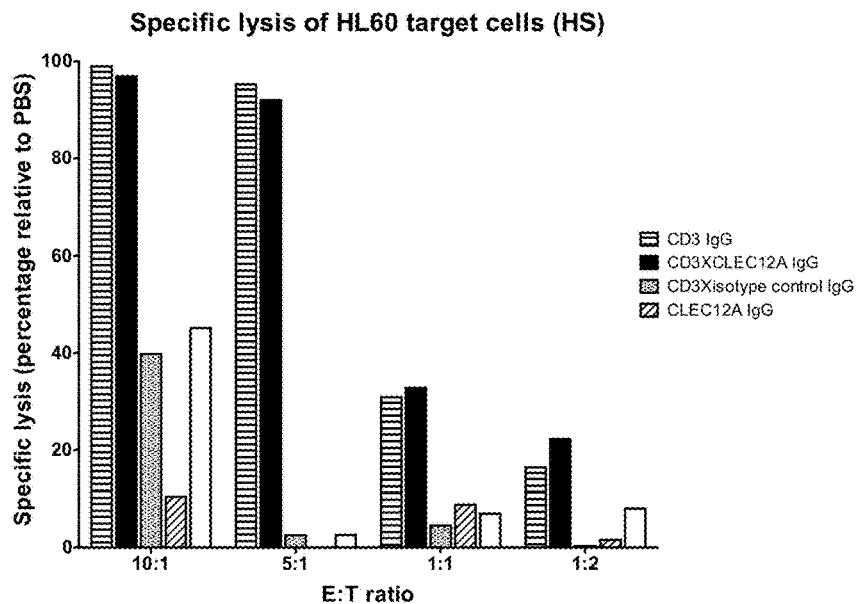
FIG. 4: Specific lysis of HL60 cells by CD3×CLEC12A bispecific IgG and control antibodies (E:T ratios).

As expected, CD3 monospecific bivalent IgG induced resting T-cell mediated killing of HL60 cells (FIG. 3). Surprisingly, CD3xCLEC12A bispecific monovalent IgG and the control CD3× isotype control also induced resting T-cell mediated killing of HL60 cells. These effects were most prominent when the assay was performed in the absence of excess of human IgG, i.e., when the Fc receptors on the HL60 target cells were not blocked (FBS condition; FIG. 3). Surprisingly, even in the presence of excess human IgG (10% HS condition) the CD3xCLEC12A bispecific IgG was very efficient in killing HL60 cells indicating that the induction of HL60 lysis is not dependent on Fcγ receptor interactions. On day 3 also HL60 lysis induced by the CD3× isotype control was observed, probably due to incomplete Fc-gamma receptor blockade upon extended incubation periods. HL60 target cell killing varied with different effector: target cell ratios (FIG. 4).

In conclusion, this example demonstrates that a CD3× CLEC12A bispecific molecule is a potent inducer of T-cell mediated tumor cell lysis and confirms our hypothesis that T cell engagement for effective killing of aberrant cells can be mediated by a CD3xCLEC12A full length IgG1 bispecific antibody. Surprisingly, the activity induced by the CD3xCLEC12A bispecific IgG is not dependent on Fcγ receptor interactions. To extend the panel of CD3× CLEC12A bispecific full length IgG in order to arrive at a final clinical candidate, panels of CD3 Fab arms and CLEC12A Fab arms are generated. Validation of specificity and functionality of CD3 and CLEC12A Fab arms is done by fixing the other arm using the respective Fab from the candidate 3056×3116 CD3xCLEC12A bispecific IgG shown in the current example.

Example 2: Generation and Characterization of CD3 Fab Arms for CD3×CLEC12 bsAb Example 1 showed that CD3×CLEC12A bispecific molecules can be potent inducers of T-cell mediated tumor cell lysis. Therefore, to generate more extensive panels of such bispecific molecules separate panels of CD3 binders as well as CLEC12A binders were generated.

For generation of a panel of CD3 binders, CD3ε-specific VH regions are generated by immunization of mice transgenic for the huVκ1-39 light chain (WO2009/157771) and for a human heavy chain (HC) minilocus with CD3ε in various formats: (1) isolated CD3δ/ε or CD3γ/ε that may be fused of coupled to a carrier molecule (such as human IgG-Fc or a His-tag) as known in the art with or without adjuvant, (2) cells expressing CD3δ/ε or CD3γ/ε, or (3) DNA construct encoding CD3δ/ε or CD3γ/ε, or a combination of these strategies. From immunized mice displaying a sufficient antigen-specific titer as determined by ELISA and/or flow cytometry, spleens and/or lymph nodes are harvested from which Fab phage libraries are generated. Alternatively, VH region sequences are derived directly from spleen and lymph node material by deep sequencing (U.S. provisional application 61/539,116).

Antigen-specific Fab arms are selected from phage libraries from immunized mice or from synthetic phage display libraries which contain the VL region of the huVκ1-39 light chain and a collection of human VH regions. For generation of synthetic libraries, randomized CDR3 primers were used as described in De Kruif et al. 1995, J Mol Biol 248(1), pages 97-105. Bacteriophages from these libraries are selected in multiple rounds for binding to isolated CD3δ/ε protein that may be coupled to a carrier molecule (see above) or to cells expressing CD3ε such as HPB-ALL or cells transfected to express CD3δ/ε or CD3γ/ε, or a combination of these strategies. Non-binding phages are removed and binding phages are eluted with an acidic buffer or, to direct the selected Fab repertoire to a desired specificity, with antibodies against a specific epitope, for example with antibodies that are cross-reactive to cynomolgous CD3ε. These phages are then transfected into competent bacteria which were grown under selection pressure for phage-containing bacteria. After picking a number of surviving bacterial colonies, phages are rescued and submitted to the next selection round.

After completing selection, the remaining phages are screened for binding to cell-expressed antigen by flow cytometry and to isolated antigen by ELISA. As a positive control for binding, benchmark CD3 antibodies are used such are known in the art, e.g., OKT-3. Nucleotide material from essentially all phages that showed specific binding to antigen-expressing cells is submitted to colony PCR to amplify the VH regions and sequence PCR to determine the VH region sequence. The resulting sequences are clustered based on uniqueness of their HCDR3. For sequences derived from immunized mice, in which (limited) somatic hypermutation can occur, VH sequences are further grouped based on the likelihood of a unique VDJ (i.e., if HCDR3 in different clusters contain <2 amino acids difference, they are considered part of the same cluster and are grouped together). From each cluster, one or a few VH regions per cluster are selected for cloning into vectors for expression in a IgG monospecific bivalent format in conjunction with the huVκ1-39 light chain. VH regions for which specific binding to isolated antigen and cell-expressed antigen is confirmed are subsequently cloned in vectors for expression in a CD3×CLEC12A bispecific format. These are then characterized to select a candidate with therapeutic potential (see following examples).

Example 3: Generation and Characterization of CLEC12 Fab Arms for CD3×CLEC12 bsAb As it was demonstrated in Example 1 that CD3×CLEC12A bispecific molecules have the potency to induce T-cell mediated tumor cell lysis, we next wished to establish more extensive panels of such bispecific molecules. In addition to the panel of CD3 binders as described in Example 2 we also generated a panel of CLEC12A binders.

Briefly, CLEC12A-specific Fab arms were selected from Fab synthetic phage display libraries which contained the rearranged human IGKV1-39/IGKJ1 VL region and a collection of human VH regions (De Kruif et al. Biotechnol Bioeng. 2010 (106)741-50). Bacteriophages from these banks were selected in two rounds for binding to CLEC12A. This was done by incubation with the extracellular domain of CLEC12A (amino acids 75 to 275) coupled to a His-tag (Sino Biological, cat. no. 11896-H07H) which was coated to a surface. Non-binding phages were removed, binding phages were chemically eluted, and used to infect bacteria which were grown under selection pressure for phage-containing bacteria. After picking a number of surviving bacterial colonies, phages were rescued and submitted to the next round of selection and propagation.

After completing selection, the remaining phages were screened for binding to CLEC12A expressed on the tumor cell line HL60 by flow cytometry. As a positive control for binding, the CLEC12A benchmark antibody was used. Nucleotide material from essentially all phages that showed specific binding to CLEC12A-expressing cells was submitted to colony PCR to amplify the VH regions and sequence PCR to determine the VH region sequence. The resulting sequences were clustered based on uniqueness of their HCDR3. The VH regions from each unique HCDR3 cluster were cloned into vectors for expression in IgG monospecific or bispecific formats in conjunction with the rearranged human IGKV1-39/IGKJ1 LC.

Three selected CLEC12A binding molecules with a unique HCDR3 sequence showed the desired profile in IgG format, which comprised the following characteristics (Table 2 and data not shown):

Specific binding to isolated extracellular domain of CLEC12A.

Specific binding to CLEC12A expressed on a tumor cell line.

Confirmation of myeloid lineage-specific expression pattern on human PBMC.

TABLE 2

Characterization of CLEC12A Fab arms.

| Fab | CDR3 length | Binding to coated CLEC12A* | Binding to CLEC12A-expressing cells** | Competition for epitope with CLEC12A benchmark*** |
|---|---|---|---|---|
| CLEC12A benchmark (SEQ ID NO: 33) | 9 | 1.422 | 1467 | — |
| 3918 (SEQ ID NO: 35) | 10 | 1.253 | 899 | Yes |

TABLE 2-continued

Characterization of CLEC12A Fab arms.

| Fab | CDR3 length | Binding to coated CLEC12A* | Binding to CLEC12A-expressing cells** | Competition for epitope with CLEC12A benchmark*** |
|---|---|---|---|---|
| 4327(SEQ ID NO: 37) | 9 | 1.307 | 1559 | No |
| 4331(SEQ ID NO: 39) | 9 | 1.328 | 1106 | Yes |

*Tested in ELISA, extracellular domain of CLEC12A (Sino Biological) coated at 2 µg/ml, results given as optical density (background signal isotype control: 0.127).
**Tested by flow cytometry on HL60 cells with optimized IgG concentration, results given as mean fluorescent intensity (background signal isotype control: 116).
***Tested in ELISA with Fab format, against bench mark IgG at 20 µg/ml.

Example 4: Selection of Functional CLEC12 Fab Arm for CD3×CLEC12 bsAb

Figure 5:
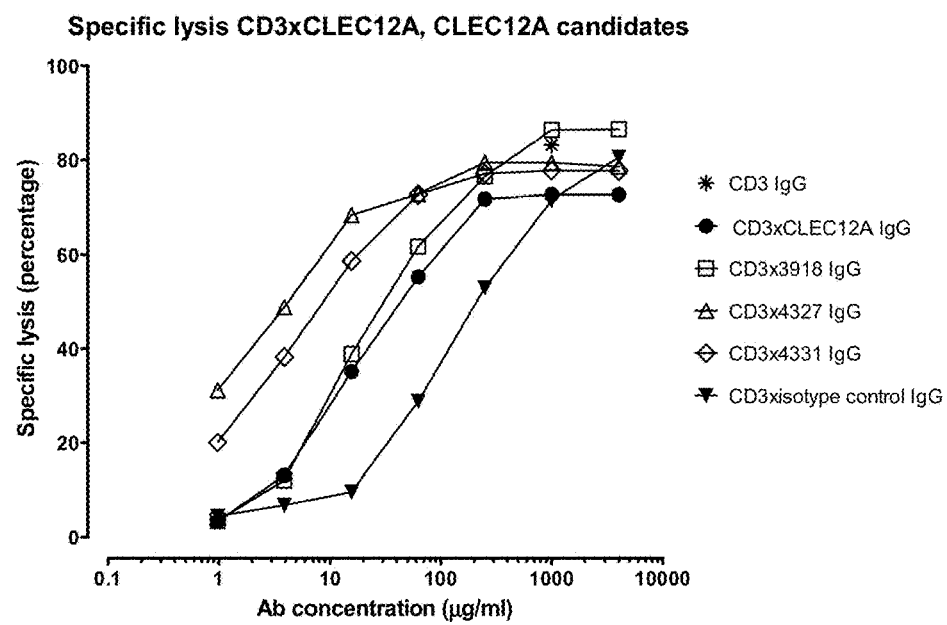
FIG. 5: Specific lysis of HL60 cells with several CD3× CLEC12A bispecific IgG molecules consisting of various CLEC12A arms & fixed CD3 arm, and control antibodies.

The selected CLEC12A Fab arms as described in Example 3 were subsequently expressed in bispecific IgG format with a new CD3 Fab arm as a fixed arm. This new CD3 Fab arm, referred to as '3896 CD3 IgG' or '3896' in short, also uses the huVκ1-39 light chain. The nucleotide and amino acid sequences of this CD3-specific VH candidate 3896 are depicted in FIG. 20 (SEQ ID NOs: 30 and 31, respectively). Hence, various bispecific CD3×CLEC12A molecules were expressed that all had the same 3896 (SEQ ID NO: 31) anti-CD3 arm but that differed in the CLEC12A arm, either the CLEC12A benchmark arm (SEQ ID NO: 33), or any one of the candidate CLEC12A Fab arms 4327 (SEQ ID NO: 37), 4331 (SEQ ID NO: 39) or 3918 (SEQ ID NO: 35). These CD3×CLEC12A bispecific molecules were then functionally tested in a target cell lysis assay as described in Example 1. Results were expressed as the percentage of specific lysis related to the isotype control. All candidate CLEC12A Fab arms showed a dose-dependent specific lysis of HL60 target cells in the bispecific format, with kinetics that were similar to or better than when the CLEC12A benchmark Fab arm used (FIG. 5).

Also, the CD3× isotype control bsAb showed a dose-dependent target cell lysis, although 1 log higher concentrations were required for the same extent of specific lysis. Despite the presence of excess human IgG via addition of HS, killing activity of this monovalent CD3 IgG was still apparent, probably by Fc-mediated cross-linking. As will be clear from Example 7, this target non-specific lysis can indeed be fully abrogated via silencing Fc receptor interaction by CH2 engineering.

Example 5: Efficacy of CD3×CLEC12 Product Candidates Using AML T Cells and/or AML Tumor Cells Examples 1 and 4 demonstrated the potency of CD3× CLEC12A bispecific IgG using either CD3 Fab arm 3056 (SEQ ID NO: 27) or 3896 (SEQ ID NO: 31) and using the CLEC12A Fab arm candidates 4327 (SEQ ID NO: 37), 4331 (SEQ ID NO: 39) or 3918 (SEQ ID NO: 35) or the CLEC12A benchmark Fab arm 3116 (SEQ ID NO: 33) in inducing HL60 target cell lysis mediated by healthy donor resting T-cells. In the current example, it is investigated whether T-cells derived from patients with AML, one of the primary indications for therapeutic application of a CD3× CLEC12A bispecific drug, can be stimulated to kill tumor targets upon stimulation with a CD3×CLEC12A bispecific full length IgG. Next, it is determined whether patient-derived T-cells can kill autologous AML tumor cell blasts upon stimulation with a CD3×CLEC12A bispecific full length IgG.

T-cells are isolated from peripheral blood of AML patients according to procedures as described in Example 1. Purified patient-derived T-cells are then incubated with CFSE-labeled HL60 cells and monitored for cell lysis as described in Example 1.

In addition, the T-cell mediated target cell lysis assay is performed with AML tumor blasts isolated from the same patient (Norde et al. Blood 2009 (113)2312). Isolated blasts are then labeled with CFSE and cocultured with autologous patient-derived T-cells in the presence of the cytokine mixture as described in Norde et al. and in the presence of the CD3×CLEC12A bispecific IgG or controls. Target cell lysis is monitored as described in Example 1.

Example 6: Cytokine Release by T Cells after Contact with CD3×CLEC12A Bispecific IgG Using T-cell stimulatory biologicals, overstimulation of T-cells is a serious risk as this may lead to cytokine release syndrome (Suntharalingam et al. 2006, New England J Med 355(10), pages 1018-1028; Chatenoud et al. 1990, Transplantation 49(4), pages 697-702). To investigate the extent of T-cell stimulation induced by CD3×CLEC12A bispecific IgG, the induction of T-cell cytokines was studied in a coculture of T-cells and Fc receptor-expressing target cells.

Briefly, healthy donor resting T-cells were cocultured with HL60 target cells in the presence of the candidate 3056× 3116 CD3×CLEC12A bispecific IgG (1 µg/ml) or control IgG as described in Example 1. After two days, the supernatant was sampled and cytokine production levels were determined in a Luminex assay as known in the art using the human Cytokine Human 10-Plex Panel (Invitrogen, cat. no. LHC0001). This panel covers the ten major Th1 and Th2 cytokines.

As expected, the CD3 monospecific bivalent IgG induced strong production of IFNγ, TNFα and IL-2 (Table 3), which are considered to mainly drive cytokine release syndrome. In addition, production of IL-4, IL-6, IL-8 and IL-10 was increased by incubation with CD3 IgG. In contrast, the CD3×CLEC12A bispecific IgG only induced IL-8 production to a similar level as CD3 IgG; the other cytokines were not significantly induced by the bispecific IgG. GM-CSF was below the detection limit in any condition.

TABLE 3 antibody induced cytokine release by T cells.

| Cytokine | CD3 IgG | CD3XCLEC12A IgG | CD3Xisotype control |
|---|---|---|---|
| IFNγ | 484.3 ± 155.0 | 13.5 ± 19.1 | 0.0 ± 0.0 |
| TNFα | 85.8 ± 23.1 | 14.5 ± 1.4 | 4.6 ± 1.1 |
| IL-2 | 285.6 ± 325.5 | 3.4 ± 0.8 | 1.7 ± 0.6 |
| IL-4 | 23.6 ± 3.7 | 10.2 ± 0.2 | 7.3 ± 1.3 |
| IL-6 | 9.0 ± 1.8 | 3.7 ± 0.3 | 2.3 ± 0.0 |
| IL-8 | 1567.8 ± 5.2 | 1280.1 ± 118.4 | 359.6 ± 183.6 |
| IL-10 | 531.5 ± 224.0 | 21.1 ± 3.0 | 3.7 ± 4.0 |
| IL-1β | 4.4 ± 0.4 | 3.3 ± 0.1 | 2.5 ± 0.1 |
| IL-5 | 2.1 ± 0.2 | 0.7 ± 0.0 | 0.6 ± 0.1 |

Results are given as the average concentration of cytokine in pg/ml of two donor ± standard deviation.

The data shown here suggest a favorable therapeutic profile for the different CD3×CLEC12A bispecific IgG molecules, as they potently induce target cell lysis (Examples 1 and 4) without triggering T-cells to secrete potentially harmful amounts of pro-inflammatory cytokines as observed with CD3 IgG.

Example 7: Effect of Fc Silencing on In Vitro Efficacy of CD3×CLEC12A bsAb

The dose-dependent target cell lysis by the CD3× isotype control bsAb shown in Example 4 was suggested to be due to interaction of the bsAb Fc part with Fc receptors on HL60 target cells. As such target non-specific cell lysis may als occur in vivo, either by interaction with Fc receptors on target cells or on bystander cells such as NK cells, engineering of the CH2/lower hinge region was employed to induce silencing of Fc-mediated activity of the bsAb.

For this, two Fc mutation strategies were examined, using either a 235G 236R double mutation (DM; DM-Fc) or a 234F 235E 331S triple mutation (TM; TM-Fc). CD3× CLEC12A bsAbs (3056×3116) with either a DM-Fc or a TM-Fc were generated and confirmed to bind CLEC12A-expressing cells by flow cytometry with the same intensity as the bsAb with wild type Fc (data not shown). Next, these bsAbs and the wild type, DM-Fc and TM-Fc versions of the CD3× isotype control bsAb were tested in the HL60 target cell lysis assay (see Examples 1 and 4). Results were expressed as the percentage of specific lysis related to the isotype control.

Figure 6:
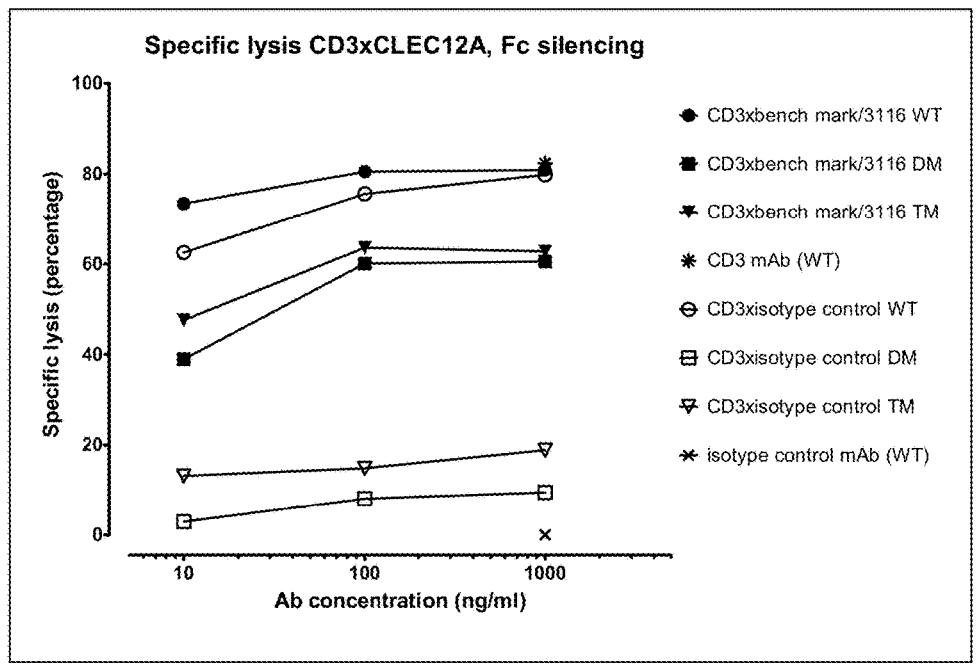
FIG. 6: Specific lysis of HL60 cells with CD3×CLEC12A bispecific IgG in combination with Fc silencing (DM=Double mutant; TM=triple mutant; WT=wildtype, no Fc silencing).

Fc silencing either by the DM or by the TM had no or only a minor influence on the extent of HL60 cell specific lysis induced by CD3×CLEC12A bsAb (FIG. 6). For the CD3× isotype control bsAb, however, the potency to induce lysis of HL60 cells was significantly reduced with the TM and even further with the DM.

This demonstrates that Fc silencing by CH2/lower hinge engineering further contributes to target-specific killing of aberrant cells by creating a bispecific CD3×CLEC12A IgG1 format that efficiently and specifically recruits effector cells, and diminishes the potential non-specific immune activation mediated by normal Fcγ receptor expressing accessory cells.

Figure 7:
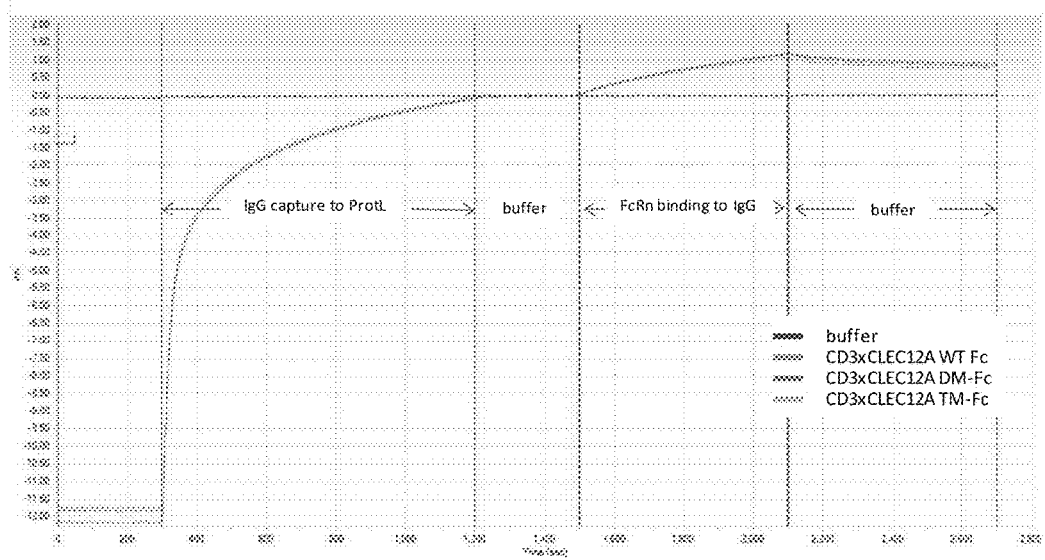
FIG. 7: Fc silencing does not affect FcRn binding.

Example 8: Effect of Fc-Silencing on Binding to FcRn, CD16, CD32, CD64 and C1q Binding of the candidate 3056×3116 CD3×CLEC12A bsAb with WT Fc or with silenced DM-Fc or a TM-Fc to human FcRn was determined by Bio-Layer Interferometry (BLI, Octet QK, ForteBio). Briefly, purified CD3× CLEC12A WT Fc IgG1, DM-Fc IgG1 or TM-Fc IgG1 was captured to Protein L biosensors (ForteBio, Cat no 18-5085) at a concentration of 50 µg/ml in 0.1 M phosphate buffer/ 0.002% Tween20 containing 1.0 mg/ml BSA pH6.0 (FcRn-Binding buffer) at RT. Subsequently soluble human FcRn (Sino Biological Inc, CT009-H08H) was added at concentration of 1 µg/ml in FcRn-Binding buffer) at RT. Data analysis using the Octet QK analysis software showed upon normalization for IgG binding to the ProtL sensor that the subsequent binding of CD3×CLEC12A bsAb with DM or TM silenced Fc to human FcRn was comparable to CD3× CLEC12A bsAb with wild-type Fc-tail (FIG. 7) and Fc silencing did thus not affect FcRn binding.

Binding of CD3×CLEC12A bsAb with silenced Fc to CD16, CD32 and CD64 is determined by Bio-Layer Interferometry (BLI, Octet QK, ForteBio). Protocol in short: purified CD3×CLEC12A WT Fc IgG1, DM-Fc IgG1 or TM-Fc IgG1 is captured to Protein L biosensors (ForteBio, Cat no 18-5085) at a concentration of 50 µg/ml in 1× Kinetics Buffer (ForteBio 18-5032) at RT. Subsequently recombinant CD16 (Sino Biological Inc, 10389-H08H1), CD32 (Sino Biological Inc, 10374-H08H) and CD64 (Sino Biological Inc, 10256-H08H) protein is added at concentration of 1.0 µg/ml in Kinetics Buffer (ForteBio 18-5032) at RT. Binding of FcR receptors to bsAb is analyzed using Octet QK analysis software.

Binding of CD3×CLEC12A bsAb with silenced Fc to human C1q is determined by capture ELISA. To this end purified CD3×CLEC12A WT Fc IgG1, DM-Fc IgG1 or TM-Fc IgG1 is coated in a concentration range of 25-0.012 µg/ml in PBS on Nunc-Immuno maxisorp F96 plate (Nunc, 439454) O/N at 4 C. Subsequently human C1q (Quidel, A400) is added at 2.0 µg/ml in ELISA buffer (2% MILK/ PBST). The complex is then visualized using sheep-anti-human C1q polyclonal IgG (Meridian, K90020C) and rabbit-anti-sheep HRP conjugated polyclonal IgG (Southern Biotech, 6150-05). Finally, using TMB substrate (BD 51-2606KC/51-2607KC) binding is developed and OD450 is quantified using a Micro plate reader (Multiskan EX, Thermo Electron Corporation).

Example 9: Evaluation of In Vivo Efficacy of CD3×CLEC12A Bispecific IgG

Animal xenograft studies using luciferase expressing HL60 cells (HL60(-Luc) cells) are performed to confirm and extend the in vitro findings using the CD3×CLEC12A bispecific IgG1. More specifically these studies are performed to determine the steady state plasma concentrations at effective doses, which will be taken into account in setting the starting dose for the Phase 1 clinical evaluation. To this purpose NOD/SCID mice (or comparable immune-compromised mice) are injected subcutaneously with an amount of viable HL60(-Luc) cells that results in the establishment of subcutaneous HL60 tumors in the majority of the animals within two weeks upon injection. In parallel with the HL60 (Luc) inoculation, or upon initial tumor take, $5×10^6$ or $1×10^7$ human PBMC are administered. CD3×CLEC12A bispecific IgG or control monospecific or control bispecific IgG are administered intravenously at several dose levels at the first day of PBMC administration, and 3, 6, and 9 days later. Tumor dimensions are scored 1 week after the initial HL60 (Luc) inoculation. The arithmetic average of tumor dimensions (either denoted as tumor volumes or as total bioluminescence) from each group is plotted against time.

Example 10: Use of a Bispecific Full Length IgG1 Antibody CD3×CLEC12A in a Phase Ia/Ib Study The final lead CD3×CLEC12A bispecific full length IgG1 candidate is used to manufacture GMP grade material and is clinically evaluated in AML patients. First, a formal non-clinical safety analysis of the product candidate is performed to establish a safe starting dose for first in man studies. Hereafter, an open-label, multi-centre dose escalation Phase Ia/b trial is performed in relapsed and/or refractory AML and in patients unfit for intensive treatment, to explore the safety and tolerability of the CD3×CLEC12A bispecific IgG upon i.v. administration. Secondary endpoints include pharmacokinetic and pharmacodynamic characterization and preliminary efficacy analysis. Overall response rates are assessed by evaluation of the AML blast reduction in the bone marrow. In Phase Ia the maximum tolerated dose (MTD) is assessed upon single/multiple dose escalation. After interim PK analysis, the Phase 1b part of the study

Example 11: Capacity of CD3×CLEC12A bsAb to Induce T Cell Proliferation

In patients with AML T cell numbers are low compared to the amount of AML blasts at diagnosis. It is well known that T cells undergo proliferation upon activation resulting in an increased number of T cells. Moreover, in example 1 we have demonstrated that a CD3×CLEC12A bsAb can activate T cells and has the potency to induce T-cell mediated tumor cell lysis. We hypothesized that AML patients treated with CD3×CLEC12A bsAb benefit from expansion of T cell subsets upon CD3×CLEC12A bispecific molecule mediated T cell activation as T cell proliferation will result in an increased number of effector T cells. To demonstrate that CD3×CLEC12A bsAb induces in vitro T cell proliferation, resting T cells were purified, labeled with carboxyfluorescein diacetate succimidyl ester (CFSE) and co-cultured with autologous CLEC12A+ monocytes in the presence of CD3×CLEC12A bsAb or control Abs. To specifically investigate the CD3×CLEC12A induced T cell proliferation without non-specific Fcgamma activation CD3×CLEC12A bsAbs with the DM-Fc tail, as described in Examples 7 and 8, was used. As controls, a CD3× isotype control WT-Fc bsAb, a CD3× isotype control DM-Fc bsAb, a monoclonal CD3 with WT-Fc and an irrelevant isotype control (IgG with WT-FC) were included. Monocytes and T cells from healthy donor peripheral blood were isolated by standard density gradient isolation to enrich for peripheral blood mononuclear cells (PBMC), followed by a CD14 positive selection for monocytes using CD14 microbeads (human CD14 microbeads, Miltenyi Biotec, cat. no. 130-050-201) and a negative selection of untouched T cells using magnetic beads against other leukocytes (pan T-cell isolation kit, Miltenyi Biotec, cat. no. 130-096-535). The pan T-cell isolation kit allows isolation of resting (untouched) T cells (i.e. not stained with antibodies) avoiding the possibility of pre-activation of T cells.

CFSE-labeled purified resting T cells were subsequently incubated with purified monocytes and bsAbs in medium with 10% normal human serum (HS) at an effector: target cell ratio of 5:1 for seven days. At day 7 decrease of CFSE signal as read-out for T cell proliferation was measured by flow cytometry. Results were expressed CFSE signal per CD3+, CD3+CD4+ or CD3+CD8+ T cells in histograms.

Figure 8:
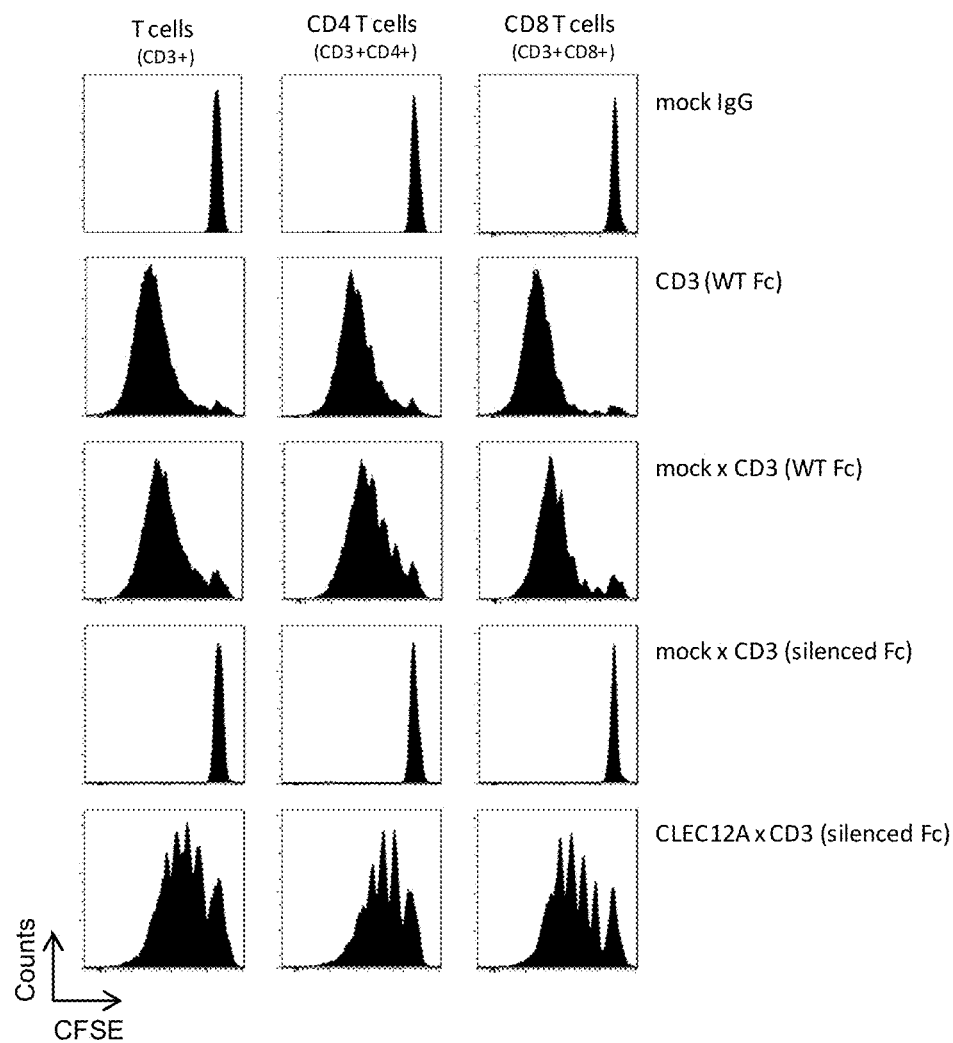
FIG. 8: CD3×CLEC12A bsAb target specific induction of T cell proliferation.

Positive control CD3 WT-Fc Ab induced T cell proliferation whereas isotype control IgG with WT-Fc did not induce T cell proliferation (FIG. 8). As expected the CD3× isotype control WT-Fc bsAb did induce T cell proliferation, but to a lower extend when compared to the bivalent monospecific anti-CD3 IgG control. In contrast, the CD3× isotype control DM-Fc bsAb did not induce T cell proliferation due to its silenced Fc-tail. The CD3×CLEC12A DM-Fc also induced the desired T cell proliferation mediated by specifically bridging CD3 with the CLEC12A antigen This shows that a CD3×CLEC12A bsAb is not only capable of target specific induction of T cell mediated tumor lysis as demonstrated previously, but can also potently induce target specific T cell proliferation resulting in an increased number of T cells. Moreover this further demonstrates that Fc silencing by CH2/lower hinge engineering not only contributes to target-specific killing of aberrant cells but also to target-specific induction of T cell proliferation by the CD3×CLEC12A DM-Fc bsAb IgG.

Example 12: Evaluation of CD3×CLEC12A Induced Expansion of $T_{EMRA}$ Subset from AML Patients As activation of T cell proliferation was demonstrated for CD3×CLEC12 DM-Fc bsAb, we next wished to investigate whether CD3×CLEC12A DM-Fc bsAb is capable of inducing proliferation of the CD8+ cytotoxic T cell compartment in AML patients. $CD8^+$ cytotoxic T cells have been recognized as the main effectors mediating tumor regression (Sluijter et al., 2010). CD8+ T cells can be divided into four subsets: naïve (CCR7+CD45RA+), central memory ($T_{CM}$, CCR7+CD45RA−), effector memory ($T_{EM}$, CCR7-CD45RA−), and CD45RA+ effector memory ($T_{EMRA}$, CCR7-CD45RA+) cells. Studies have shown that naive and memory CD8+ T-cell subsets have different capacities to proliferate and differentiate in response to TCR stimulation (Geginat et al., 2003).

First the CD8+ compartment in peripheral blood of AML patients in clinical remission was analyzed in comparison to healthy donors. To this end PBMC were isolated from frozen peripheral blood samples from AML patients and healthy donors by standard density gradient isolation. Next, PBMCs were stained with CCR7, CD3, CD4, CD8, CD45RA and CD45RO antibodies to analyze for the CD8+ T cell subsets by flow cytometry. Results were expressed as percentage of a subset in the total CD8+ T cell compartment.

Figure 9:
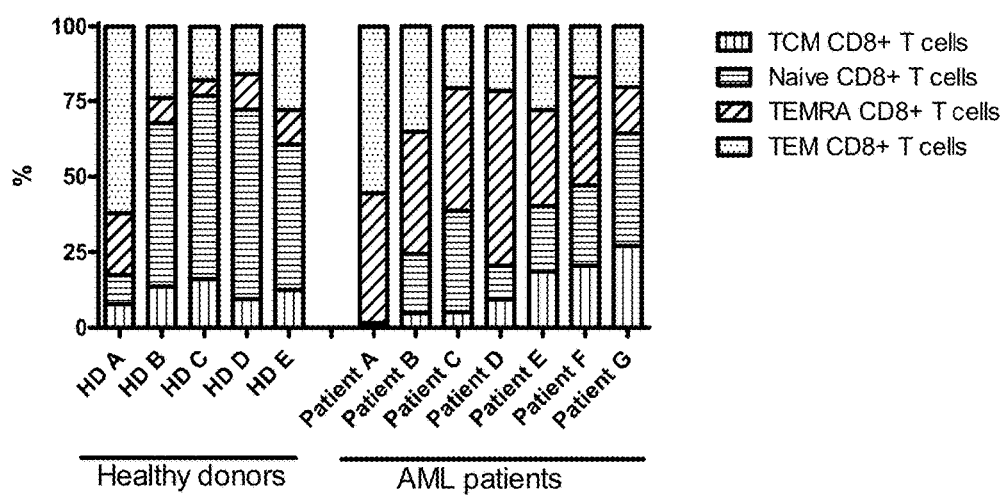
FIG. 9: CD8+ T cell compartment of AML patients compared to healthy donors.

Analogous to what was previously described, it was observed that the naïve CD8+ T cell subset was reduced in blood from AML patients compared to the naïve CD8+ T cell subset from healthy individuals, whereas the $T_{EMRA}$ compartment (CCR7-CD45RA+) was increased in AML patients compared to healthy donors (FIG. 9).

Next, experiments are performed to study tumor target specific T cell proliferation of the AML patient T cell compartment. More specifically, these experiments are performed to determine if the CD3×CLEC12A DM-Fc bsAb can enhance T cell proliferation and outgrowth of the effector T cell subsets ($T_{EM}$ and $T_{EMRA}$) of AML patients relative to the naïve CD8+ T cells of AML patients.

To this end resting T cells from AML patients in clinical remission are purified according to example 11. Composition of the CD8+ T cell subsets at day=0 is analyzed by staining of the PBMC with CCR7, CD3, CD4, CD8, CD45RA and CD45RO antibodies, followed by flow cytometric analysis. In addition, resting T cells are either labeled with CFSE or not labeled (CFSE labeling as described in example 11) and co-cultured with HL60 leukemia cells at an E:T ratio 5:1 with control or test antibodies for 7 days. CFSE labeled T cells are used for quantification of T cell proliferation, whereas unlabeled T cells are used to determine the percentage of proliferated T cell subsets. CFSE-labeled and unlabeled T cells are incubated with PBS, isotype control WT-Fc Ab, CD3×CLEC12A DM-Fc bsAb, CD3× isotype control DM-Fc bsAb and CD3 monoclonal Ab with WT-Fc at 1 µg/ml. After 7 days, CFSE labeled T cell are stained with CD3, CD4 and CD8 antibodies and subjected to FACS analysis to determine the absolute T cells numbers and number of cell divisions, whereas unlabelled CFSE T cells are stained with CCR7, CD3, CD4, CD8, CD45RA and CD45RO antibodies to determine composition of the proliferated CD8+ T cell subsets by flow cytometry. T cell proliferation is expressed as CFSE signal per T cell subset in histograms and the size of the four CD8+ T cells subsets is expressed as percentage within the total CD8+ T cell compartment.

Example 13: Efficacy of CD3×CLEC12A bsAb to Induce AML Patient T Cell Mediated Tumour Cell Lysis In example 1 it was demonstrated that a CD3×CLEC12A bsAb can induce killing of CLEC12A-positive HL60 cells by resting T cells from healthy donors. Next we investigated the capacity of the CD3×CLEC12A bsAb to induce target-specific activation of AML patient T cells and its capacity to induce AML patient T cell mediated killing of HL60 cells. T cells were isolated from frozen peripheral blood of AML patients (AML FAB classification AML-M1/M2, M4 or M5) in clinical remission using pan T-cell isolation kit as described in example 11. Purified AML patient derived resting T-cells were subsequently incubated with CSFE-labeled HL60 cells in medium supplemented with 10% normal HS at an effector: target cell ratio of 5:1 for two days, in the presence of PBS, isotype control WT-Fc Ab, CD3×CLEC12A DM-Fc, CD3× isotype DM-Fc, and positive control CD3 WT-Fc Ab (all antibodies at concentration of 1 µg/ml). After two days of co-culture, T cell activation was determined by flow cytometric analysis for CD3, CD4, and CD25. These results were expressed as percentage CD25+ cells per CD4+ T cells. Moreover, surviving CFSE-positive HL60 cells were quantified by flow cytometry. Results were expressed as the percentage of specific lysis relative to IgG.

Figure 10:
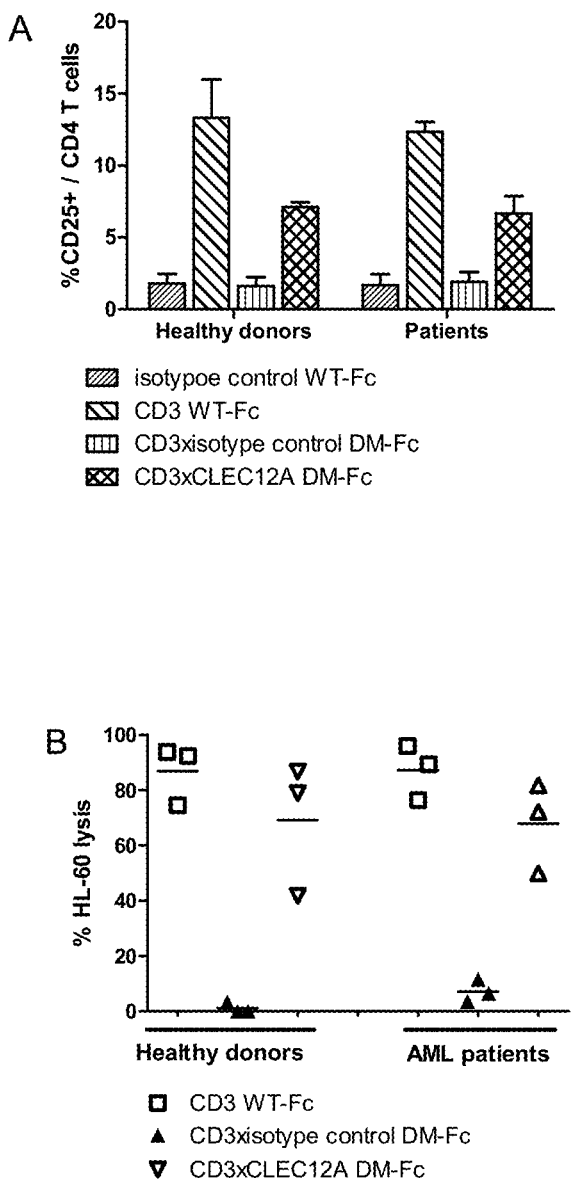
FIG. 10: Specific CD3×CLEC12A DM-Fc induced T cell activation and HL60 tumor cell lysis by AML patient T cells.

These data show that the antigen-specific activation of healthy donor and AML patient T cells mediated by CD3×CLEC12A DM-Fc bsAb was comparable (FIG. 10A). As expected the CD3× isotype control DM-Fc bsAb did not induce T cell activation of health donor nor AML patient derived T cells. It was demonstrated that the CD3×CLEC12A DM-Fc bsAb mediated lysis of HL60 cells by AML patient derived T-cells (68% HL60 cell lysis) was comparable to that by healthy donor T cells (69% HL60 cell lysis, FIG. 10B). As expected, the CD3× isotype control DM-Fc bsAb did not induce killing of HL60 cells, neither by AML patient T cells nor by healthy donor T cells. Thus, the CD3×CLEC12A bispecific molecule is a potent inducer of T cell mediated tumor cell lysis, regardless of whether these T cells are AML patient derived or from healthy donors.

As it was shown that the CD3×CLEC12A bsAb has the capacity to induce potent lysis of HL60 tumor cells by AML patient T cells, subsequently the capacity of the CD3×CLEC12A bsAb to target specific activation of AML T cells was evaluated. In addition, the capacity of the CD3×CLEC12A bsAb to induce lysis of primary CLEC12A-positive AML blasts by AML patient derived autologous T cells was determined. First, frozen stored bone marrow samples from AML patients at diagnosis samples containing >70% of primary AML blasts as determined by flow cytometric analysis were thawed, cultured overnight (O/N) in IMDM medium supplemented with 10% FCS, 100 ng/ml GM-CSF, 100 ng/ml G-CSF, 50 ng/ml IL-3, 25 ng/ml SCF and 20 ng/ml Flt3L as previously described (Norde et al., 2009). After O/N culture, primary AML blasts were phenotyped for surface expression of CLEC12A, CD3, CD4, CD8, CD14, CD19, CD33, CD34, CD38, CD45 and CD117 by flow cytometry and labelled with CFSE. Resting autologous patient derived T cells, collected when the patient had achieved clinical remission, were isolated from the peripheral blood using the pan T-cell isolation kit as described in example 11. Subsequently, AML blasts were co-cultured with resting autologous T cells at an E:T ratio of 5:1 in medium with 10% HS for two days. The conditions tested included PBS, isotype control Ab WT-Fc, CD3×CLEC12A DM-Fc, CD3× isotype control DM-Fc and positive control CD3 WT-Fc Ab (all antibodies at 1 µg/ml). After two days of co-culture, T cell activation was determined by flow cytometric analysis for CD3, CD4, CD8, and CD25. These results were expressed as percentage CD25+ cells per CD4+ or CD8+ AML T cells. AML blast lysis was determined by quantification of the surviving CFSE$^+$/CD45$^{low}$ double positive AML blasts by flow cytometry. Results were expressed as the percentage of specific blast lysis relative to IgG.

Figure 11:
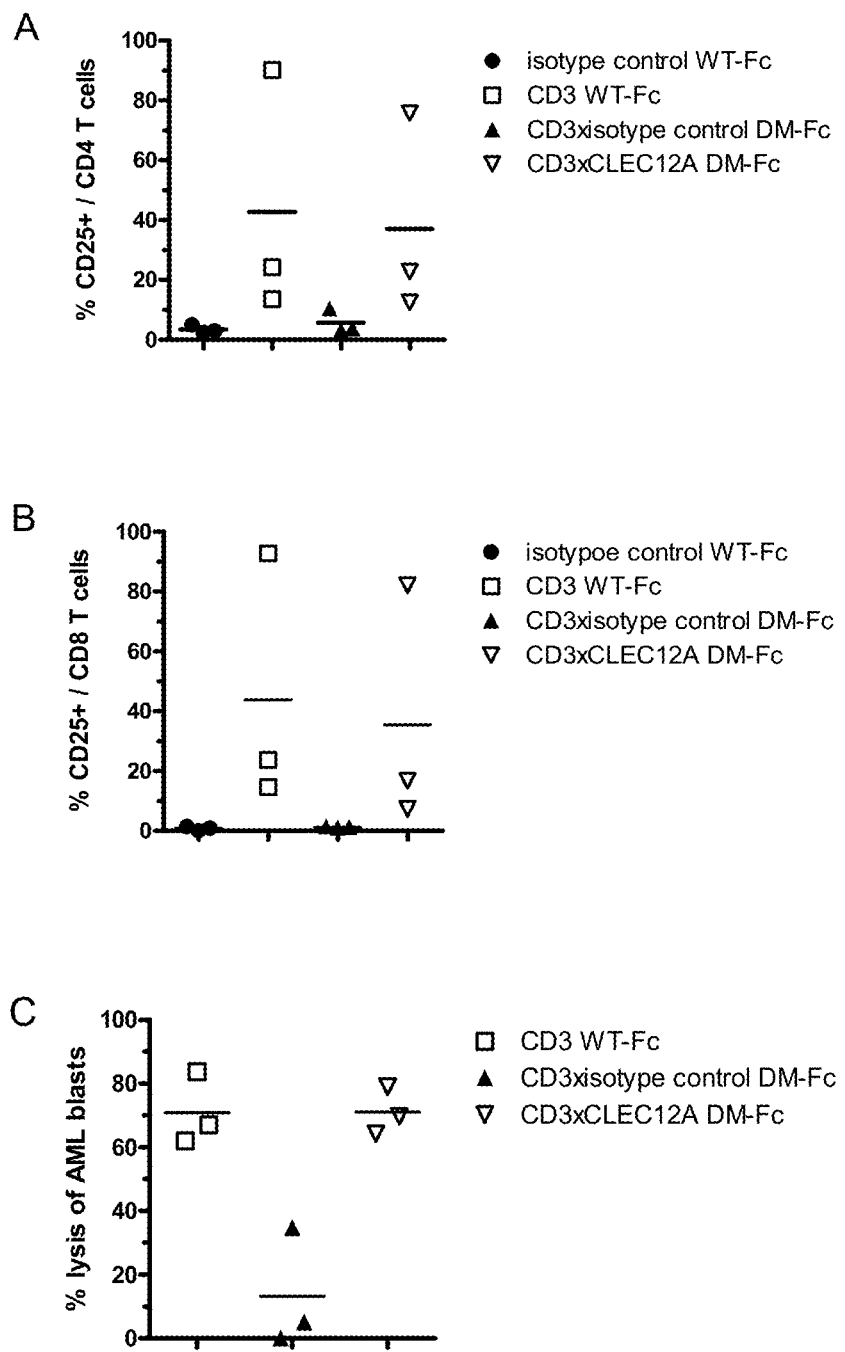
FIG. 11: Specific lysis of AML blasts by autologous AML patient T cells.

These data demonstrate that the CD3×CLEC12A DM-Fc bsAb has the capacity to induce AML blast target specific activation of AML T cells comparable to the monoclonal CD3 WT-Fc positive control Ab (FIG. 11A/B). Moreover these data demonstrate that the CD3×CLEC12A bsAb induced potent killing of autologous AML blasts by AML patient-derived T cells is as potent as the killing induced by the monoclonal CD3 WT-Fc positive control Ab (FIG. 11C). As expected, no or minor AML blast killing was induced by the CD3× isotype control DM-Fc Ab, which indicates that the observed AML blast killing mediated by the CD3×CLEC12A bsAb is primarily the result of antigen-specific activation of T cells and specific lysis of CLEC12A+ AML tumor cells. Overall, this study demonstrates that CD3×CLEC12A bsAb can efficiently induce killing of CLEC12A positive tumor cells by AML patient T cells.

Example 14: Effect of Fc-Silencing on Non-Specific Cytokine Release

In examples 7 and 8 it was demonstrated that CD3×CLEC12A bsAb IgG1 format with Fc silencing by CH2/lower hinge engineering (DM-Fc) resulted in reduced affinity for Fcgamma receptors and abrogated non-specific Fc receptor mediated cytotoxicity of the leukemia-derived HL60 cell line. Next, it was investigated whether the bsAb IgG1 format with DM-Fc silencing abrogated non-specific Fc receptor mediated cytotoxicity in the presence of Fc receptor-positive bystander cells such as NK cells. In this study, autologous healthy donor derived resting T cells were redirected against CLEC12A-positive monocytes in the presence of other Fc receptor positive bystander innate effector cells such as NK cells. To this end PBMC were isolated from heparinized peripheral blood from healthy donors by density gradient centrifugation and were plated at a density of 1×10$^6$ cells/ml. PBMC were cultured for two days in medium with 10% FBS in the presence of either PBS, isotype control Ab, CD3×CLEC12A WT-Fc bsAb, CD3×CLEC12A DM-Fc bsAb, CD3× isotype control WT-Fc bsAb, CD3× isotype control DM-Fc bsAb or CD3 monoclonal Ab with WT-Fc. After two days culture, surviving monocytes were quantified by flow cytometry based on CD14-expression. Results were expressed as the percentage of specific lysis related to IgG.

Figure 12:
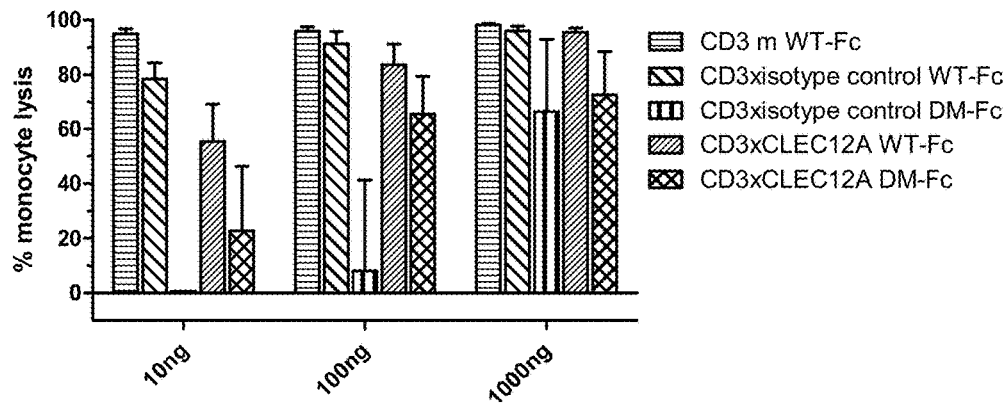
FIG. 12: Specific monocyte lysis by patient T cells.

It was demonstrated that, for the CD3×CLEC12A bispecific antibody, Fc silencing through the presence of the DM-Fc region only had a minor effect on monocytes lysis (FIG. 12). In contrast, for the CD3× isotype control bsAb, Fc silencing through the presence of the DM-Fc region significantly reduced the non-specific lysis of monocytes. It is thus concluded that Fc silencing in the CD3×CLEC12A bsAb further contributes to target-specific killing: the CD3×CLEC12A DM-Fc bsAb specifically recruits T cells and diminishes non-specific immune activation mediated by normal Fcγ receptor expressing accessory cells.

Next it was questioned whether the Fc silencing by the DM mutation in the CD3×CLEC12A bsAb abrogates the Fc receptor-mediated release of cytokines, known to be associated with cytokine release syndrome (CRS), a common clinical event with antibody therapies brought about by accessory cells. To this end the cytokine profile in the supernatants of the monocyte killing assay described in FIG. 13 was analyzed using the cytokine human 10-plex panel for the Luminex platform (Invitrogen, LHC0001) according to manufacturer instructions. The profile of the following human cytokines was measured in day 2 supernatant: GM-CSF, IFN-γ, IL-1β, IL-2, IL-4, IL-5, IL-6, IL-8, IL-10 and TNF-α. Results shown are of cytokine concentration measured in pg/ml. The levels of GM-CSF, IL-4 and IL-5 cytokines were below detection limit of this assay (data not shown).

Figure 13:
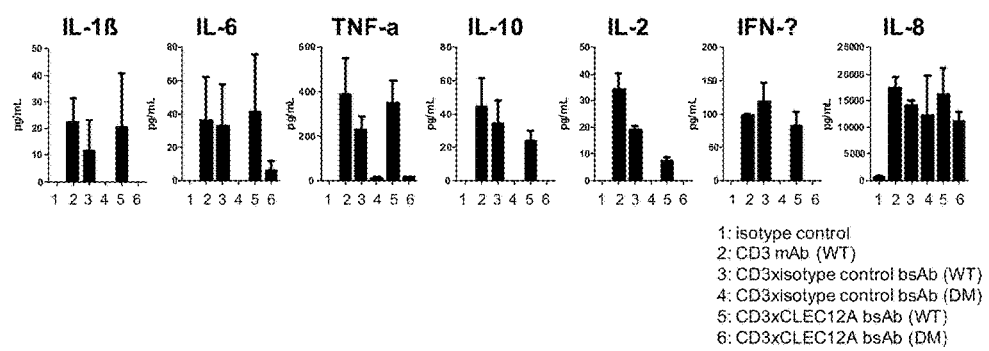
FIG. 13: Fc silencing significantly eliminates bystander cell cytokine release.

The data show that CD3×CLEC12A and CD3× isotype control bsAb, both with WT-Fc tail induced release of IL-1β, IL-6, TNF-α, IL-10, IL-2 and IFN-γ (FIG. 13). However, no or only very low levels of those cytokines were found in CD3×CLEC12A and CD3× isotype control bsAb when carrying the DM-Fc tail, with an exception for IL-8. As monocytes are the main source of IL-8, the high IL-8 levels are assumed to be released from the lysed monocytes and are not a result from a-specific FcR mediated release. It is concluded that Fc silencing through the DM mutations in the bsAb IgG format significantly eliminates the Fc receptor mediated release of IL-1b, IL-6, TNF-α, IL-2 and IFN-γ cytokines associated with CRS. Overall, these data demonstrate that the Fc silencing by the DM mutation in the CH2/lower hinge region contributes to the enhancement of the efficiency and specific recruitment of effector cells by CD3×CLEC12A DM-bsAb by diminishing the potential non-specific immune activation mediated by normal Fcγ receptor expressing accessory cells and associated release of proinflammatory cytokines.

Example 15

Figure 14A:
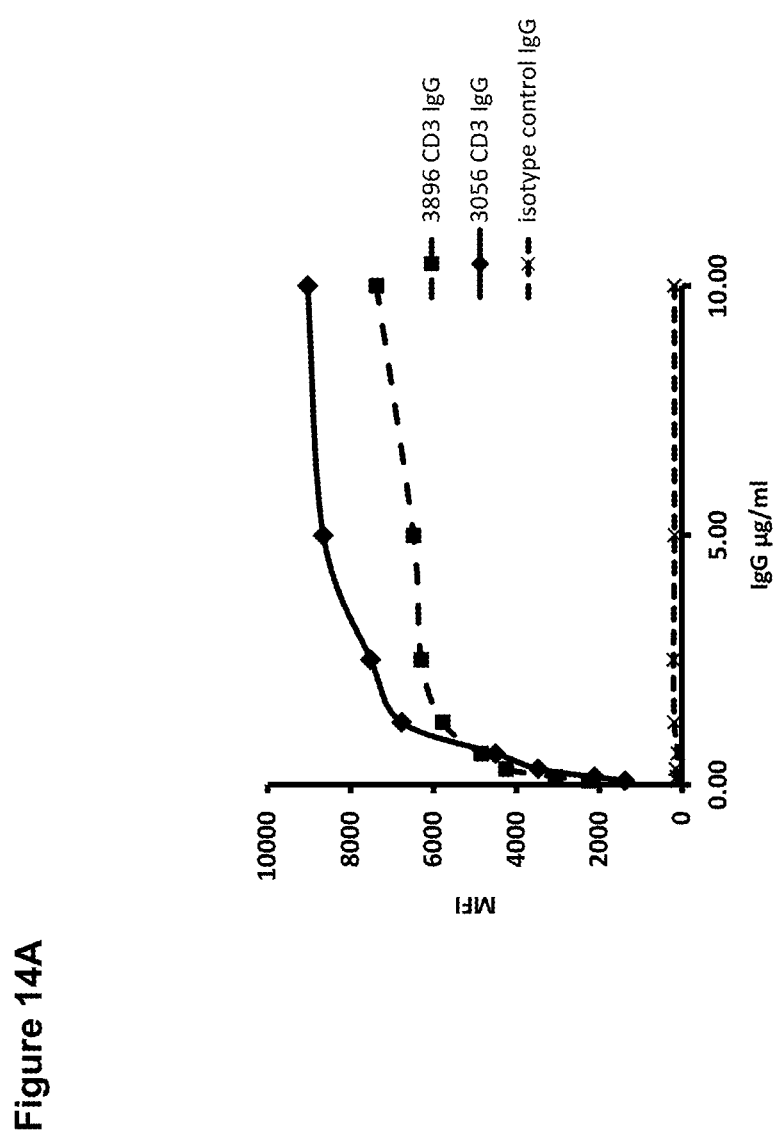
FIG. 14A: FACS staining anti-CD3 antibodies on HPB-ALL cells

The binding of candidate 3896 as full length bivalent monoclonal anti-CD3 IgG to membrane bound CD3 was compared with candidate 3056 as full length bivalent monoclonal anti-CD3 IgG by FACS analysis using CD3 expressing HPB-ALL cells. An irrelevant human IgG1 served as an isotype control IgG. Flow cytometry was performed according to standard procedures known in the art. As shown in FIG. 14A, the 3896 CD3 IgG dose-dependently bound to CD3 on HPB-ALL cells, as did the 3056 CD3 IgG.

Figure 14B:
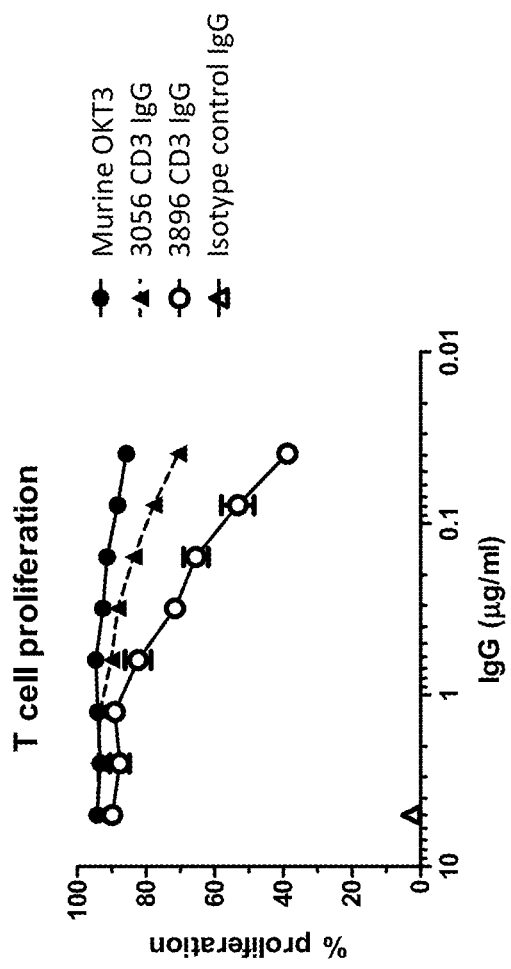
FIG. 14B: Plate bound IgG, T cells labeled with CFSE, read out at day 5 by FACS

Next, the ability of 3896 CD3 IgG to induce T-cell proliferation was tested in direct comparison to murine OKT3 CD3 antibody, 3056 CD3 IgG, and isotype control IgG. Briefly, the antibodies were serially diluted and immobilized onto 96-well plates. Upon removal of unbound IgG, CFSE-labeled T cells were added and incubated at 37° C. At day 5, the level of induced T cell proliferation was analyzed by flow cytometry. Results are expressed as the percentage of viable T cells displaying at least a twofold reduction in CFSE expression level and are shown in FIG. 14B. It was demonstrated that the 3896 CD3 IgG as a bivalent monospecific antibody was less potent in inducing T cell proliferation as compared to the candidate 3056 CD3 IgG and murine OKT3. These data suggest that the reduced level of T cell proliferation as induced by 3896 when compared to the 3056 CD3 IgG reflect the reduced CD3 binding capacity as analyzed by flow cytometry. This difference in binding allows for choosing an arm with a desired affinity, resulting in a bispecific antibody that displays a favorable balance between the binding affinities for CD3 and CLEC12A, so that T cells and CLEC12A-positive AML tumor cells are efficiently brought together, and T cell mediated lysis of CLEC12A-positive AML tumor cells is optimally induced.

Figure 15:
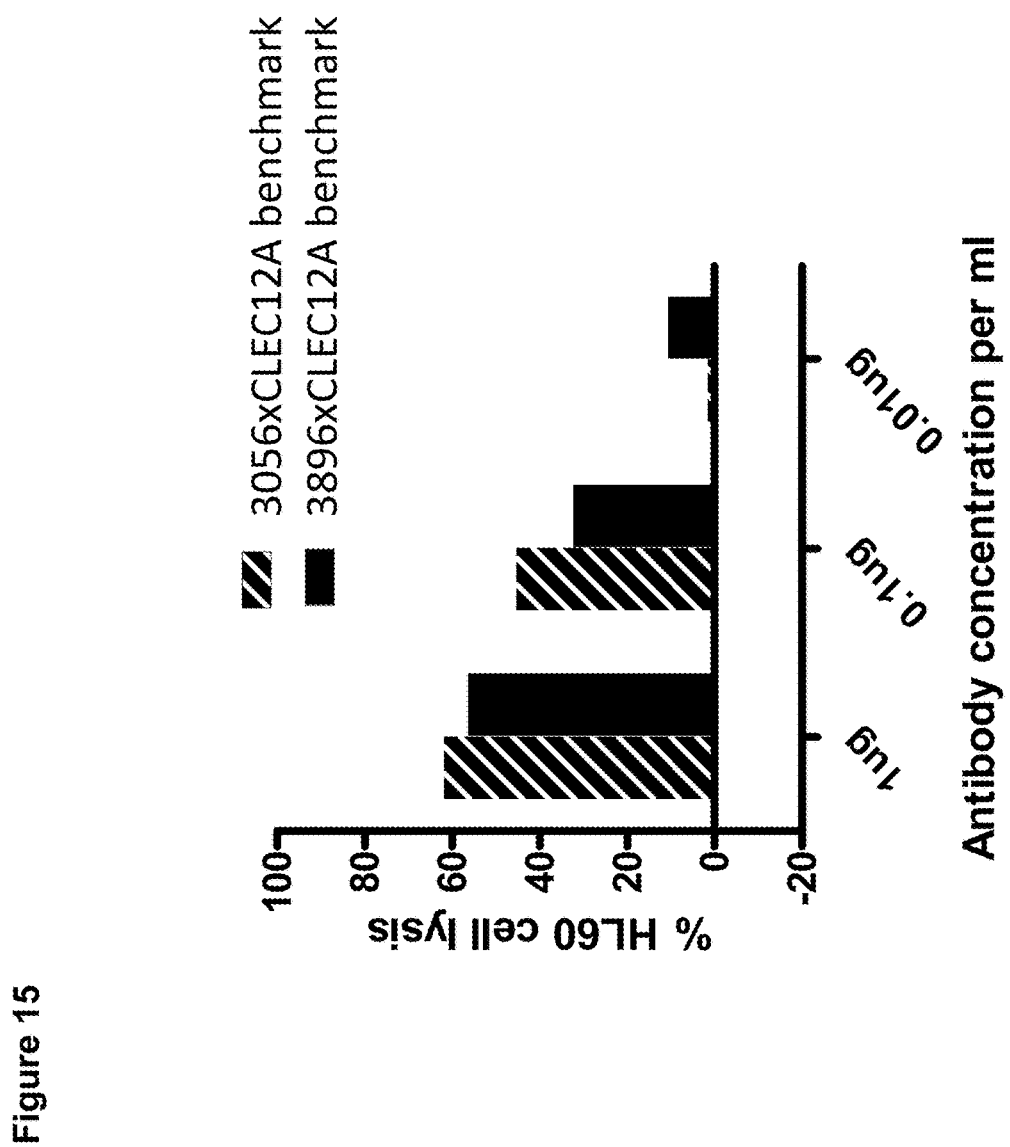
FIG. 15: HL60 cytotoxicity assay

To test the potency of the new 3896 anti-CD3 arm versus the 3056 anti-CD3 arm in a CD3×CLEC12A bispecific antibody format, the 3896×CLEC12A benchmark bispecific antibody of example 4 (candidate 3896×3116) and the 3056×CLEC12A benchmark bs antibody of example 1 (candidate 3056×3116) were directly compared in the HL60 cytotoxicity assay as previously described. The results are shown in FIG. 15. It was observed that the 3896×CLEC12A benchmark bsAb has similar potency as the 3056× CLEC12A benchmark bsAb. Hence, as both bispecific antibodies differ only in their CD3 Fab arm whilst the CLEC12A Fab arm is the same, it is concluded that the functionality of the 3896 CD3 Fab arm is similar to that of the 3056 CD3 Fab arm in a CD3×CLEC12A bispecific Ab. It is noted that at lower concentrations the candidate 3896× 3116 is even better than the candidate 3056×3116. This is favourable because it provides a larger therapeutic window, as explained herein before.

Example 16

In example 3, a panel of CLEC12A-specific Fab arms was selected from phage display libraries. All CLEC12A binding molecules contained the huVk1-39 light chain. Three CLEC12A binding molecules were selected: Fabs 3918 (SEQ ID NO: 35), 4327 (SEQ ID NO: 37) and 4331 (SEQ ID NO: 39). These Fabs were expressed as full length human IgG1: 3918 CLEC12A IgG, 4327 CLEC12A IgG and 4331 CLEC12A IgG.

The nucleotide and amino acid sequences of the VH of 3918 CLEC12A IgG (SEQ ID NOs: 34 and 35, respectively), the VH of 4327 CLEC12A IgG (SEQ ID NOs: 36 and 37, respectively), the VH of 4331 CLEC12A IgG (SEQ ID NOs: 38 and 39, respectively) and the common VL (IGKV1-39; 012; SEQ ID NO: 20) are provided in FIG. 20.

The full length CLEC12A antibodies were tested for binding to CLEC12A expressed by HL60 cells.

Figure 16:
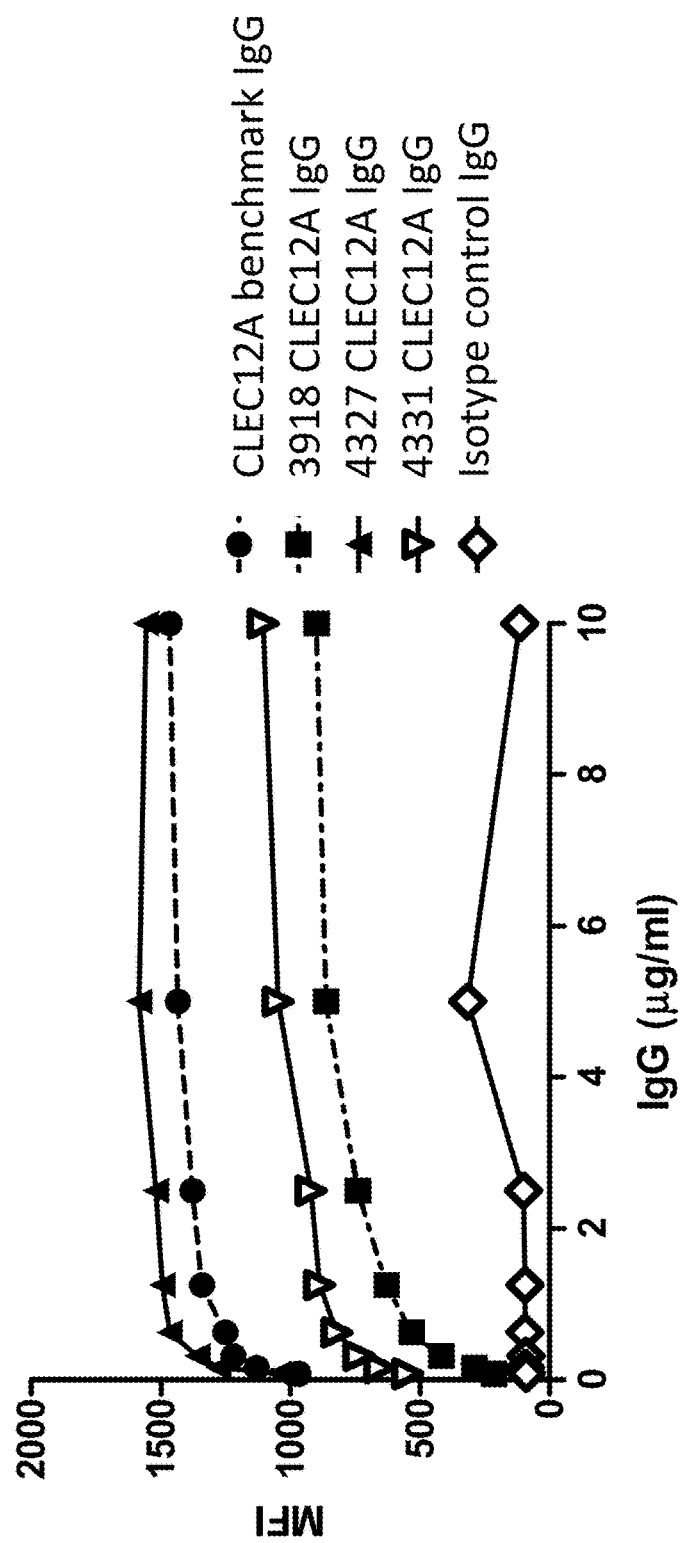
FIG. 16: FACS staining anti-CLEC12A antibodies on HL60 cells

The binding of 3918 CLEC12A IgG, 4327 CLEC12A IgG and 4331 CLEC12A IgG to membrane bound CLEC12A was compared with the CLEC12A benchmark antibody (3116) by FACS analysis using CLEC12A expressing HL60 cells. An irrelevant human IgG1 served as an isotype control IgG. Flow cytometry was performed according to standard procedures known in the art. As shown in FIG. 16, the 4327 CLEC12A IgG bound to CLEC12A in a similar fashion as the CLEC12A benchmark antibody. The other two antibodies, 3918 CLEC12A IgG and 4331 CLEC12A IgG also demonstrated a good dose-dependent binding to CLEC12A on HL60 cells. Their binding to CLEC12A seemed somewhat lower as compared to the CLEC12A benchmark antibody.

In conclusion, Fabs 3918, 4327 and 4331 are good CLEC12A binding arms.

Example 17

It was tested whether bispecific molecules containing the 3896 CD3 Fab arm and the CLEC12A Fab arm 3981, 4327 or 4331 were functional.

For this, the VH sequence of the 3896 CD3 Fab arm and the VH region of either the CLEC12A benchmark antibody, the 3918 CLEC12A Fab, the 4327 CLEC12A Fab or the 4331 CLEC12A Fab were cloned into expression vectors using methods known in the art for production of bispecific IgG1 (Gunasekaran et al., WO2009/089004) in conjunction with the rearranged huVκ1-39 light chain to result in bispecific antibodies; 3896×CLEC12A benchmark, 3896×3918, 3896×4327 and 3896×4331.

Figure 17:
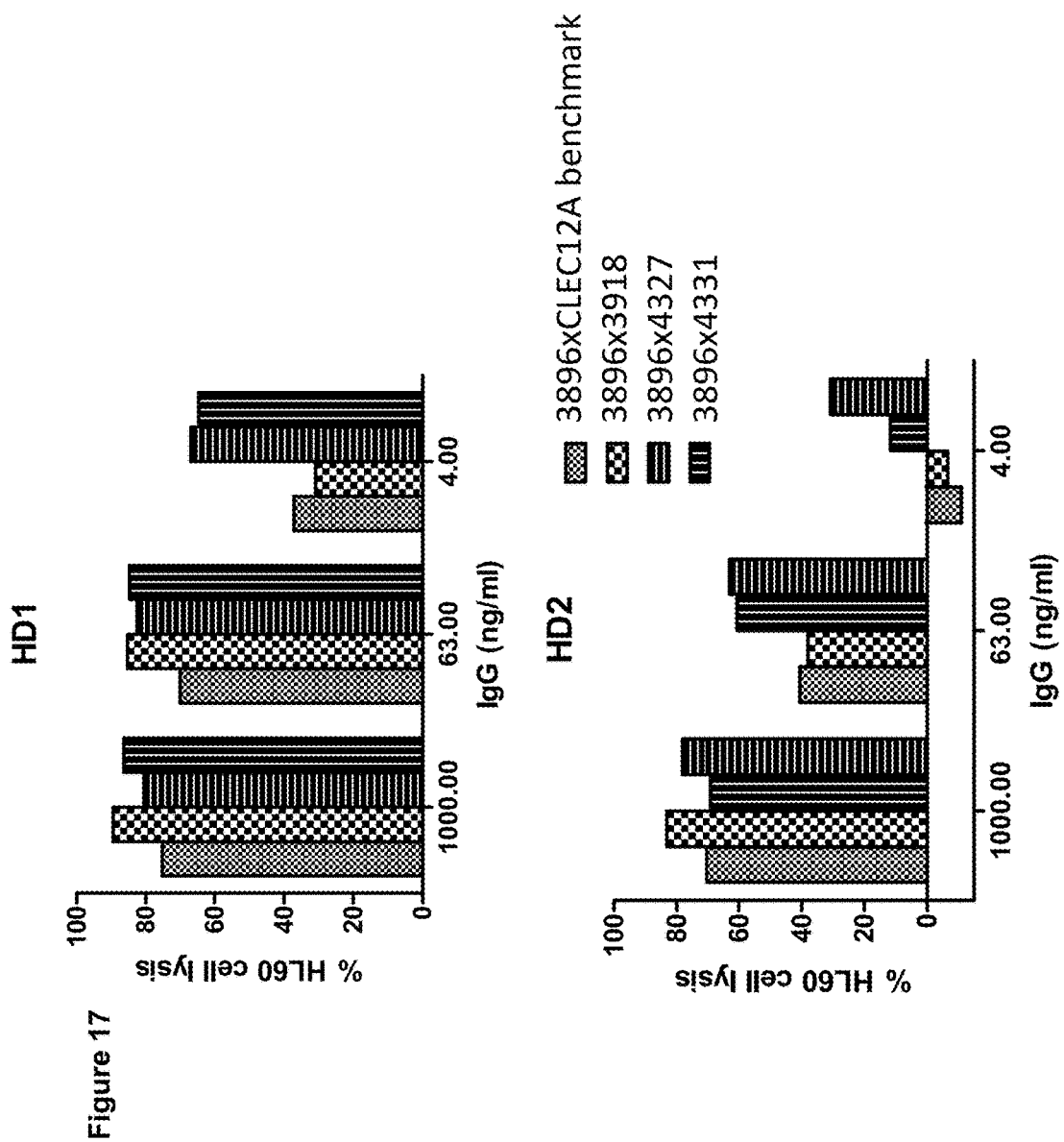
FIG. 17: HL60 cytotoxicity assay

These bispecifics were tested for functionality in the previously described HL60 cytotoxicity assay. Resting T cells from two healthy donors (HD1 and HD2) were co-cultured with CFSE-labeled HL60 cells in the presence of various concentrations of bispecific antibody at an E:T ratio 5:1 or 48 hours in the presence of 10% HS. Surviving CFSE-positive HL60 cells were quantified by flow cytometry at day 2. Results in FIG. 17 are expressed as the percentage specific lysis. For the two individual experiments with T cells from donor 1 (HD1; FIG. 17 upper panel) and T cells for donor 2 (HD2; FIG. 17 lower panel), it was demonstrated that all bispecifics were as potent as the 3896×CLEC12A benchmark bispecific when incubated at high concentration.

Of note, especially at lower concentrations of bispecific antibodies, it was observed that the 3896×4327 and 3896×4331 bispecific antibodies were more potent than the 3896×CLEC12A benchmark bispecific. Hence, as these bispecific antibodies differ only in their CLEC12A Fab arm whilst the CD3 Fab arm is the same, it can be concluded that the functionality of the 4327 and 4331 CLEC12A Fab arms is more potent as compared to the CLEC12A benchmark Fab arm. Without wishing to be bound to theory, the observed differences between the 3896×4327 and 3896×4331 versus the 3896×CLEC12A benchmark bispecific IgG may reflect a difference in binding affinity of these novel anti-CLEC12A Fab arms or they might be targeting a different CLEC12A epitope that allows a more efficient crosslinking of the tumor cells with CD3 expressing T cells.

Example 18

In example 2 it was demonstrated that the CLEC12A Fabs 3918 and 4331 competed for binding to an epitope on CLEC12A when tested in ELISA as Fab format against Fab fragments of the CLEC12A benchmark antibody. The 4327 CLEC12A Fab, however, did not compete with CLEC12A benchmark IgG for binding in this assay (Table 2).

In this experiment, it was tested whether the full length IgG of the 4327 CLEC12A IgG competed for binding to CLEC12A with the CLEC12A benchmark antibody. Briefly, HL60 cells were pre-incubated with primary antibody at 50 μg/ml on ice for 20 minutes. Subsequently, Oregon Green (OG)-labeled (Invitrogen, cat. no. A10476) second antibody was added at 1 μg/ml to the cells plus first antibody (concentration of first antibody after addition of OG-labeled IgG ~45 μg/ml). After 20 minutes cells were washed and analyzed by FACS.

Figure 18:
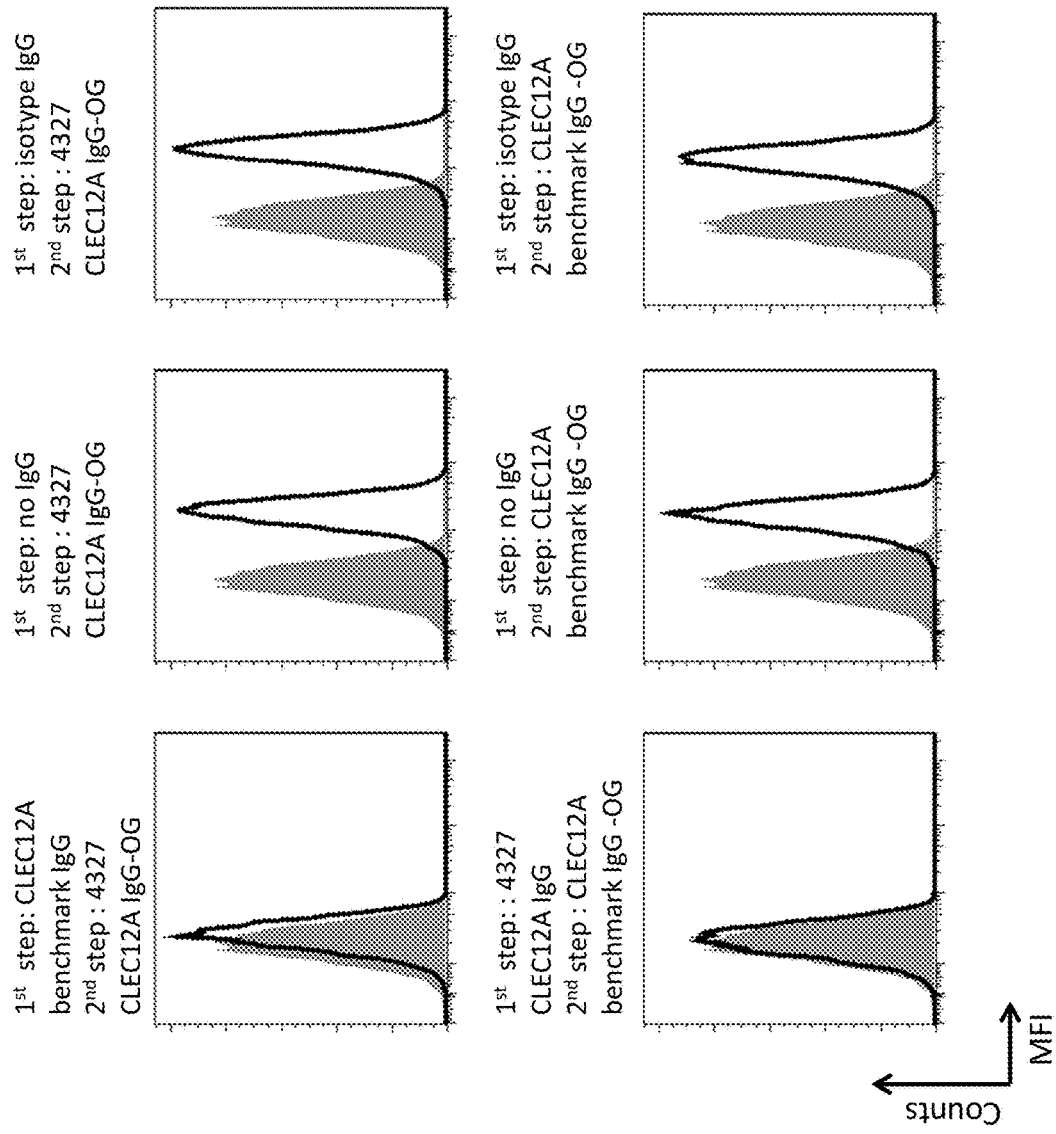
FIG. 18: FACS analysis

The results are shown in FIG. 18: it was concluded that 4327 CLEC12A IgG and CLEC12A benchmark IgG compete for binding to CLEC12A. This suggests that both IgGs bind either a closely related epitope on the CLEC12A antigen or that they bind to different epitopes which do not allow simultaneous binding of both IgGs due to steric hindrance.

Example 19

In previous examples it was demonstrated that the CLEC12A Fab arms 4327, 4331, 3918 as well as 3116 are good binders to CLEC12A and potent inducers of T cell mediated killing in a CD3×CLEC12A bispecific format. So-far, bispecific antibodies were obtained using known methods for driving immunoglobulin heavy chain heterodimerization (Gunasekaran et al.).

In our co-pending US and PCT applications (US regular application Ser. No. 13/866,747 and PCT/NL2013/050294; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are the amino acid substitutions L351K and T366K (numbering according to Kabat) in the first CH3 domain (the 'KK-variant' heavy chain) and the amino acid substitutions L351D and L368E in the second CH3 domain (the 'DE-variant' heavy chain), or vice versa. It was previously demonstrated in our co-pending U.S. Ser. No. 13/866,747 and PCT/NL2013/050294 applications that the DE-variant and KK-variant preferentially pair to form heterodimers (so-called 'DEKK' bispecific molecules). Homodimerization of DE-variant heavy chains (DEDE homodimers) or KK-variant heavy chains (KKKK homodimers) hardly occurs due to strong repulsion between the charged residues in the CH3-CH3 interface between identical heavy chains.

To demonstrate that the effect of CD3×CLEC12A bispecific molecules is not influenced by either the known mutations for heterodimerization (Gunasekaran) or the DEKK mutations, the DE-variant and KK-variant heavy chains were used to drive heterodimerization of the different heavy chains for making CD3×CLEC12A bispecifics. In addition the CH2/lower hinge double mutations (L235G and G236R; DM) were introduced in these DE- and KK-variant heavy chains. The Fc tail of these resulting bispecific molecules is referred to as 'DM DEKK'.

Figure 19:
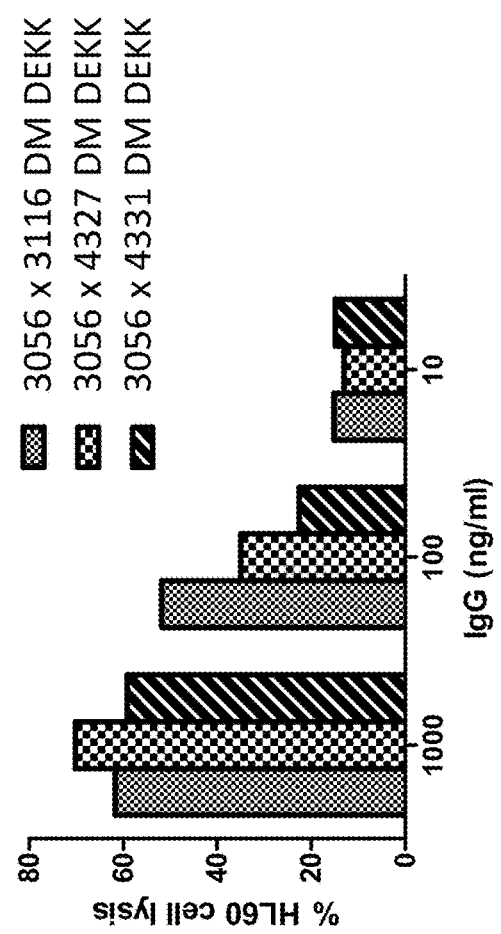
FIG. 19: HL60 cytotoxicity assay

Briefly, the VH regions of either the 3116, 4327 or 4331 CLEC12A Fab arms were cloned into expression vectors containing the DE-variant+DM heavy chain whereas the VH region of the 3056 CD3 antibody was cloned into an expression vector containing the KK-variant+DM heavy chain (US regular application Ser. No. 13/866,747 and PCT/NL2013/050294) and these expression vectors, together with a nucleic acid molecule encoding the rearranged human IGKV1-39/IGKJ1 (huVκ1-39) light chain, were provided to a host cell such that the host cell expressed and produced bispecific antibodies. The resulting 3056×3116 DM DEKK, 3056×4327 DM DEKK and 3056×4331 DM DEKK bispecific antibodies were subsequently tested for potency in the HL60 cytotoxicity assay as previously described. The results are shown in FIG. 19: it was demonstrated that all variants are still capable of efficient tumor cell lysis and it was thus concluded that the DM and DEKK mutations can be introduced into the Fc region of the CD3×CLEC12A bispecific antibody, while maintaining the capacity of inducing tumor cell lysis.

REFERENCES

Armour et al. Mol. Immunol. 2003 (40) 585-593
Bakker A. B. et al. Cancer Res 2004, 64, p8443-50
Bargou et al. 2008 Science 321:974
Bluemel et al. 2010 Cancer Immunol. Immunother. 59:1197
Chames and Baty, MABS 2009 (1) 539-547
Chatenoud et al. 1990, Transplantation 49(4), pages 697-702
Chen C. H. et al. Blood 2006, 107, p1459-67
Cui et al. JBC 2012 (287) 28206-28214
De Kruif et al. 1995, J Mol Biol 248(1), pages 97-105

De Kruif et al. J. Mol. Biol. 2009 (387) 548-58
De Kruif et al. Biotechnol Bioeng. 2010 (106)741-50
De Wildt R M et al. J. Mol. Biol. 1999 (285) 895-901;
Dreier et al. 2002 Int. J. Canc. 100:690
Geginat, J. et al. Blood, 2003. 101(11), p. 4260-6
Gunasekaran et al. JBC 2010 (285) 19637-19646
Haagen et al. 1995 Blood 85:3208
Han Y. et al. Blood 2004, 104, p2858-66
Kipriyanov et al. 1998 Int. J. Can. 77:763
Kontermann, MABS 2012 (4) 182-197
Lanzavecchia et al. 1987, Eur. J. Imm. 17:105
Liu et al. 1985 PNAS 82: 8648
Liesveld et al. 1988, J. Immunol. 140(5), pages 1527-1533
Loffler et al. 2000 Blood 95:2098
Marshall A. S. et al. J Biol Chem 2004, 279, p14792-802
Merchant et al. Nature Biotechnology 1998 Volume 16, pp 677-681
Moore et al. Blood 2011 (117) 4542-4551
Moshaver et al. 2008 Stem Cells 26:3059
Nissim et al. The EMBO Journal vol. 13 no. 3 pp. 692-698, 1994
Norde W. J. et al. Blood 2009 (113) (10): p. 2312-23
Offner et al. Molecular Immunology 2006 (43) 763-771
Oganesyan et al. Biol. Crystall. 2008(D64)700
Schaefer et al (Cancer Cell 20, 472-486, October 2011
Sheridan C, Nat Biotechnol. 2012 (30):300-1
Staerz et al. 1986 PNAS 83:1453
Shields R L et al. JBC 2001 (276) 6591-6604
Sluijter, B. J., et al. Clin Immunol, 2010. 137(2), p. 221-33
Suntharalingam et al. 2006, New England J Med 355(10), pages 1018-1028
Van Rhenen et al. 2007 Blood 110:2659
Zeidler et al. 1999 J. Immunol. 163:1246
WO2004/009618
WO2005/118635
WO2005/000894
WO2005/000894
WO2008/027236
WO2009/089004
WO2009/157771
WO2010/108127

The invention claimed is:

1. A bispecific IgG antibody comprising
   a first arm that specifically recognizes CLEC12A, wherein said first arm comprises a heavy chain CDR1 comprising the amino acid sequence SGYTFTGY (SEQ ID NO: 1), a heavy chain CDR2 comprising the amino acid sequence IINPSGGS (SEQ ID NO: 2), and a heavy chain CDR3 comprising the amino acid sequence GTTGDWFDY (SEQ ID NO: 3); and
   a second arm that specifically recognizes an antigen on immune effector cells capable of recruiting such cells to an aberrant cell expressing CLEC12A.

2. The bispecific IgG antibody according to claim 1, wherein the arm that specifically recognizes CLEC12A comprises a variable heavy chain that is at least 90% identical to the amino acid sequence:

QVQLVQSGAEVKKPGASVKVSCKASGYTFTS-YYMHWVRQAPGQGLEWMGIINPS GGST-SYAQKFQGRVTMTRDTSTSTVYMELSSLRSED-TAVYYCAKGTTGDWFDYW GQGTLVTVSS (SEQ ID NO: 4).

3. The bispecific antibody according to claim 1, wherein said first arm that specifically recognizes CLEC12A comprises a variable heavy chain comprising the amino acid sequence:

QVQLVQSGAEVKKPGASVKVSCKASGYTFTS-YYMHWVRQAPGQGLEWMGIINPS GGST-SYAQKFQGRVTMTRDTSTSTVYMELSSLRSED-TAVYYCAKGTTGDWFDYW GQGTLVTVSS (SEQ ID NO: 4).

4. The bispecific IgG antibody according to claim 1, wherein the variable light chain of said first arm comprises a variable light chain CDR1 comprising the amino acid sequence RASQSISSYLN (SEQ ID NO: 17), a light chain CDR2 comprising the amino acid sequence AASSLQS (SEQ ID NO: 18), and a light chain CDR3 comprising the amino acid sequence QQSYSTPPT (SEQ ID NO: 19).

5. The bispecific IgG antibody according to claim 4, wherein the first arm comprises a variable light chain that is at least 90% identical to the amino acid sequence:

DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

6. The bispecific IgG antibody according to claim 5, wherein the first arm comprises a variable light chain comprising the amino acid sequence:

DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

7. The bispecific IgG antibody according to claim 1, wherein said first and second arms comprise a common light chain.

8. The bispecific IgG antibody according to claim 1, comprising a mutated CH2 and/or lower hinge domains wherein the binding of said bispecific antibody with Fcγ receptors is significantly reduced.

9. The bispecific IgG antibody according to claim 8, wherein said mutated CH2 and/or lower hinge domains comprise amino acid substitution L235G and/or G236R.

10. The bispecific IgG according to claim 1, wherein said second arm specifically recognizes CD3.

11. A bispecific IgG antibody comprising
a first arm comprising a $V_H$ and a $V_L$, wherein said first arm specifically recognizes CLEC12A and comprises a heavy chain CDR1 comprising the amino acid sequence SGYTFTSY (SEQ ID NO: 5), a heavy chain CDR2 comprising the amino acid sequence IINPSGGS (SEQ ID NO: 6), and a heavy chain CDR3 comprising the amino acid sequence GNYGDEFDY (SEQ ID NO: 7); and
a second arm comprising a $V_H$ and a $V_L$, wherein said second arm specifically recognizes an antigen on immune effector cells capable of recruiting such cells to an aberrant cell expressing CLEC12A.

12. The bispecific IgG antibody according to claim 11, wherein the arm that specifically recognizes CLEC12A comprises a variable heavy chain that is at least 90% identical to the amino acid sequence:

EVQLVQSGAEVKKPGASVKVSCKASGYTFTS-YYMHWVRQAPGQGLEWMGIINPSG GST-SYAQKFQGRVTMTRDTSTSTVYMELSSLRSED-TAVYYCARGNYGDEFDYWGQ GTLVTVSS (SEQ ID NO: 8).

13. The bispecific antibody according to claim 11, wherein said first arm that specifically recognizes CLEC12A comprises a variable heavy chain comprising the amino acid sequence:

EVQLVQSGAEVKKPGASVKVSCKASGYTFTS-YYMHWVRQAPGQGLEWMGIINPSG GST-SYAQKFQGRVTMTRDTSTSTVYMELSSLRSED-TAVYYCARGNYGDEFDYWGQ GTLVTVSS (SEQ ID NO: 8).

14. The bispecific IgG antibody according to claim 11, wherein the variable light chain of said first arm comprises a variable light chain CDR1 comprising the amino acid sequence RASQSISSYLN (SEQ ID NO: 17), a light chain CDR2 comprising the amino acid sequence AASSLQS (SEQ ID NO: 18), and a light chain CDR3 comprising the amino acid sequence QQSYSTPPT (SEQ ID NO: 19).

15. The bispecific IgG antibody according to claim 14, wherein the first arm comprises a variable light chain that is at least 90% identical to the amino acid sequence:

DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

16. The bispecific IgG antibody according to claim 15, wherein the first arm comprises a variable light chain comprising the amino acid sequence:

DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

17. The bispecific IgG antibody according to claim 11, wherein said first and second arms comprise a common light chain.

18. The bispecific IgG antibody according to claim 11, comprising a mutated CH2 and/or lower hinge domains wherein the binding of said bispecific antibody with Fcγ receptors is significantly reduced.

19. The bispecific IgG antibody according to claim 18, wherein said mutated CH2 and/or lower hinge domains comprise amino acid substitution L235G and/or G236R.

20. The bispecific IgG according to claim 11, wherein said second arm specifically recognizes CD3.

21. A bispecific IgG antibody comprising
a first arm comprising a $V_H$ and a $V_L$, wherein said first arm specifically recognizes CLEC12A, and a heavy chain CDR1 comprising the amino acid sequence SGYTFTGY (SEQ ID NO: 9), a heavy chain CDR2 comprising the amino acid sequence WINPNSGG (SEQ ID NO: 10), and a heavy chain CDR3 comprising the amino acid sequence DGYFADAFDY (SEQ ID NO: 11); and
a second arm comprising a $V_H$ and a $V_L$, wherein said second arm specifically recognizes an antigen on immune effector cells capable of recruiting such cells to an aberrant cell expressing CLEC12A.

22. The bispecific IgG antibody according to claim 21, wherein the arm that specifically recognizes CLEC12A comprises a variable heavy chain that is at least 90% identical to the amino acid sequence:

QVQLVQSGAEVKKPGASVKVSCKASGYTFTS-YYMHWVRQAPGQGLEWMGIINPS GGST-

SYAQKFQGRVTMTRDTSTSTVYMELSSLRSED-TAVYYCAKGTTGDWFDYW GQGTLVTVSS (SEQ ID NO: 4).

23. The bispecific antibody according to claim 21, wherein said first arm that specifically recognizes CLEC12A comprises a variable heavy chain comprising the amino acid sequence:
QVQLVQSGAEVKKPGASVKVSCKASGYTFT-GYYMHWVRQAPGQGLEWMGWINP NSGGT-NYAQKFQGRVTMTRDTSISTAYMELSRLRSDD-TAVYYCARDGYFADAFDY WGQGTLVTVSS (SEQ ID NO: 12).

24. The bispecific IgG antibody according to claim 21, wherein the variable light chain of said first arm comprises a variable light chain CDR1 comprising the amino acid sequence RASQSISSYLN (SEQ ID NO: 17), a light chain CDR2 comprising the amino acid sequence AASSLQS (SEQ ID NO: 18), and a light chain CDR3 comprising the amino acid sequence QQSYSTPPT (SEQ ID NO: 19).

25. The bispecific IgG antibody according to claim 24, wherein the first arm comprises a variable light chain that is at least 90% identical to the amino acid sequence:
DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

26. The bispecific IgG antibody according to claim 25, wherein the first arm comprises a variable light chain comprising the amino acid sequence:
DIQMTQSPSSLSASVGDRVTITCRASQSISSYLNWY-QQKPGKAPKLLIYAASSLQSGV PSRFSGSGS-GTDFTLTISSLQPEDFATYYCQQSYSTPPTF-GQGTKVEIK (SEQ ID NO: 20).

27. The bispecific IgG antibody according to claim 21, wherein said first and second arms comprise a common light chain.

28. The bispecific IgG antibody according to claim 21, comprising a mutated CH2 and/or lower hinge domains wherein the binding of said bispecific antibody with Fcγ receptors is significantly reduced.

29. The bispecific IgG antibody according to claim 22, wherein said mutated CH2 and/or lower hinge domains comprise amino acid substitution L235G and/or G236R.

30. The bispecific IgG according to claim 21, wherein said second arm specifically recognizes CD3.

* * * * *

SEQUENCE LISTING

<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: Synthetic: CLEC12A 4327 VH CDR1

<400> SEQUENCE: 1

Ser Gly Tyr Thr Phe Thr Ser Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic: CLEC12A 4327 VH CDR2

<400> SEQUENCE: 2

Ile Ile Asn Pro Ser Gly Gly Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic: CLEC12A 4237 VH CDR3

<400> SEQUENCE: 3

Gly Thr Thr Gly Asp Trp Phe Asp Tyr
1               5

<210> SEQ ID NO 4
<211> LENGTH: 118
<212> TYPE: PRT
<213> ORGANISM: Artificial Sequence
<220> FEATURE:
<223> OTHER INFORMATION: Synthetic: CLEC12A 4237 VH sequence

<400> SEQUENCE: 4

Gln Val Gln Leu Val Gln Ser Gly Ala Glu Val Lys Lys Pro Gly Ala

```
                1               5                  10                  15
Ser Val Lys Val Ser Cys Lys Ala Ser Gly Tyr Thr Phe Thr Ser Tyr
                    20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                 70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
            100                 105                 110

Leu Val Thr Val Ser Ser
        115
```

```
<210> SEQ ID NO 5
<211> LENGTH: 8
<212> TYPE: PRT
<213> ORGANISM: Artificial Sequence
<220> FEATURE:
<223> OTHER INFORMATION: Synthetic: CLEC12A 4331 VH CDR1

<400> SEQUENCE: 5

Ser Gly Tyr Thr Phe Thr Ser Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic: CLEC12A 4331 VH CDR2

<400> SEQUENCE: 6

Ile Ile Asn Pro Ser Gly Gly Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic: CLEC12A 4331 VH CDR3

<400> SEQUENCE: 7

Gly Asn Tyr Gly Asp Glu Phe Asp Tyr
1               5

<210> SEQ ID NO 8
<211> LENGTH: 118
<212> TYPE: PRT
<213> ORGANISM: Artificial Sequence
<220> FEATURE:
<223> OTHER INFORMATION: Synthetic: CLEC12A 4331 VH

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                    20                  25                  30

Tyr Met His Trp Val Arg Gln Ala Pro Gly Gln Gly Leu Glu Trp Met
```

```
                35                  40                  45
Gly Ile Ile Asn Pro Ser Gly Gly Ser Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Asn Tyr Gly Asp Glu Phe Asp Tyr Trp Gly Gln Gly Thr
            100                 105                 110
Leu Val Thr Val Ser Ser
        115

<210> SEQ ID NO 9
<211> LENGTH: 8
<212> TYPE: PRT
<213> ORGANISM: Artificial Sequence
<220> FEATURE:
<223> OTHER INFORMATION: Synthetic: CLEC12A 3918 VH CDR1

<400> SEQUENCE: 9

Ser Gly Tyr Thr Phe Thr Gly Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic: CLEC12A 3918 VH CDR2

<400> SEQUENCE: 10

Trp Ile Asn Pro Asn Ser Gly Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic: CLEC12A 3918 VH CDR3

<400> SEQUENCE: 11

Asp Gly Tyr Phe Ala Asp Ala Phe Asp Tyr
1               5                   10

<210> SEQ ID NO 12
<211> LENGTH: 119
<212> TYPE: PRT
<213> ORGANISM: Artificial Sequence
<220> FEATURE:
<223> OTHER INFORMATION: Synthetic: CLEC12A 3918 VH

<400> SEQUENCE: 12

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
        50                  55                  60
Gln Gly Arg Val Thr Met Thr Arg Asp Thr Ser Ile Ser Thr Ala Tyr
```

```
                65                  70                  75                  80
Met Glu Leu Ser Arg Leu Arg Ser Asp Asp Thr Ala Val Tyr Tyr Cys
                        85                  90                  95

Ala Arg Asp Gly Tyr Phe Ala Asp Ala Phe Asp Tyr Trp Gly Gln Gly
                100                 105                 110

Thr Leu Val Thr Val Ser Ser
        115
```

<210> SEQ ID NO 13
<211> LENGTH: 5
<212> TYPE: PRT
<213> ORGANISM: Artificial Sequence
<220> FEATURE:
<223> OTHER INFORMATION: Synthetic: CD3 3896 VH CDR1

<400> SEQUENCE: 13

```
Ser Tyr Gly Met His
1               5
```

<210> SEQ ID NO 14
<211> LENGTH: 17
<212> TYPE: PRT
<213> ORGANISM: Artificial Sequence
<220> FEATURE:
<223> OTHER INFORMATION: Synthetic: CD3 3896 VH CDR2

<400> SEQUENCE: 14

```
Ile Ile Trp Tyr Ser Gly Ser Lys Lys Asn Tyr Ala Asp Ser Val Lys
1               5                   10                  15

Gly
```

<210> SEQ ID NO 15
<211> LENGTH: 9
<212> TYPE: PRT
<213> ORGANISM: Artificial Sequence
<220> FEATURE:
<223> OTHER INFORMATION: Synthetic: CD3 3896 VH CDR3

<400> SEQUENCE: 15

```
Gly Thr Gly Tyr Asn Trp Phe Asp Pro
1               5
```

<210> SEQ ID NO 16
<211> LENGTH: 118
<212> TYPE: PRT
<213> ORGANISM: Artificial Sequence
<220> FEATURE:
<223> OTHER INFORMATION: Synthetic: CLEC12A 3896 VH

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Ile Ile Trp Tyr Ser Gly Ser Lys Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Thr Gly Tyr Asn Trp Phe Asp Pro Trp Gly Gln Gly Thr
            100                 105                 110

Leu Val Thr Val Ser Ser
        115

<210> SEQ ID NO 17
<211> LENGTH: 11
<212> TYPE: PRT
<213> ORGANISM: Artificial Sequence
<220> FEATURE:
<223> OTHER INFORMATION: Synthetic: O12 VL CDR1

<400> SEQUENCE: 17

Arg Ala Ser Gln Ser Ile Ser Ser Tyr Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic: O12 VL CDR2

<400> SEQUENCE: 18

Ala Ala Ser Ser Leu Gln Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic: O12 VL CDR3

<400> SEQUENCE: 19

Gln Gln Ser Tyr Ser Thr Pro Pro Thr
1               5

<210> SEQ ID NO 20
<211> LENGTH: 107
<212> TYPE: PRT
<213> ORGANISM: Artificial Sequence
<220> FEATURE:
<223> OTHER INFORMATION: Synthetic: O12 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 21
```

<211> LENGTH: 265
<212> TYPE: PRT
<213> ORGANISM: Homo sapiens
<220> FEATURE:
<221> NAME/KEY: misc_feature
<223> OTHER INFORMATION: KLRL1

<400> SEQUENCE: 21

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Gln Arg Met Ile Cys Glu Lys Met Ala Asn Pro Val Gln
                245                 250                 255

Leu Gly Ser Thr Tyr Phe Arg Glu Ala
            260                 265

<210> SEQ ID NO 22
<211> LENGTH: 265
<212> TYPE: PRT
<213> ORGANISM: Homo sapiens
<220> FEATURE:
<221> NAME/KEY: misc_feature
<223> OTHER INFORMATION: MICL

<400> SEQUENCE: 22

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

```
Leu Cys Leu Leu Leu Leu Ile Gly Leu Gly Val Leu Ala Ser Met Phe
        50                  55                  60

His Val Thr Leu Lys Ile Glu Met Lys Lys Met Asn Lys Leu Gln Asn
 65                  70                  75                  80

Ile Ser Glu Glu Leu Gln Arg Asn Ile Ser Leu Gln Leu Met Ser Asn
                 85                  90                  95

Met Asn Ile Ser Asn Lys Ile Arg Asn Leu Ser Thr Thr Leu Gln Thr
                100                 105                 110

Ile Ala Thr Lys Leu Cys Arg Glu Leu Tyr Ser Lys Glu Gln Glu His
                115                 120                 125

Lys Cys Lys Pro Cys Pro Arg Arg Trp Ile Trp His Lys Asp Ser Cys
130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
                180                 185                 190

Leu Ser Pro Glu Glu Asp Ser Thr Arg Gly Met Arg Val Asp Asn Ile
                195                 200                 205

Ile Asn Ser Ser Ala Trp Val Ile Arg Asn Ala Pro Asp Leu Asn Asn
210                 215                 220

Met Tyr Cys Gly Tyr Ile Asn Arg Leu Tyr Val Gln Tyr Tyr His Cys
225                 230                 235                 240

Thr Tyr Lys Gln Arg Met Ile Cys Glu Lys Met Ala Asn Pro Val Gln
                245                 250                 255

Leu Gly Ser Thr Tyr Phe Arg Glu Ala
                260                 265

<210> SEQ ID NO 23
<211> LENGTH: 265
<212> TYPE: PRT
<213> ORGANISM: Homo sapiens
<220> FEATURE:
<221> NAME/KEY: misc_feature
<223> OTHER INFORMATION: DCAL-2

<400> SEQUENCE: 23

Met Ser Glu Glu Val Thr Tyr Ala Asp Leu Gln Phe Gln Asn Ser Ser
 1               5                  10                  15

Glu Met Glu Lys Ile Pro Glu Ile Gly Lys Phe Gly Glu Lys Ala Pro
                20                  25                  30

Pro Ala Pro Ser His Val Trp Arg Pro Ala Ala Leu Phe Leu Thr Leu
                35                  40                  45

Leu Cys Leu Leu Leu Leu Ile Gly Leu Gly Val Leu Ala Ser Met Phe
        50                  55                  60

His Val Thr Leu Lys Ile Glu Met Lys Lys Met Asn Lys Leu Gln Asn
 65                  70                  75                  80

Ile Ser Glu Glu Leu Gln Arg Asn Ile Ser Leu Gln Leu Met Ser Asn
                 85                  90                  95

Met Asn Ile Ser Asn Lys Ile Arg Asn Leu Ser Thr Thr Leu Gln Thr
                100                 105                 110

Ile Ala Thr Lys Leu Cys Arg Glu Leu Tyr Ser Lys Glu Gln Glu His
                115                 120                 125

Lys Cys Lys Pro Cys Pro Arg Arg Trp Ile Trp His Lys Asp Ser Cys
```

```
            130                 135                 140
Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
                180                 185                 190

Leu Ser Pro Glu Glu Asp Ser Thr Arg Gly Met Arg Val Asp Asn Ile
                195                 200                 205

Ile Asn Ser Ser Ala Trp Val Ile Arg Asn Ala Pro Asp Leu Asn Asn
210                 215                 220

Met Tyr Cys Gly Tyr Ile Asn Arg Leu Tyr Val Gln Tyr Tyr His Cys
225                 230                 235                 240

Thr Tyr Lys Gln Arg Met Ile Cys Glu Lys Met Ala Asn Pro Val Gln
                245                 250                 255

Leu Gly Ser Thr Tyr Phe Arg Glu Ala
                260                 265
```

<210> SEQ ID NO 24
<211> LENGTH: 275
<212> TYPE: PRT
<213> ORGANISM: Homo sapiens
<220> FEATURE:
<221> NAME/KEY: misc_feature
<223> OTHER INFORMATION: CLL-1

<400> SEQUENCE: 24

```
Met Trp Ile Asp Phe Phe Thr Tyr Ser Ser Met Ser Glu Glu Val Thr
1               5                   10                  15

Tyr Ala Asp Leu Gln Phe Gln Asn Ser Ser Glu Met Gly Lys Ile Pro
                20                  25                  30

Glu Ile Gly Lys Phe Gly Glu Lys Ala Pro Pro Ala Pro Ser His Val
                35                  40                  45

Trp Arg Pro Ala Ala Leu Phe Leu Thr Leu Leu Cys Leu Leu Leu Leu
            50                  55                  60

Ile Gly Leu Gly Val Leu Ala Ser Met Phe His Val Thr Leu Lys Ile
65                  70                  75                  80

Glu Met Lys Lys Met Asn Lys Leu Gln Asn Ile Ser Glu Glu Leu Gln
                85                  90                  95

Arg Asn Ile Ser Leu Gln Leu Met Ser Asn Met Asn Ile Ser Asn Lys
                100                 105                 110

Ile Arg Asn Leu Ser Thr Thr Leu Gln Thr Ile Ala Thr Lys Leu Cys
            115                 120                 125

Arg Glu Leu Tyr Ser Lys Glu Gln Glu His Lys Cys Lys Pro Cys Pro
130                 135                 140

Arg Arg Trp Ile Trp His Lys Asp Ser Cys Tyr Phe Leu Ser Asp Asp
145                 150                 155                 160

Val Gln Thr Trp Gln Glu Ser Lys Met Ala Cys Ala Ala Gln Asn Ala
                165                 170                 175

Ser Leu Leu Lys Ile Asn Asn Lys Asn Ala Leu Glu Phe Ile Lys Ser
                180                 185                 190

Gln Ser Arg Ser Tyr Asp Tyr Trp Leu Gly Leu Ser Pro Glu Glu Asp
                195                 200                 205

Ser Thr Arg Gly Met Arg Val Asp Asn Ile Ile Asn Ser Ser Ala Trp
            210                 215                 220
```

```
Val Ile Arg Asn Ala Pro Asp Leu Asn Asn Met Tyr Cys Gly Tyr Ile
225                 230                 235                 240

Asn Arg Leu Tyr Val Gln Tyr Tyr His Cys Thr Tyr Lys Lys Arg Met
            245                 250                 255

Ile Cys Glu Lys Met Ala Asn Pro Val Gln Leu Gly Ser Thr Tyr Phe
        260                 265                 270

Arg Glu Ala
        275

<210> SEQ ID NO 25
<211> LENGTH: 276
<212> TYPE: PRT
<213> ORGANISM: Homo sapiens
<220> FEATURE:
<221> NAME/KEY: misc_feature
<223> OTHER INFORMATION: CLEC12B

<400> SEQUENCE: 25

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
            20                  25                  30

Pro Ala Pro Ser Pro Ile Trp Arg His Ala Ala Leu Gly Leu Val Thr
        35                  40                  45

Leu Cys Leu Met Leu Leu Ile Gly Leu Val Thr Leu Gly Met Met Phe
50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
            85                  90                  95

Gly Asn Ser Asn Asn Leu Ser Met Glu Glu Phe Leu Lys Ser Gln
                100                 105                 110

Ile Ser Ser Val Leu Lys Arg Gln Glu Gln Met Ala Ile Lys Leu Cys
            115                 120                 125

Gln Glu Leu Ile Ile His Thr Ser Asp His Arg Cys Asn Pro Cys Pro
130                 135                 140

Lys Met Trp Gln Trp Tyr Gln Asn Ser Cys Tyr Tyr Phe Thr Thr Asn
145                 150                 155                 160

Glu Glu Lys Thr Trp Ala Asn Ser Arg Lys Asp Cys Ile Asp Lys Asn
            165                 170                 175

Ser Thr Leu Val Lys Ile Asp Ser Leu Glu Glu Lys Asp Phe Leu Met
            180                 185                 190

Ser Gln Pro Leu Leu Met Phe Ser Phe Phe Trp Leu Gly Leu Ser Trp
        195                 200                 205

Asp Ser Ser Gly Arg Ser Trp Phe Trp Glu Asp Gly Ser Val Pro Ser
        210                 215                 220

Pro Ser Leu Phe Ser Thr Lys Glu Leu Asp Gln Ile Asn Gly Ser Lys
225                 230                 235                 240

Gly Cys Ala Tyr Phe Gln Lys Gly Asn Ile Tyr Ile Ser Arg Cys Ser
            245                 250                 255

Ala Glu Ile Phe Trp Ile Cys Glu Lys Thr Ala Ala Pro Val Lys Thr
            260                 265                 270

Glu Asp Leu Asp
        275

<210> SEQ ID NO 26
```

```
<211> LENGTH: 354
<212> TYPE: DNA
<213> ORGANISM: Artificial Sequence
<220> FEATURE:
<223> OTHER INFORMATION: Synthetic: 3056 VH (VDJ)
<220> FEATURE:
<221> NAME/KEY: CDS
<222> LOCATION: (1)..(354)

<400> SEQUENCE: 26 cag gtg cag ctg gtg cag tct ggc ggc gga gtg gtg cag ccc ggc aga      48
Gln Val Gln Leu Val Gln Ser Gly Gly Gly Val Val Gln Pro Gly Arg
1               5                   10                  15 agc ctg aga ctg agc tgc gtg gcc agc ggc ttc acc ttc agc agc tac      96
Ser Leu Arg Leu Ser Cys Val Ala Ser Gly Phe Thr Phe Ser Ser Tyr
            20                  25                  30 ggc atg cac tgg gtc cgc cag gcc cct ggc aag gga ctg gaa tgg gtg     144
Gly Met His Trp Val Arg Gln Ala Pro Gly Lys Gly Leu Glu Trp Val
        35                  40                  45 gcc gcc atc tgg tac aac ggc cgg aag cag gac tac gcc gac agc gtg     192
Ala Ala Ile Trp Tyr Asn Gly Arg Lys Gln Asp Tyr Ala Asp Ser Val
    50                  55                  60 aag ggc cgg ttc acc atc agc cgg gac aac agc aag aac acc ctg tac     240
Lys Gly Arg Phe Thr Ile Ser Arg Asp Asn Ser Lys Asn Thr Leu Tyr
65                  70                  75                  80 ctg cag atg aac agc ctc cgg gcc gag gac acc gcc gtg tac tac tgt     288
Leu Gln Met Asn Ser Leu Arg Ala Glu Asp Thr Ala Val Tyr Tyr Cys
                85                  90                  95 acc cgg ggc acc ggc tac aat tgg ttc gac cct tgg ggc cag ggc acc     336
Thr Arg Gly Thr Gly Tyr Asn Trp Phe Asp Pro Trp Gly Gln Gly Thr
            100                 105                 110 ctg gtc acc gtc tcc agt                                             354
Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct 3056 VH

<400> SEQUENCE: 27

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asn Gly Arg Lys Gln Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Thr Gly Tyr Asn Trp Phe Asp Pro Trp Gly Gln Gly Thr
            100                 105                 110

Leu Val Thr Val Ser Ser
        115

<210> SEQ ID NO 28
```

```
<211> LENGTH: 322
<212> TYPE: DNA
<213> ORGANISM: Artificial Sequence
<220> FEATURE:
<223> OTHER INFORMATION: Synthetic: 3056 VL/O12 (VJ)
<220> FEATURE:
<221> NAME/KEY: CDS
<222> LOCATION: (1)..(321)

<400> SEQUENCE: 28 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa c                       322
Thr Phe Gly Gln Gly Thr Lys Val Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic Construct VL/O12

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 30
<211> LENGTH: 354
<212> TYPE: DNA
<213> ORGANISM: Artificial Sequence
<220> FEATURE:
<223> OTHER INFORMATION: Synthetic: 3896 VH
<220> FEATURE:
<221> NAME/KEY: CDS
```

<222> LOCATION: (1)..(354)

<400> SEQUENCE: 30

```
cag gtg cag ctg gtg gag tct ggc ggc gga gtg gtg cag ccc ggc aga      48
Gln Val Gln Leu Val Glu Ser Gly Gly Gly Val Val Gln Pro Gly Arg
1               5                   10                  15 agc ctg aga ctg agc tgc gcc gcc agc ggc ttc acc ttc aga agc tac      96
Ser Leu Arg Leu Ser Cys Ala Ala Ser Gly Phe Thr Phe Arg Ser Tyr
            20                  25                  30 ggc atg cac tgg gtc cgc cag gcc cct ggc aag gga ctg gaa tgg gtg     144
Gly Met His Trp Val Arg Gln Ala Pro Gly Lys Gly Leu Glu Trp Val
        35                  40                  45 gcc atc atc tgg tac agc ggc agc aag aag aac tac gcc gac agc gtg     192
Ala Ile Ile Trp Tyr Ser Gly Ser Lys Lys Asn Tyr Ala Asp Ser Val
    50                  55                  60 aag ggc cgg ttc acc atc agc cgg gac aac agc aag aac acc ctg tac     240
Lys Gly Arg Phe Thr Ile Ser Arg Asp Asn Ser Lys Asn Thr Leu Tyr
65                  70                  75                  80 ctg cag atg aac agc ctc cgg gcc gag gac acc gcc gtg tac tac tgt     288
Leu Gln Met Asn Ser Leu Arg Ala Glu Asp Thr Ala Val Tyr Tyr Cys
                85                  90                  95 gcc cgg ggc acc ggc tac aat tgg ttc gac cct tgg ggc cag ggc acc     336
Ala Arg Gly Thr Gly Tyr Asn Trp Phe Asp Pro Trp Gly Gln Gly Thr
            100                 105                 110 ctg gtc acc gtc tcc agt                                             354
Leu Val Thr Val Ser Ser
        115
```

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct 3986 VH

<400> SEQUENCE: 31

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Ile Ile Trp Tyr Ser Gly Ser Lys Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 32
<211> LENGTH: 354
<212> TYPE: DNA
<213> ORGANISM: Artificial Sequence
<220> FEATURE:
<223> OTHER INFORMATION: Synthetic: 3116 VH
<220> FEATURE:
<221> NAME/KEY: CDS -continued

<222> LOCATION: (1)..(354)

<400> SEQUENCE: 32

```
cag gtg cag ctg cag gaa tct gga ccc gga ctg gtc aag ccc agc gag      48
Gln Val Gln Leu Gln Glu Ser Gly Pro Gly Leu Val Lys Pro Ser Glu
1               5                   10                  15 aca ctg agc ctg acc tgt gtg gtg tcc ggc ggc agc atc agc agc agc      96
Thr Leu Ser Leu Thr Cys Val Val Ser Gly Gly Ser Ile Ser Ser Ser
            20                  25                  30 aat tgg tgg tct tgg gtc cga cag ccc cct ggc aag ggc ctg gaa tgg     144
Asn Trp Trp Ser Trp Val Arg Gln Pro Pro Gly Lys Gly Leu Glu Trp
        35                  40                  45 atc ggc gag atc tac cac agc ggc agc ccc gac tac aac ccc agc ctg     192
Ile Gly Glu Ile Tyr His Ser Gly Ser Pro Asp Tyr Asn Pro Ser Leu
    50                  55                  60 aag tcc aga gtg acc atc agc gtg gac aag agc cgg aac cag ttc agc     240
Lys Ser Arg Val Thr Ile Ser Val Asp Lys Ser Arg Asn Gln Phe Ser
65                  70                  75                  80 ctg aag ctg agc agc gtg aca gcc gcc gat acc gcc gtg tac tac tgc     288
Leu Lys Leu Ser Ser Val Thr Ala Ala Asp Thr Ala Val Tyr Tyr Cys
                85                  90                  95 gcc aaa gtg tcc acc ggc ggc ttt ttc gac tac tgg ggc cag ggc aca     336
Ala Lys Val Ser Thr Gly Gly Phe Phe Asp Tyr Trp Gly Gln Gly Thr
            100                 105                 110 ctg gtc acc gtc tcc agt                                             354
Leu Val Thr Val Ser Ser
            115
```

<210> SEQ ID NO 33
<211> LENGTH: 118
<212> TYPE: PRT
<213> ORGANISM: Artificial Sequence
<220> FEATURE:
<223> OTHER INFORMATION: Synthetic Construct 3116 VH

<400> SEQUENCE: 33

```
Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asp Tyr Asn Pro Ser Leu
    50                  55                  60

Lys Ser Arg Val Thr Ile Ser Val Asp Lys Ser Arg Asn Gln Phe Ser
65                  70                  75                  80

Leu Lys Leu Ser Ser Val Thr Ala Ala Asp Thr Ala Val Tyr Tyr Cys
                85                  90                  95

Ala Lys Val Ser Thr Gly Gly Phe Phe Asp Tyr Trp Gly Gln Gly Thr
            100                 105                 110

Leu Val Thr Val Ser Ser
            115
```

<210> SEQ ID NO 34
<211> LENGTH: 357
<212> TYPE: DNA
<213> ORGANISM: Artificial Sequence
<220> FEATURE:
<223> OTHER INFORMATION: Synthetic: 3918 VH
<220> FEATURE:
<221> NAME/KEY: CDS

<222> LOCATION: (1)..(357)

<400> SEQUENCE: 34

| cag gtg cag ctg gtg cag tct ggg gct gag gtg aag aag cct ggg gcc | 48 |
|---|---|
| Gln Val Gln Leu Val Gln Ser Gly Ala Glu Val Lys Lys Pro Gly Ala | |
| 1               5                   10                  15 | |

| tca gtg aag gtc tcc tgc aag gct tct gga tac acc ttc acc ggc tac | 96 |
|---|---|
| Ser Val Lys Val Ser Cys Lys Ala Ser Gly Tyr Thr Phe Thr Gly Tyr | |
|         20                  25                  30 | |

| tat atg cac tgg gtg cga cag gcc cct gga caa ggg ctt gag tgg atg | 144 |
|---|---|
| Tyr Met His Trp Val Arg Gln Ala Pro Gly Gln Gly Leu Glu Trp Met | |
|     35                  40                  45 | |

| gga tgg atc aac cct aac agt ggt ggc aca aac tat gca cag aag ttt | 192 |
|---|---|
| Gly Trp Ile Asn Pro Asn Ser Gly Gly Thr Asn Tyr Ala Gln Lys Phe | |
| 50                  55                  60 | |

| cag ggc agg gtc acg atg acc agg gac acg tcc atc agc aca gcc tac | 240 |
|---|---|
| Gln Gly Arg Val Thr Met Thr Arg Asp Thr Ser Ile Ser Thr Ala Tyr | |
| 65                  70                  75                  80 | |

| atg gag ctg agc agg ctg aga tct gac gac acg gcc gtg tat tac tgt | 288 |
|---|---|
| Met Glu Leu Ser Arg Leu Arg Ser Asp Asp Thr Ala Val Tyr Tyr Cys | |
|             85                  90                  95 | |

| gca aga gat ggt tac ttc gct gac gcc ttt gat tat tgg ggc caa ggt | 336 |
|---|---|
| Ala Arg Asp Gly Tyr Phe Ala Asp Ala Phe Asp Tyr Trp Gly Gln Gly | |
|         100                 105                 110 | |

| acc ctg gtc acc gtc tcc agt | 357 |
|---|---|
| Thr Leu Val Thr Val Ser Ser | |
|         115 | |

<210> SEQ ID NO 35
<211> LENGTH: 119
<212> TYPE: PRT
<213> ORGANISM: Artificial Sequence
<220> FEATURE:
<223> OTHER INFORMATION: Synthetic Construct 3918 VH

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Tyr Phe Ala Asp Ala Phe Asp Tyr Trp Gly Gln Gly
            100                 105                 110

Thr Leu Val Thr Val Ser Ser
        115

<210> SEQ ID NO 36
<211> LENGTH: 354
<212> TYPE: DNA
<213> ORGANISM: Artificial Sequence
<220> FEATURE:
<223> OTHER INFORMATION: Synthetic: 4327 VH
<220> FEATURE:
<221> NAME/KEY: CDS

<222> LOCATION: (1)..(354)

<400> SEQUENCE: 36

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtt tcc tgc aag gca tct gga tac acc ttc acc agc tac        96
Ser Val Lys Val Ser Cys Lys Ala Ser Gly Tyr Thr Phe Thr Ser Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga ata atc aac cct agt ggt ggt agc aca agc tac gca cag aag ttc       192
Gly Ile Ile Asn Pro Ser Gly Gly Ser Thr Ser Tyr Ala Gln Lys Phe
    50                  55                  60 cag ggc aga gtc acc atg acc agg gac acg tcc acg agc aca gtc tac       240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt       288
Met Glu Leu Ser Ser Leu Arg Ser Glu Asp Thr Ala Val Tyr Tyr Cys
                85                  90                  95 gca aag ggc act act ggt gat tgg ttt gac tac tgg ggc caa ggt acc       336
Ala Lys Gly Thr Thr Gly Asp Trp Phe Asp Tyr Trp Gly Gln Gly Thr
            100                 105                 110 ctg gtc acc gtc tcc agt                                                354
Leu Val Thr Val Ser Ser
            115
```

<210> SEQ ID NO 37
<211> LENGTH: 118
<212> TYPE: PRT
<213> ORGANISM: Artificial Sequence
<220> FEATURE:
<223> OTHER INFORMATION: Synthetic Construct 4237 VH

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Gly Thr Thr Gly Asp Trp Phe Asp Tyr Trp Gly Gln Gly Thr
            100                 105                 110

Leu Val Thr Val Ser Ser
            115
```

<210> SEQ ID NO 38
<211> LENGTH: 354
<212> TYPE: DNA
<213> ORGANISM: Artificial Sequence
<220> FEATURE:
<223> OTHER INFORMATION: Synthetic: 4331 VH
<220> FEATURE:
<221> NAME/KEY: CDS

```
<222> LOCATION: (1)..(354)

<400> SEQUENCE: 38 gag gtc cag ctg gtg cag tct ggg gct gag gtg aag aag cct ggg gcc      48
Glu Val Gln Leu Val Gln Ser Gly Ala Glu Val Lys Lys Pro Gly Ala
1               5                   10                  15 tca gtg aag gtt tcc tgc aag gca tct gga tac acc ttc acc agc tac      96
Ser Val Lys Val Ser Cys Lys Ala Ser Gly Tyr Thr Phe Thr Ser Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga ata atc aac cct agt ggt ggt agc aca agc tac gca cag aag ttc     192
Gly Ile Ile Asn Pro Ser Gly Gly Ser Thr Ser Tyr Ala Gln Lys Phe
    50                  55                  60 cag ggc aga gtc acc atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gca agg ggc aat tat ggt gat gag ttt gac tac tgg ggc caa ggt acc     336
Ala Arg Gly Asn Tyr Gly Asp Glu Phe Asp Tyr Trp Gly Gln Gly Thr
                100                 105                 110 ctg gtc acc gtc tcc agt                                              354
Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct 4331 VH

<400> SEQUENCE: 39

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Gly Asp Glu Phe Asp Tyr Trp Gly Gln Gly Thr
                100                 105                 110

Leu Val Thr Val Ser Ser
        115
```